(12) United States Patent
Mackman et al.

(10) Patent No.: US 8,999,969 B2
(45) Date of Patent: Apr. 7, 2015

(54) ANTI-RSV COMPOUNDS

(75) Inventors: Richard L. Mackman, Millbrae, CA (US); David Sperandio, Palo Alto, CA (US); Hai Yang, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 265 days.

(21) Appl. No.: 13/383,180

(22) PCT Filed: Jul. 7, 2010

(86) PCT No.: PCT/US2010/041186
§ 371 (c)(1),
(2), (4) Date: Mar. 6, 2012

(87) PCT Pub. No.: WO2011/005842
PCT Pub. Date: Jan. 13, 2011

(65) Prior Publication Data
US 2012/0196846 A1     Aug. 2, 2012

Related U.S. Application Data

(60) Provisional application No. 61/224,294, filed on Jul. 9, 2009.

(51) Int. Cl.
*A61K 31/55* (2006.01)
*C07D 495/04* (2006.01)

(52) U.S. Cl.
CPC ................... *C07D 495/04* (2013.01)

(58) Field of Classification Search
USPC .......................... 514/215; 540/586
See application file for complete search history.

(56) References Cited

U.S. PATENT DOCUMENTS

| | | | |
|---|---|---|---|
| 5,512,563 A | 4/1996 | Albright et al. | |
| 5,693,635 A | 12/1997 | Albright et al. | |
| 5,849,735 A | 12/1998 | Albright et al. | |
| 5,869,483 A | 2/1999 | Albright et al. | |
| 2008/0234250 A1 | 9/2008 | Pitt | |
| 2012/0196846 A1 | 8/2012 | Mackman et al. | |

FOREIGN PATENT DOCUMENTS

WO    WO-2005/042530 A1    5/2005

OTHER PUBLICATIONS

International Search Report for PCT/US2010/041186, completion date Sep. 20, 2010.
Sudo, K, et al (2005) "YM-53403, a unique anti-respiratory syncytial virus agent with a novel mechanism of action" *Antiviral Research*, vol. 6 (2): 125-131.

*Primary Examiner* — Brenda Coleman
(74) *Attorney, Agent, or Firm* — Steven R. Eck

(57) ABSTRACT

The present invention relates to anti-RSV compounds of Formula (I) and methods for use of the compounds in the treatment and prevention of RSV infection.

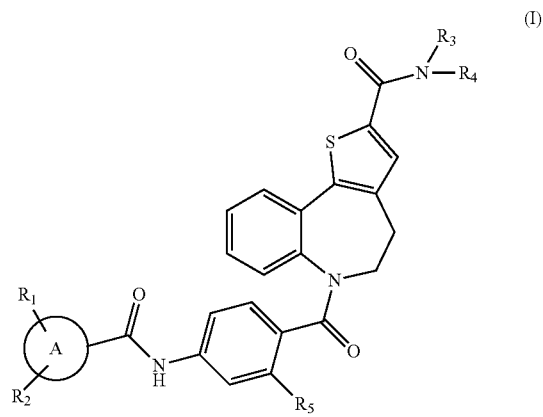

24 Claims, No Drawings

ANTI-RSV COMPOUNDS

This application is a U.S. national stage entry of PCT Application PCT/US2010/041186, published as WO 2011/005842, which claims priority to U.S. Provisional Application No. 61/224,294.

The present invention relates to novel compounds that are used for inhibiting respiratory syncytial virus (RSV) activities and for treating RSV infection in a subject.

The present invention provides a compound of Formula I:

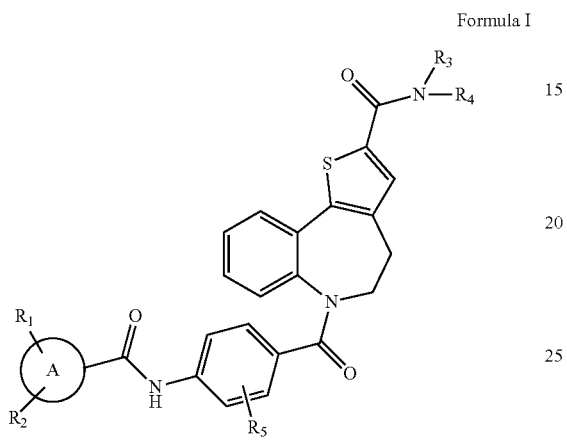

Formula I

A is aryl or heteroaryl;
$R_1$ is alkyl, alkoxy, haloalkyl, aryl, heteroaryl, heterocyclyl, cycloalkyl, said heterocyclyl is optionally substituted by one to three substituents independently selected from the group consisting of halo, hydroxyl, haloalkyl, alkoxy, alkyl, alkoxy-alkyl-, hydroxyl-alkyl-, CN, alkyl-NH—; said aryl or heteroaryl is optionally substituted by one to three substituents independently selected from the group consisting of halo, cyano, nitro, hydroxyl, alkyl, alkoxy, alkyl-NH—, with the proviso that when A is aryl, $R_1$ is not unsubstituted aryl;
$R_2$ is hydrogen, alkyl, alkoxy, amino, alkyl-NH—, CN, alkyl-$SO_2$—, or halo;
$R_3$ is hydrogen, alkyl, heterocyclyl, heteroaryl, heteroaryl-alkyl-, or cycloalkyl, said alkyl is optionally substituted by one substituent selected from the group consisting of $NH_2$—C(O)—, halo, hydroxyl, $NH_2$—$SO_2$—, alkoxy-alkyl-, heterocyclyl; aryl, heteroaryl, CN, alkyl-NH—
$R_4$ is hydrogen, or alkyl; or haloalkyl
$R_3$ and $R_4$ taken together with the nitrogen atom to which they are attached optionally form a 3- to 7-membered ring;
$R_5$ is hydrogen, alkyl, alkoxy, haloalkyl, or halo; or
a pharmaceutically acceptable salt thereof; or an optical isomer thereof, or a mixture of optical isomers.

In one embodiment, according to Formula I, A is $C_6$-$C_{10}$ aryl, or monocyclic 6-membered heteroaryl.

In one embodiment, according to Formula I, A is monocyclic 5-membered heteroaryl or bicyclic 8- to 10-membered heteroaryl.

In one embodiment, according to Formula I, A is a monocyclic 5-membered heteroaryl; $R_1$ is alkyl, or aryl; $R_2$ is hydrogen, or alkyl; $R_3$ is cycloalkyl, or alkyl; $R_4$ is hydrogen; $R_5$ is hydrogen, or halo. Preferably, A is thienyl or pyrazolyl group.

In one embodiment, according to Formula I, A is a bicyclic 8- to 10-membered heteroaryl; $R_1$ is alkyl, or hydrogen; $R_2$ is hydrogen, or alkyl; $R_3$ is cycloalkyl, or alkyl; $R_4$ is hydrogen; $R_5$ is hydrogen, or halo. Preferably, A is indolyl, indazolyl, or quinoxalinyl group.

In one embodiment, the present invention provides a compound of Formula IA:

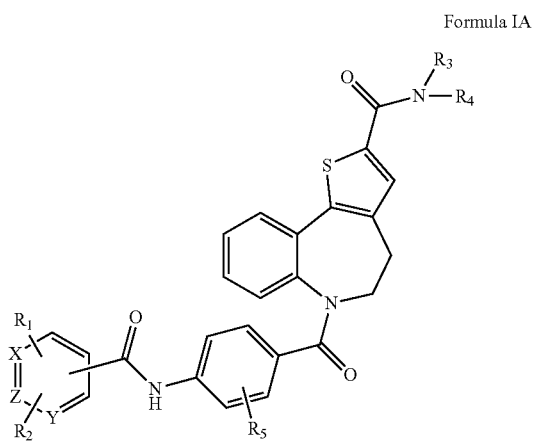

Formula IA wherein X, Y and Z are independently N or CH.
$R_1$ is alkyl, alkoxy, haloalkyl, aryl, heteroaryl, heterocyclyl, said heterocyclyl is optionally substituted by one to three substituents independently selected from the group consisting of halo, hydroxyl, haloalkyl, alkoxy, alkyl, alkoxy-alkyl-, and hydroxyl-alkyl-, said aryl is optionally substituted by one to two substituents independently selected from the group consisting of halo, cyano, nitro and hydroxyl, with the proviso that when X and Y are simultaneously CH, $R_1$ is not unsubstituted aryl;
$R_2$ is hydrogen, alkyl, alkoxy, or halo;
$R_3$ is hydrogen, alkyl, heterocyclyl, heteroaryl, heteroaryl-alkyl-, or cycloalkyl, said alkyl is optionally substituted by one substituent selected from the group consisting of $NH_2$—C(O)—, halo, hydroxyl, $NH_2$—$SO_2$—, alkoxy-alkyl-, and heterocyclyl;
$R_4$ is hydrogen, or alkyl;
$R_3$ and $R_4$ taken together with the nitrogen atom to which they are attached optionally form a 3- to 7-membered ring;
$R_5$ is hydrogen, alkyl, alkoxy, haloalkyl, or halo; or
a pharmaceutically acceptable salt thereof; or an optical isomer thereof, or a mixture of optical isomers.

In one embodiment, according to Formula IA, X and Z are CH, Y is N.

In one embodiment, according to Formula IA, X, Y and Z are CH.

In one embodiment, according to Formula IA, X and Z are N, Y is CH.

In one embodiment, according to Formula IA, X and Z are CH; Y is N; $R_1$ is haloalkyl, or heterocyclyl, said heterocyclyl is optionally substituted by one to two substituents independently selected from the group consisting of halo, hydroxyl, alkoxy-alkyl-, alkyl, haloalkyl, or hydroxyl-alkyl-; $R_2$ is hydrogen; $R_3$ is hydrogen, alkyl, heteroaryl, heteroaryl-alkyl-, or cycloalkyl, said alkyl is optionally substituted by one substituent selected from the group consisting of $NH_2$—C(O)—, halo, hydroxyl, $NH_2$—$SO_2$—, alkoxy-alkyl-, and heterocyclyl; $R_4$ is hydrogen, or alkyl; $R_3$ and $R_4$ taken together with the nitrogen atom to which they are attached optionally form a 3- to 7-membered ring; $R_5$ is hydrogen, or halo; or a pharmaceutically acceptable salt thereof; or an optical isomer thereof, or a mixture of optical isomers. Preferably, $R_1$ is ($C_1$-$C_4$)haloalkyl, or 4- to 7-membered heterocyclyl, said heterocyclyl is optionally substituted by one to two substituents independently selected from the group consisting of halo, hydroxyl, $(C_1-C_4)$alkoxy-$(C_1-C_4)$alkyl-, $(C_1-C_4)$alkyl, $(C_1-C_4)$haloalkyl, or hydroxyl-$(C_1-C_4)$alkyl-; $R_3$ is hydrogen, $(C_1-C_4)$alkyl, 5- to 9-membered heteroaryl, 5- to 9-membered heteroaryl-$(C_1-C_4)$alkyl-, or $(C_3-C_7)$cycloalkyl, said alkyl is optionally substituted by one substituent selected from the group consisting of $NH_2$—C(O)—, halo, hydroxyl, $NH_2$—$SO_2$—, $(C_1-C_4)$alkoxy-$(C_1-C_4)$alkyl-, and 4- to 7-membered heterocyclyl; $R_4$ is hydrogen, or $(C_1-C_4)$alkyl.

In one embodiment, X, Y and Z are CH; $R_1$ is alkyl, alkoxy, or heteroaryl; $R_2$ is hydrogen, or alkoxy; $R_3$ is cycloalkyl; $R_4$ and $R_5$ are hydrogen; or a pharmaceutically acceptable salt thereof; or an optical isomer thereof, or a mixture of optical isomers. Preferably, $R_1$ is $(C_1-C_4)$alkyl, $(C_1-C_4)$alkoxy, or 5- to 9-membered heteroaryl; $R_2$ is hydrogen, or $(C_1-C_4)$alkoxy; $R_3$ is $(C_3-C_7)$cycloalkyl; $R_4$ and $R_5$ are hydrogen.

In one embodiment, X and Z are N, Y is CH; $R_1$ is alkyl, alkoxy, or heterocyclyl; $R_2$ is alkyl; $R_3$ is cycloalkyl; $R_4$ and $R_5$ are hydrogen; or a pharmaceutically acceptable salt thereof; or an optical isomer thereof, or a mixture of optical isomers.

In one embodiment, the present invention provides a compound of Formula IB:

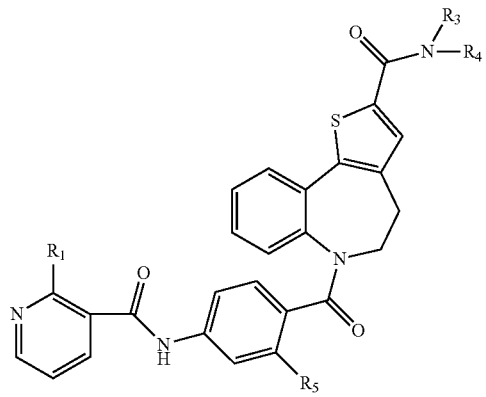

Formula IB wherein $R_1$ is haloalkyl, or heterocyclyl, said heterocyclyl is optionally substituted by one to two substituents independently selected from the group consisting of halo, hydroxyl, alkoxy-alkyl-, alkyl, haloalkyl, or hydroxyl-alkyl-; $R_3$ is hydrogen, alkyl, heterocyclyl, heteroaryl, heteroaryl-alkyl-, or cycloalkyl, said alkyl is optionally substituted by one substituent selected from the group consisting of $NH_2$—C(O)—, halo, or hydroxyl; $R_4$ is hydrogen; $R_5$ is hydrogen, or halo; or a pharmaceutically acceptable salt thereof; or an optical isomer thereof, or a mixture of optical isomers.

In one embodiment, according to Formula IB, $R_1$ is heterocyclyl that is optionally substituted by one to two substituents independently selected from the group consisting of halo, hydroxyl, alkoxy-alkyl-, alkyl, haloalkyl, or hydroxyl-alkyl-. Preferably, $R_1$ is 4- to 5-membered heterocyclyl, or 7-membered heterocyclyl. Preferably, $R_1$ is 4- to 5-membered heterocyclyl, or 7-membered heterocyclyl Preferably, $R_1$ is pyrrolidinyl, azetidinyl, or 2-oxa-6-azaspiro[3,3]heptan-6-yl.

In one embodiment, according to Formula IB, $R_3$ is hydrogen, alkyl, cycloalkyl, heteroaryl, heteroaryl-alkyl-, or heterocyclyl, said alkyl is optionally substituted by one substituent selected from the group consisting of halo, or hydroxyl. Preferably, $R_3$ is, hydrogen, $(C_3-C_7)$cycloalkyl, 4- to 7-membered heterocyclyl, or $(C_1-C_4)$alkyl that is optionally substituted by one halo group. Preferably, $R_3$ is cyclopropyl.

In one embodiment, according to Formula IB, $R_1$ is 4- to 7-membered heterocyclyl that is optionally substituted by one to two substituents independently selected from the group consisting of halo, hydroxyl, $(C_1-C_4)$alkoxy-$(C_1-C_4)$alkyl-, $(C_1-C_4)$alkyl, $(C_1-C_4)$haloalkyl, or hydroxyl-$(C_1-C_4)$alkyl-; $R_3$ is hydrogen, $(C_3-C_7)$cycloalkyl, 4- to 7-membered heterocyclyl, or $(C_1-C_4)$alkyl that is optionally substituted by one halo group or one 5- to 6-membered heteroaryl group; $R_4$ and $R_5$ are hydrogen; or a pharmaceutically acceptable salt thereof; or an optical isomer thereof, or a mixture of optical isomers.

In one embodiment, according to Formula IB, $R_1$ is pyrrolidinyl; $R_3$ is hydrogen, cyclopropyl, or $(C_1-C_4)$alkyl that is optionally substituted by one halo group or one 5- to 6-membered heteroaryl group; $R_4$ and $R_5$ are hydrogen; or a pharmaceutically acceptable salt thereof; or an optical isomer thereof, or a mixture of optical isomers.

In one embodiment, according to Formula IB, $R_1$ is azetidinyl or 2-oxa-6-azaspiro[3,3]heptan-6-yl; $R_3$ is cyclopropyl; $R_4$ and $R_5$ are hydrogen; or a pharmaceutically acceptable salt thereof; or an optical isomer thereof, or a mixture of optical isomers.

In one embodiment, the present invention provides a compound of Formula IC:

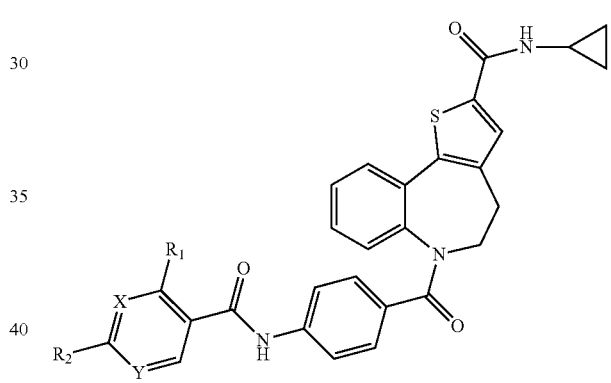

Formula IC wherein
$R_1$ is cycloalkylamino, alkyl, haloalkyl, heteroaryl, or aryl that is substituted with one halogen group;
$R_2$ is hydrogen; and
X and Y are independently N or CH; or
a pharmaceutically acceptable salt thereof; or an optical isomer thereof, or a mixture of optical isomers.

Alternatively, $R_1$ is alkyl, $R_2$ is alkoxy, and X and Y are both CH; or a pharmaceutically acceptable salt thereof.

Preferably, the present invention provides the compound of formula I, wherein $R_1$ is (4 to 6-membered)-cycloalkylamino, $(C_1-C_4)$ alkyl, $(C_1-C_4)$ haloalkyl, phenyl, or thiophene, said phenyl being optionally substituted with one fluorine group; $R_2$ is hydrogen; and X and Y are independently N or CH; or a pharmaceutically acceptable salt thereof.

Preferably, the present invention provides the compound of formula I, wherein $R_1$ is $(C_1-C_4)$ alkyl; $R_2$ is $(C_1-C_4)$ alkoxy; and X and Y are both CH; or a pharmaceutically acceptable salt thereof.

Also preferably, the present invention provides the compound of formula I, or a pharmaceutically acceptable salt, or an optical isomer thereof, or a mixture of optical isomers, wherein the compound is represented by the following structures:

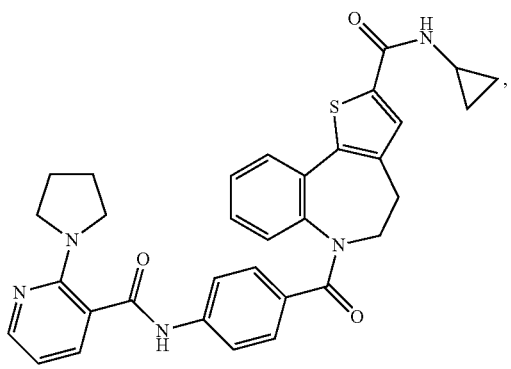
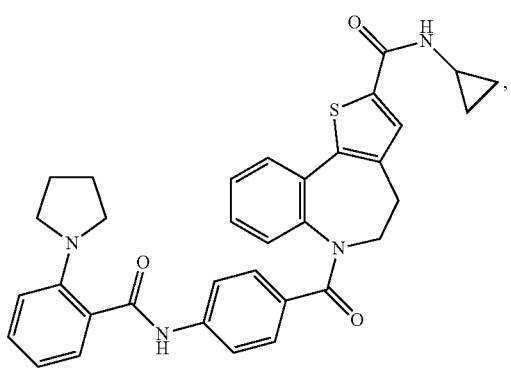
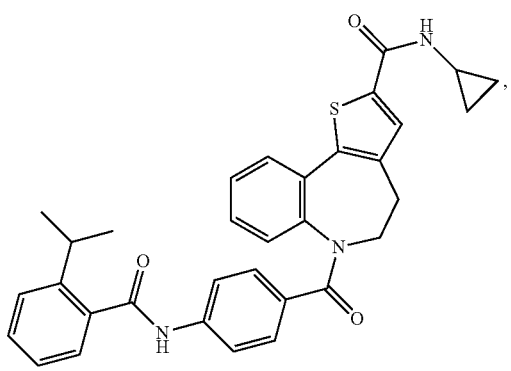
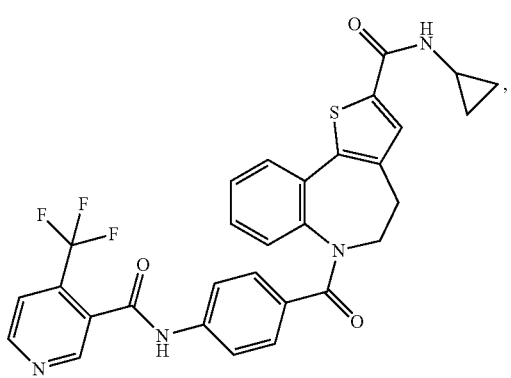
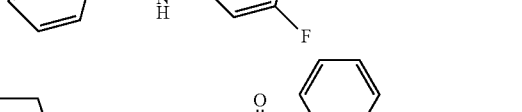

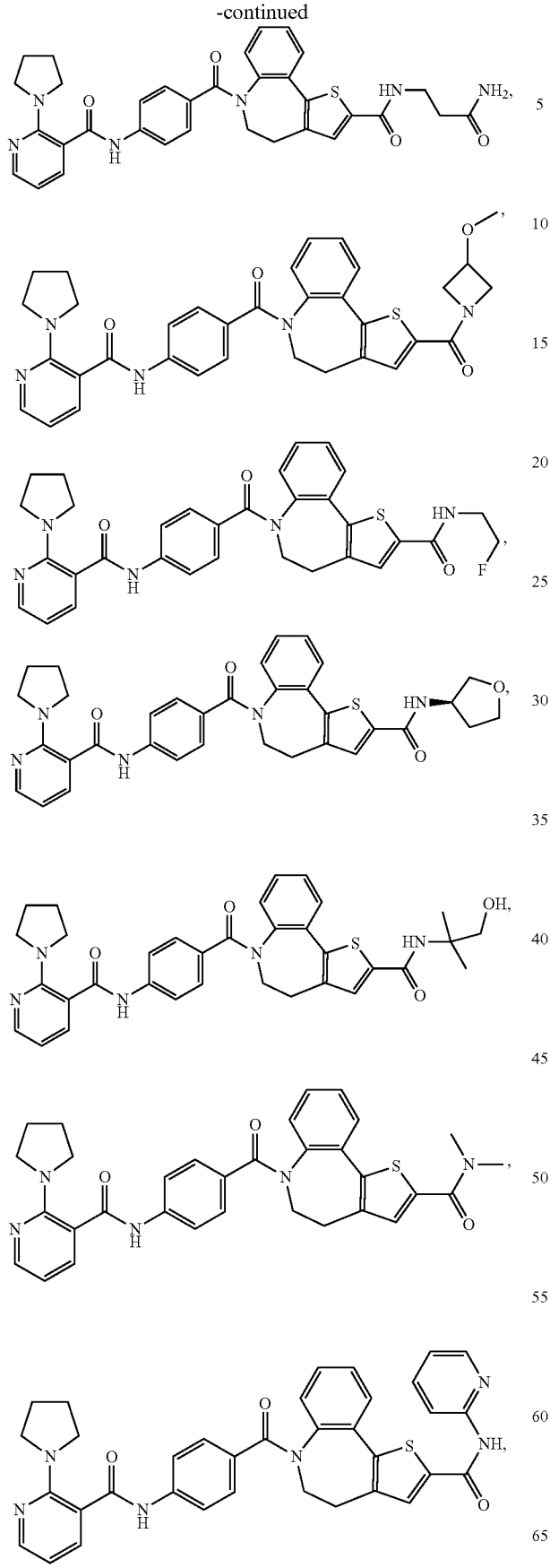
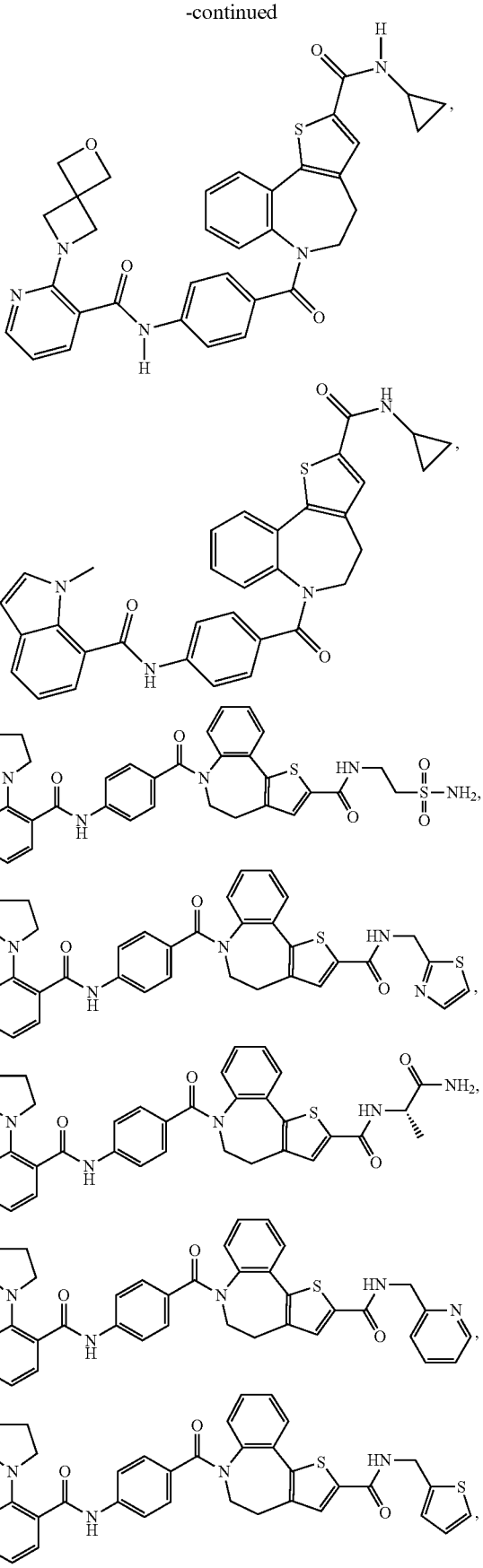

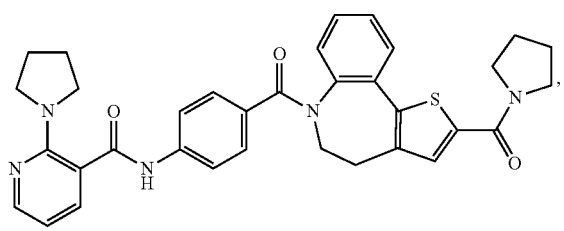
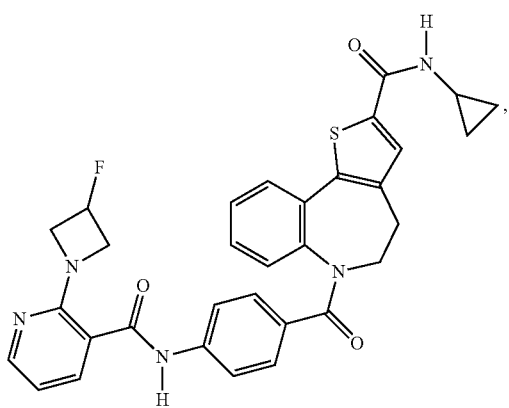
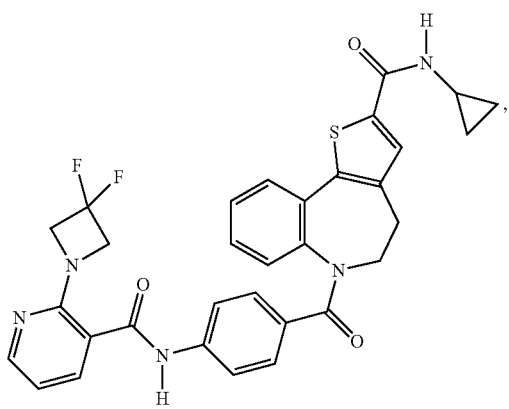
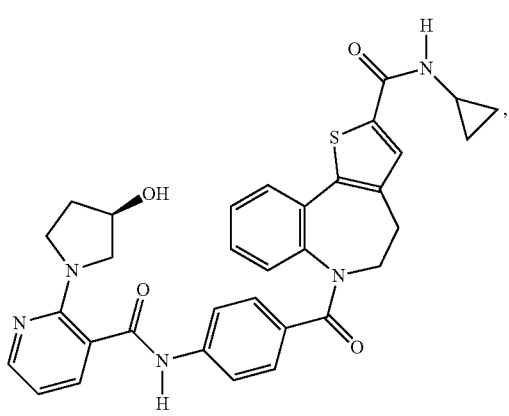
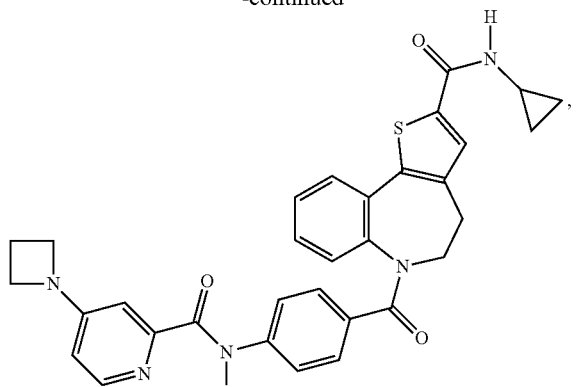
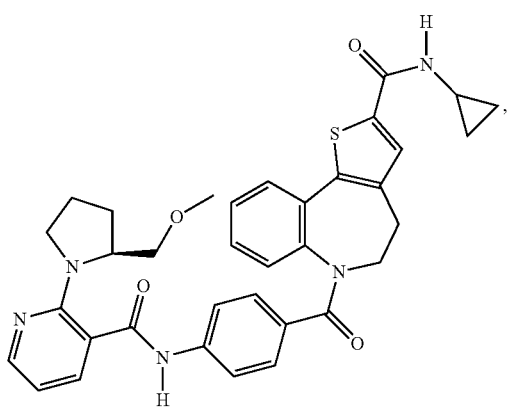
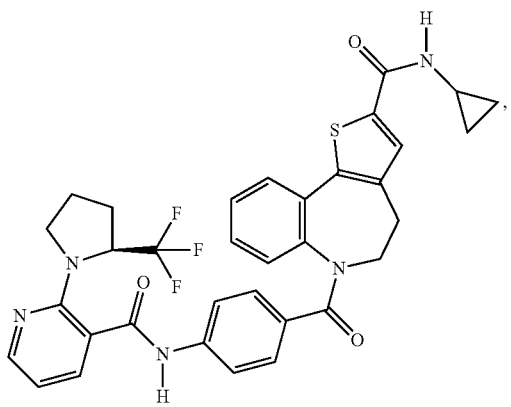
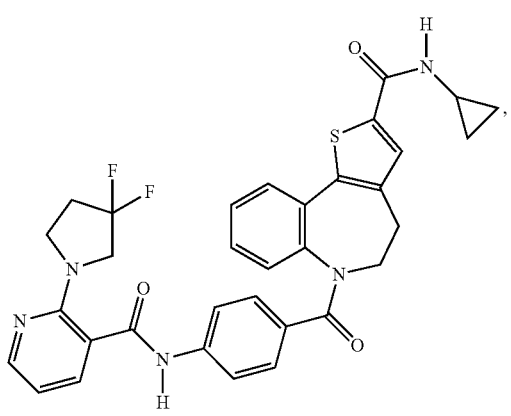

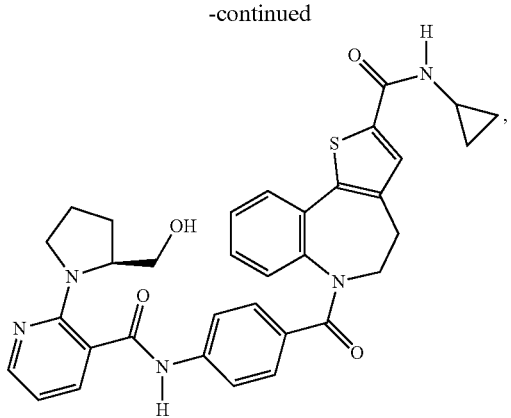
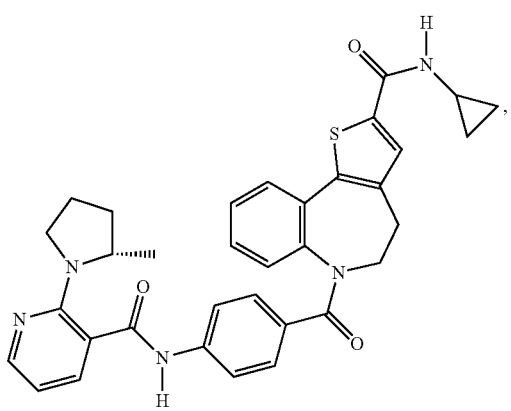
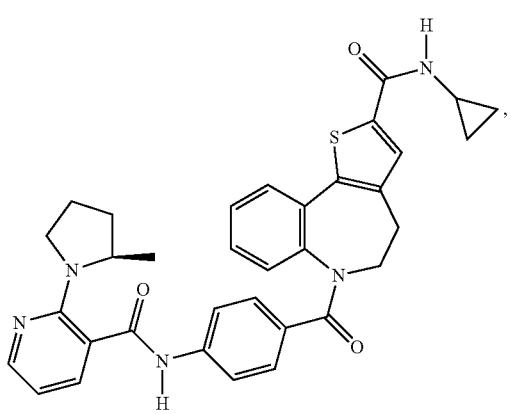
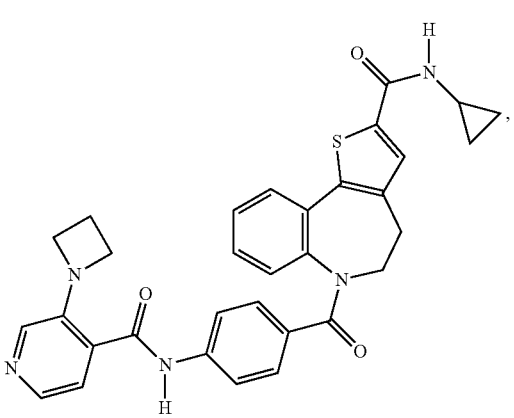
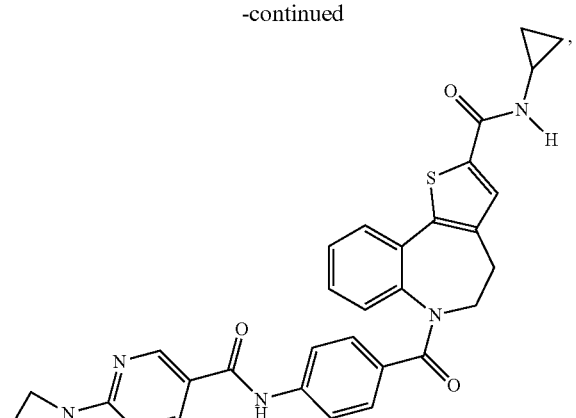
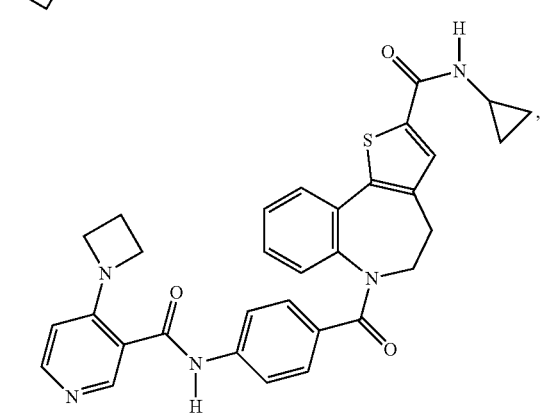
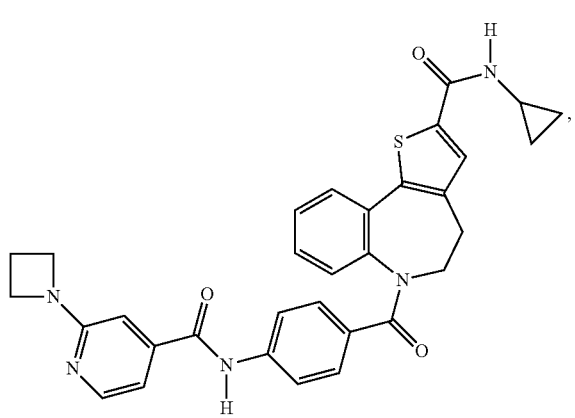
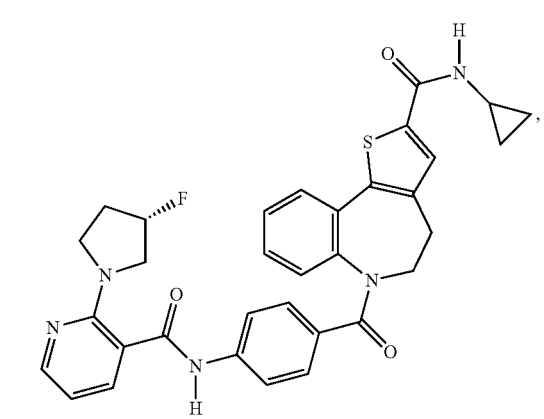

-continued
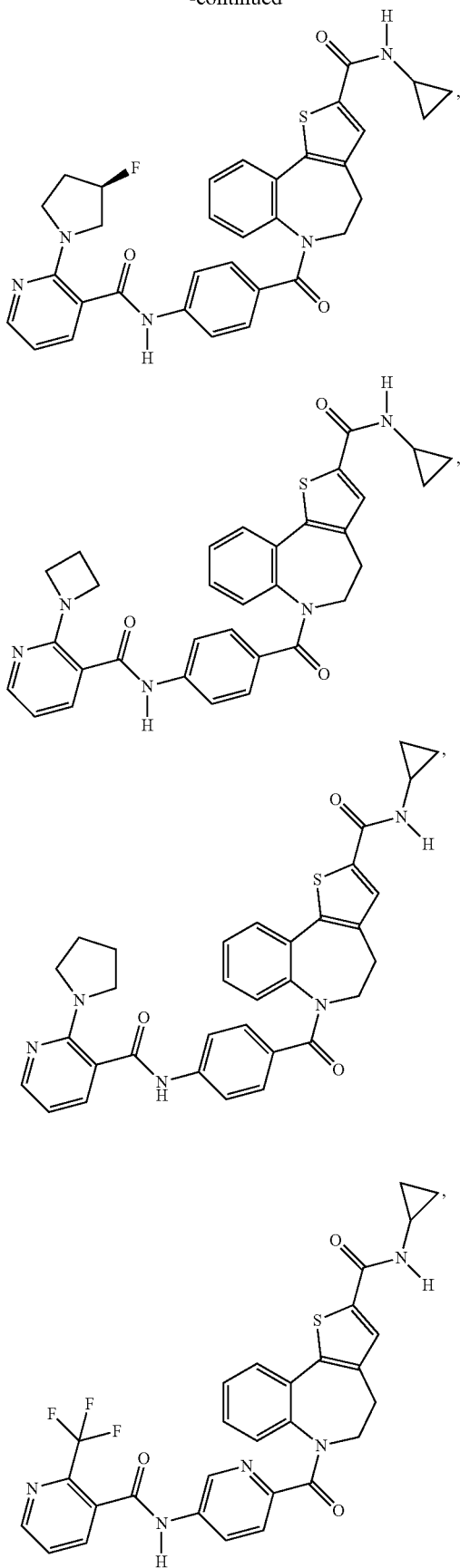
-continued
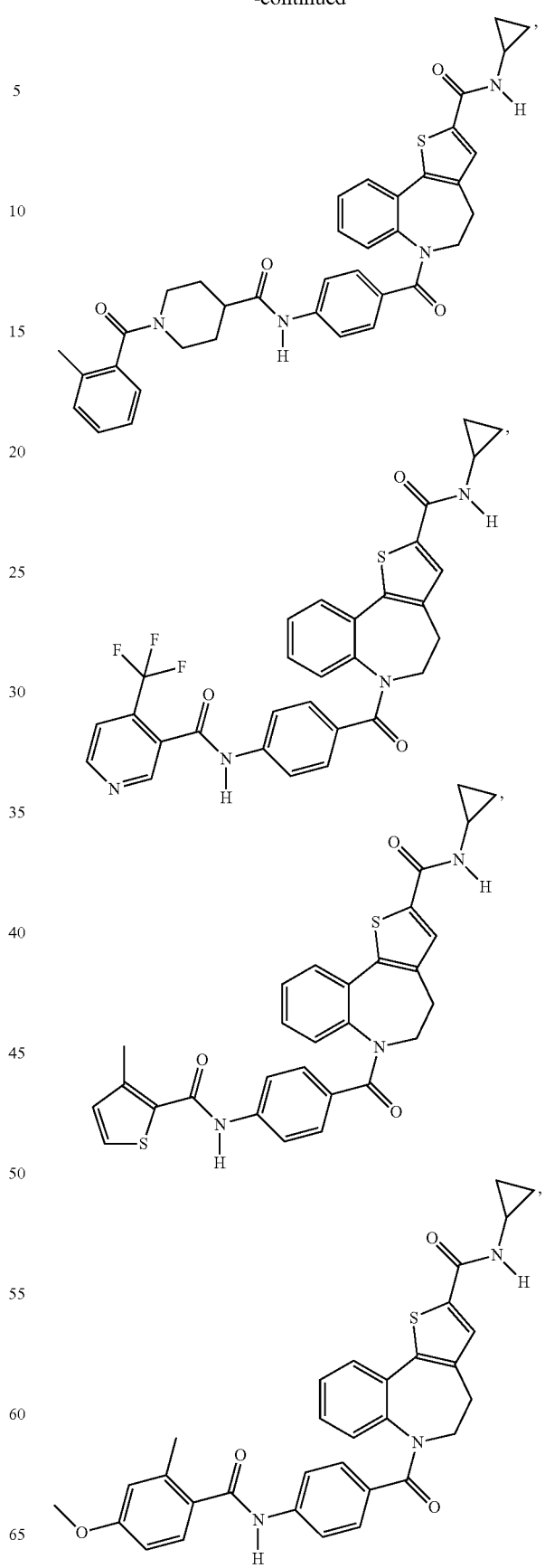

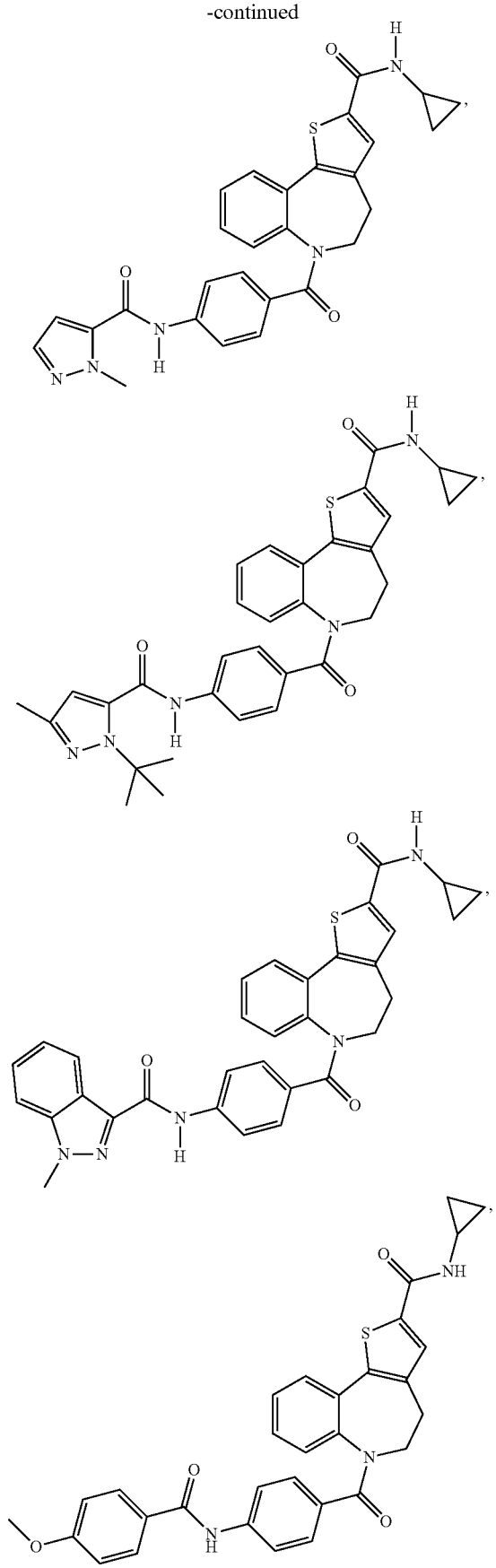
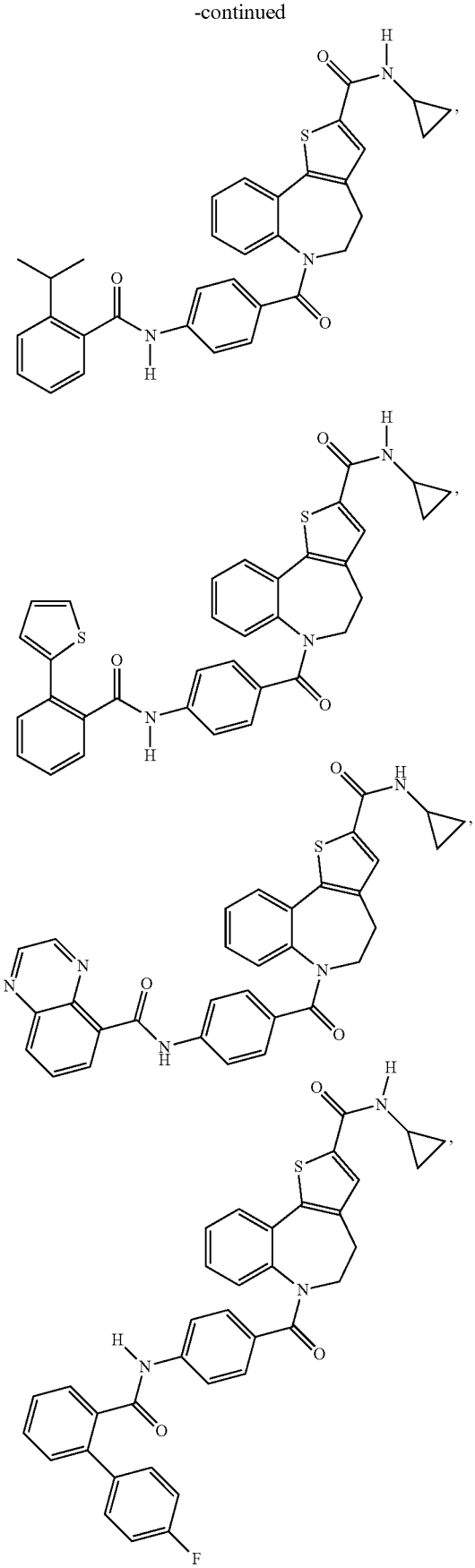

-continued

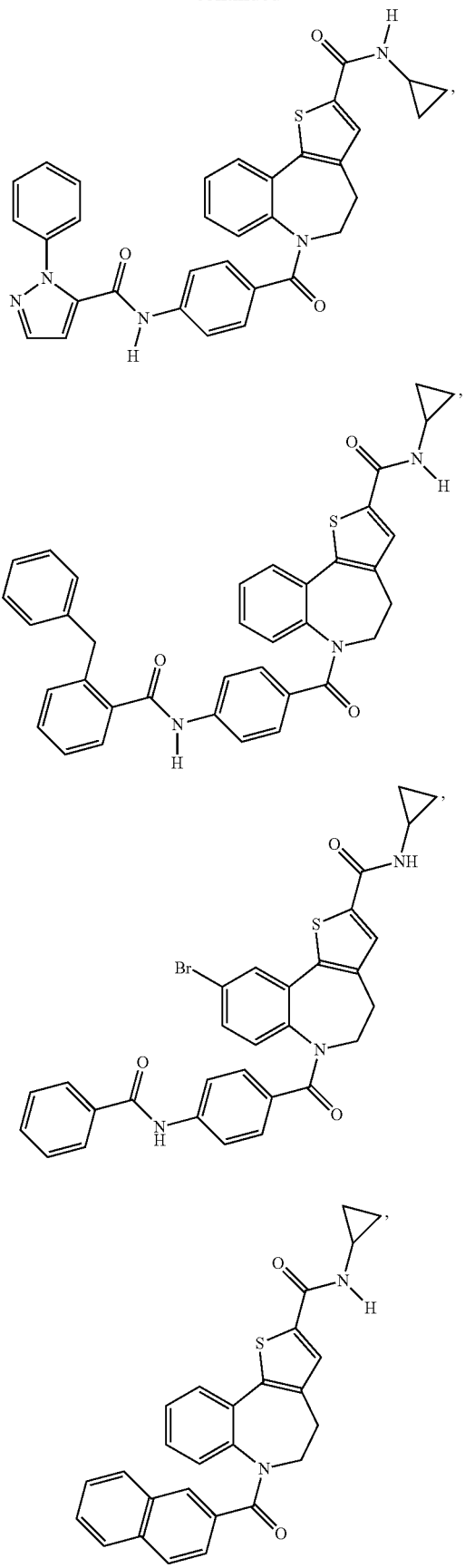

-continued

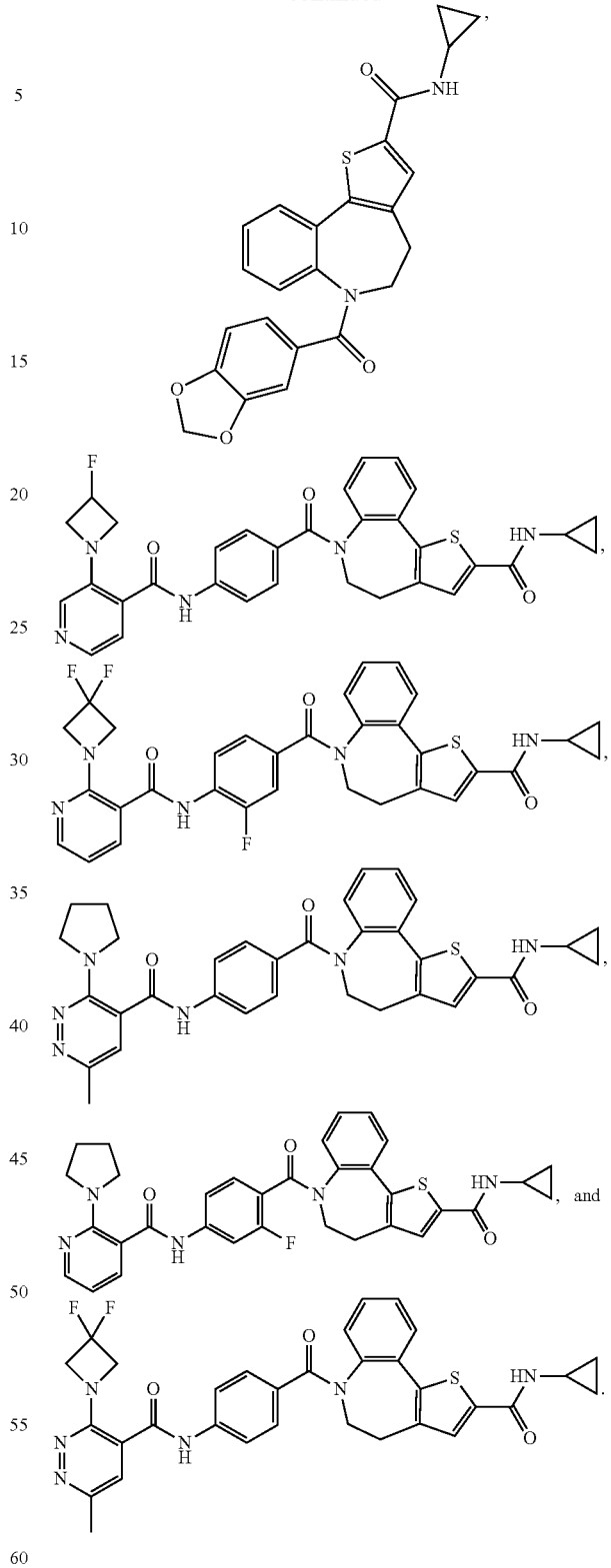

For purposes of interpreting this specification, the following definitions will apply and whenever appropriate, terms used in the singular will also include the plural and vice versa.

As used herein, the term "alkyl" refers to a saturated branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. When an alkyl group includes one or more unsaturated bonds, it may be referred to as an alkenyl (double bond) or an alkynyl (triple bond) group. Furthermore, when an alkyl group is linked to an aryl group (defined below), it may be referred to as an "arylalkyl" group.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. As used herein, the term "lower alkoxy" refers to the alkoxy groups having 1-7 carbons and preferably 1-4 carbons.

The term "aryl" refers to monocyclic or bicyclic aromatic hydrocarbon groups having 6-16 carbon atoms in the ring portion. Preferably, the aryl is a ($C_6$-$C_{10}$) aryl. Non-limiting examples include phenyl, biphenyl, naphthyl or tetrahydronaphthyl, each of which may optionally be substituted by 1-4 substituents, such as optionally substituted alkyl, trifluoromethyl, cycloalkyl, halo, hydroxy, alkoxy, acyl, alkyl-C(O)—O—, aryl-O—, heteroaryl-O—, optionally substituted amino, thiol, alkylthio, arylthio, nitro, cyano, carboxy, alkyl-O—C(O)—, carbamoyl, alkylthiono, sulfonyl, sulfonamido, heterocycloalkyl and the like.

Furthermore, the term "aryl" as used herein, also refers to an aromatic substituent which can be a single aromatic ring, or multiple aromatic rings that are fused together, linked covalently, or linked to a common group such as a methylene or ethylene moiety. The common linking group also can be a carbonyl as in benzophenone or oxygen as in diphenylether or nitrogen as in diphenylamine.

As used herein, the term "cycloalkyl" refers to optionally substituted saturated or unsaturated monocyclic, bicyclic or tricyclic hydrocarbon groups of 3-12 carbon atoms, each of which may be substituted by one or more substituents, such as alkyl, halo, oxo, hydroxy, alkoxy, alkanoyl, acylamino, carbamoyl, alkylamino, dialkylamino, thiol, alkylthio, nitro, cyano, carboxy, alkoxycarbonyl, sulfonyl, sulfonamido, sulfamoyl, heterocyclyl and the like.

Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl; bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

As used herein, the term "cycloalkylamino" refers to a cycloalkyl group as defined herein wherein one carbon atom on the ring is substituted with a nitrogen atom and the cycloalkylamino group is attached via the nitrogen atom to the dependent molecule.

As used herein, the term "haloalkyl" refers to an alkyl as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. Preferably, the polyhaloalkyl contains up to 12, 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

As used herein, the term "heteroaryl" refers to a 5-14 membered monocyclic- or bicyclic- or fused polycyclic-ring system, having 1 to 8 heteroatoms selected from N, O or S. Preferably the heteroaryl is mono-, bi-, or tricyclic, more preferably mono- or bicyclic. Preferably, the heteroaryl is a 5-10 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 3-, 4-, 5-, or 6-pyridinyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 4-, or 6-triazinyl, 2-, 3-, or 4-pyridyl, 3- or 4-pyridazinyl, 3-, 4-, or 5-pyrazinyl, 2-pyrazinyl, 2-, 4-, or 5-pyrimidinyl, 4- or 5-1-oxa-2,3-diazolyl, 3- or 5-1-oxa-2,4-diazolyl, 3- or 4-1-oxa-2,5-diazolyl, 2- or 5-1-oxa-3,4-diazolyl, 4- or 5-1-thia-2,3-diazolyl, 3- or 5-1-thia-2,4-diazolyl, 3- or 4-1-thia-2,5-diazolyl, 2- or 5-1-thia-3,4-diazolyl, and the like.

The term "heteroaryl" also refers to a group in which a heteroaromatic ring is fused to one or more aryl, partially unsaturated cycloaliphatic, or partially unsaturated heterocycloalkyl rings, where the radical or point of attachment is on the heteroaromatic ring. Nonlimiting examples include but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1—, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, 11-1H-pyrrolo[1,2-b][2]benzazapinyl, benzo[b]furanyl, 2-, 3-, 5-, 6-, 7- or 8-quinoxalinyl, 1-, 2-, 3-, 4-, 5-, 6-, or 7-indenyl, 1-, 2-, 3-, 4-, 5-, 6-, 7-, or 8-azulenyl, 1-, 2-, 3-, 4-, 5-, 6-, 7-, 8-, or 9-fluorenyl, benzothiphenyl, benzimidazolyl, indazolyl, benzotriazolyl, pyrrolo[2,3-b]pyridinyl, pyrrolo[2,3-c]pyridinyl, pyrrolo[3,2-c]pyridinyl, pyrrolo[3,2-b]pyridinyl, pyrrolo[1,5-a]pyridinyl, pyrrolo[1,5-b]pyridinyl, imidazo[4,5-b]pyridinyl, imidazo[4,5-c]pyridinyl, imidazo[4,3-d]pyridinyl, imidazo[4,3-c]pyridinyl, imidazo[1,2-a]pyridinyl, imidazo[1,5-a]pyridinyl, pyrazolo

[1,5-a]pyridinyl, pyrrolo[1,2-b]pyridazinyl, thienopyrimidinyl, isoquinolinyl, 1,8-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrimidinyl, pyrazino[2,3-b]pyrimidinyl, pyrimido[5,4-d]pyrimidinyl, pyrazino[2,3-b]pyrazinyl, or pyrimido[4,5-d]pyrimidinyl. Typical fused heteroaryl groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl, 2-, 3-, 4-, 5-, 6-, or 7-.

A heteroaryl group may be mono-, bi-, tri-, or polycyclic, preferably mono-, bi-, or tricyclic, more preferably mono- or bicyclic.

As used herein, the term "heterocycloalkyl" or "heterocyclyl" refers to an optionally substituted, saturated or partially unsaturated, nonaromatic cyclic group, e.g., which is a 4- to 7-membered monocyclic, 7- to 12-membered bicyclic or 10- to 15-membered tricyclic ring system, which has at least one heteroatom in at least one carbon atom-containing ring. Each ring of the heterocyclic group containing a heteroatom may have 1, 2, 3, or 4 heteroatoms selected from nitrogen atoms, oxygen atoms and sulfur atoms, wherein the nitrogen and sulfur heteroatoms may also optionally be oxidized. The heterocyclic group may be attached at a heteroatom or a carbon atom. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. The bicyclic and tricyclic heterocyclyl groups can be fused or spiro rings or ring groups.

Exemplary monocyclic heterocyclic groups include oxetanyl, thiatanyl, azetidinyl, dihydrofuranyl, tetrahydrofuranyl, dihydrothiophenyl, tetrahydrothiophenyl, pyrrolidinyl, dihydropyrazolyl, tetrahydropyrazolyl, dihydropyridinyl, tetrahydropyridinyl, dihydrothiopyranyl, tetrahydrothipyranyl, pyranyl, dihydropyranyl, tetrahydropyranyl, thiopyranyl, dihydrothiopyranyl, tetrahydrothiopyranyl, piperidinyl, piperazinyl, morpholinyl, azepinyl, dihydroazepinyl, tetrahydroazepinyl, 2-oxopiperazinyl, 2-oxopiperidinyl, 2-oxopyrrolodinyl, 2-oxoazepinyl, oxepanyl, thiepanyl, dihyrothiepinyl, tetrahydrothiepinyl, dihydrooxepinyl, tetrahydrooxepinyl, 1,4-dioxanyl, 1,4-oxathianyl, morpholinyl, oxazolyl, oxazolidinyl, isoxazolinyl, 4-piperidonyl, isoxazolinyl, isoxazolyl, 1,4-azathianyl, 1,4-oxathiepanyl, 1,4-oxaazepanyl, 1,4-dithiepanyl, 1,4-thieaxepanyl, 1,4-diazepanyl, tropanyl, 3,4-dihydro-2H-pyranyl, 5,6-dihydro-2H-pyranyl, thiazolidinyl, thiamorpholinyl, thiamorpholinyl sulfoxide, thiamorpholinyl sulfone, 1,3-dioxolane and tetrahydro-1,1-dioxothienyl, 1,1,4-trioxo-1,2,5-thiadiazolidin-2-yl, pyrazolinyl, and the like.

Exemplary bicyclic heterocyclic groups include but are not limited to, dihydroindolyl, quinuclidinyl, tetrahydroquinolinyl, decahydroquinolinyl, 2-oxa-6-azaspiro[3,3]heptan-6-yl, tetrahydroisoquinolinyl, decahydroisoquinolinyl, dihydroisoindolyl, indolinyl, norboranyl, adamantanyl, and the like.

As used herein, the term "carbamoyl" refers to $H_2NC(O)$—, alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aryl-alkyl-NHC(O)—, alkyl(aryl-alkyl)-NC(O)— and the like.

As used herein, the term "sulfonamido" refers to alkyl-S(O)$_2$—NH—, aryl-S(O)$_2$—NH—, aryl-alkyl-S(O)$_2$—NH—, heteroaryl-S(O)$_2$—NH—, heteroaryl-alkyl-S(O)$_2$—NH—, alkyl-S(O)$_2$—N(alkyl)-, aryl-S(O)$_2$—N(alkyl)-, aryl-alkyl-S(O)$_2$—N(alkyl)-, heteroaryl-S(O)$_2$—N(alkyl)-, heteroaryl-alkyl-S(O)$_2$—N(alkyl)- and the like.

As used herein, the term "sulfonyl" refers to R—SO$_2$—, wherein R is hydrogen, alkyl, aryl, heteroaryl, aryl-alkyl, heteroaryl-alkyl, aryl-O—, heteroaryl-O—, alkoxy, aryloxy, cycloalkyl, or heterocyclyl.

As used herein, the term "acyl" refers to a group R—C(O)— of from 1 to 10 carbon atoms of a straight, branched, or cyclic configuration or a combination thereof, attached to the parent structure through carbonyl functionality. Such group may be saturated or unsaturated, and aliphatic or aromatic. Preferably, R in the acyl residue is alkyl, or alkoxy, or aryl, or heteroaryl. Also preferably, one or more carbons in the acyl residue may be replaced by nitrogen, oxygen or sulfur as long as the point of attachment to the parent remains at the carbonyl. Examples include but are not limited to, acetyl, benzoyl, propionyl, isobutyryl, t-butoxycarbonyl, benzyloxycarbonyl and the like. Lower acyl refers to acyl containing one to four carbons.

As used herein, the term "sulfamoyl" refers to $H_2NS(O)_2$—, alkyl-NHS(O)$_2$—, (alkyl)$_2$NS(O)$_2$—, aryl-NHS(O)$_2$—, alkyl(aryl)-NS(O)$_2$—, (aryl)$_2$NS(O)$_2$—, heteroaryl-NHS(O)$_2$—, aralkyl-NHS(O)$_2$—, heteroaralkyl-NHS(O)$_2$— and the like.

As used herein, the term "aryloxy" refers to both an —O-aryl and an —O-heteroaryl group.

As used herein, the term "halo" or "halogen" refers to fluoro, chloro, bromo, and iodo.

As used herein, the term "isomers" refers to different compounds that have the same molecular formula. Also as used herein, the term "an optical isomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)— or (S)—. The present invention is meant to include all such possible isomers, including racemic mixtures, optically pure forms and intermediate mixtures. Optically active (R)— and (S)— isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the term "pharmaceutically acceptable salts" refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto (e.g., phenol or hydroxyamic acid). Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in *Remington's Pharmaceutical Sciences,* 20th ed., Mack Publishing Company, Easton, Pa., (1985), which is herein incorporated by reference.

As used herein, the term "pharmaceutically acceptable carrier/excipient" includes any and all solvents, dispersion media, coatings, surfactants, antioxidants, preservatives (e.g., antibacterial agents, antifungal agents), isotonic agents, absorption delaying agents, salts, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except in so far as any conventional carrier is incompatible with the active ingredient, its use in the therapeutic or pharmaceutical compositions is contemplated.

The term "therapeutically effective amount" of a compound of the present invention refers to an amount of the compound of the present invention that will elicit the biological or medical response of a subject, or ameliorate symptoms, slow or delay disease progression, or prevent a disease, etc.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "a disorder" or "a disease" refers to any derangement or abnormality of function; a morbid physical or mental state. See *Darland's Illustrated Medical Dictionary,* (W.B. Saunders Co. 27th ed. 1988).

As used herein, the term "inhibition" or "inhibiting" refers to the reduction or suppression of a given condition, symptom, or disease, or a significant decrease in the baseline activity of a biological activity or process. In one embodiment this refers to the ability to block the production of infectious RSV virus particles.

As used herein, the term "treating" or "treatment" of any disease or disorder refers to both therapeutic and prophylactic treatment. In one embodiment, therapeutic treatment refers to ameliorating the disease or disorder (i.e., arresting or reducing the development of the disease or at least one of the clinical symptoms thereof). In another embodiment, therapeutic treatment refers to ameliorating at least one physical parameter, which may not be discernible by the patient. In yet another embodiment, therapeutic treatment refers to modulating the disease or disorder, either physically, (e.g., stabilization of a discernible symptom), physiologically, (e.g., stabilization of a physical parameter), or both. In yet another embodiment, therapeutic treatment refers to delaying the onset or development or progression of the disease or disorder. Prophylactic treatment refers to reducing the likelihood of contracting disease or disorder, such as contracting the viral infection or developing an adverse condition in a subject when exposed to a virus. Preferably, the viral infection is reduced by about 10, about 20, about 30, about 40, about 50, about 60, about 70, about 80% or greater as compared to untreated controls.

It will be appreciated that the compounds of the present invention may have at least one asymmetric center. Therefore, the compounds are capable of existing in more than one stereoisomeric form. Any asymmetric carbon atom on the compounds of the present invention can be present in the (R)—, (S)— or (R,S)— configuration, preferably in the (R)— or (S)-configuration. Therefore, the compounds of the present invention can be in the form of one of the possible isomers or mixtures thereof including racemates. Any resulting mixtures of isomers can be separated on the basis of the physicochemical differences of the constituents, into the pure geometric or optical isomers, diastereomers, racemates, for example, by known methods such as chromatography and/or fractional crystallization. The invention also provides isotopically enriched compounds that are compounds of formula I that comprise an enriched isotope at one or more positions in the compound.

The compounds of the present invention are either obtained in the free form or as a salt form thereof. When a basic group is present in the compounds of the present invention, the compounds can be converted into acid addition salts thereof, in particular, acid addition salts with the imidazolyl moiety of the structure, preferably pharmaceutically acceptable salts thereof. These are formed, with inorganic acids or organic acids. Suitable inorganic acids include but are not limited to, hydrochloric acid, sulfuric acid, a phosphoric or hydrohalic acid. Suitable organic acids include but are not limited to, carboxylic acids, such as ($C_1$-$C_4$) alkanecarboxylic acids which, for example, are unsubstituted or substituted by halogen, e.g., acetic acid, such as saturated or unsaturated dicarboxylic acids, e.g., oxalic, succinic, maleic or fumaric acid, such as hydroxycarboxylic acids, e.g., glycolic, lactic, malic, tartaric or citric acid, such as amino acids, e.g., aspartic or glutamic acid, organic sulfonic acids, such as ($C_1$-$C_4$) alkylsulfonic acids, e.g., methanesulfonic acid; or arylsulfonic acids which are unsubstituted or substituted, e.g., by halogen. Preferred are salts formed with hydrochloric acid, methanesulfonic acid and maleic acid.

When an acidic group is present in the compounds of the present invention, the compounds can be converted into salts with pharmaceutically acceptable bases. Such salts include alkali metal salts, like sodium, lithium and potassium salts; alkaline earth metal salts, like calcium and magnesium salts; ammonium salts with organic bases, e.g., trimethylamine salts, diethylamine salts, tris(hydroxymethyl)methylamine salts, dicyclohexylamine salts and N-methyl-D-glucamine salts; salts with amino acids like arginine, lysine and the like. Salts may be formed using conventional methods, advantageously in the presence of an ethereal or alcoholic solvent, such as a lower alkanol. From the solutions of the latter, the salts may be precipitated with ethers, e.g., diethyl ether. Resulting salts may be converted into the free compounds by treatment with acids. These or other salts can also be used for purification of the compounds obtained.

When both a basic group and an acid group are present in the same molecule, the compounds of the present invention can also form internal salts.

The compounds of the present invention are active RSV inhibitors, thus, have valuable pharmaceutical properties. The present invention therefore provides a method for treating a subject infected with RSV or prophylactic treatment of individuals susceptible to an RSV infection. The method comprises administering to said subject an effective amount of a compound of the present invention or a pharmaceutically acceptable carrier thereof. RSV is the leading cause of viral bronchiolitis and pneumonia in babies and children and is also responsible for much severe influenza-like illness in vulnerable adults including the elderly and immunocompromised individuals RSV is prevalent among the general population during the winter months. It is a particularly serious risk amongst children who suffer from chronic lung disease, children with congenital heart disease and children born preterm. Accordingly, the compounds of the present invention are typically for use in treating a subject who is a child under two years of age, or a subject with asthma, COPD or immunodeficiency, or a subject who is elderly or in long term care facilities. In one embodiment, the compounds of the present invention are for use in treating a subject suffers from chronic lung disease. In addition, the compounds of the present invention are for use in preventing RSV infections.

Additionally, the present invention provides (1) a compound of the present invention for use as a medicament; (2) the use of a compound of the present invention for the preparation of a medicament for treating RSV infection.

The compounds of Formula I, IA, IB and IC can be prepared by the procedures described in the following sections.

The invention also relates to methods of making the compositions of the invention. The compositions are prepared by any of the applicable techniques of organic synthesis. Many such techniques are well known in the art. However, many of the known techniques are elaborated in Compendium of Organic Synthetic Methods (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. 5 Wade, Jr., 1984; and Vol. 6, Michael B. Smith; as well as March, J., Advanced Organic Chemistry, Third Edition, (John Wiley & Sons, New York, 1985), Comprehensive Organic Synthesis. Selectivity. Strategy & Efficiency in Modern Organic Chemistry. In 9 Volumes, Barry M. Trost, Editor-in-Chief (Pergamon Press, New York, 1993 printing). A number of exemplary methods for the preparation of the compositions of the invention are provided below. These methods are intended to illustrate the nature of such preparations and are not intended to limit the scope of applicable methods. Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product. Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions. Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions). Standard synthetic techniques such as azeotropic removal of reaction by-products and use of anhydrous reaction conditions (e.g., inert gas environments) are common in the art and will be applied when applicable. The terms "treated", "treating", "treatment", and the like, when used in connection with a chemical synthetic operation, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two. For example, treating indicates the reasonable and usual manner in which organic chemicals are allowed to react. Normal concentrations (0.01M to 10M, typically 0.1M to 1M), temperatures (−100° C. to 250° C., typically −78° C. to 150° C., more 10 typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis are used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art. Modifications of each of the exemplary schemes and in the examples (hereafter "exemplary schemes") leads to various analogs of the specific exemplary materials produce. The above-cited citations describing suitable methods of organic synthesis are applicable to such modifications. In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography. Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation. A single stereoisomer, e.g., an enantiomer, substantially free of its stereoisomer may be obtained by resolution of the racemic mixture using a method such as formation of diastereomers using optically active resolving agents (Stereochemistry of Carbon Compounds, (1962) by E. L. Eliel, McGraw Hill; Lochmuller, C. H., (1975) *J Chromatogr.*, 113, 3) 283-15 302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stercoisomers, and (3) separation of the substantially pure or enriched stereoisomers directly under chiral conditions. Under method (1), diastereomeric salts can be formed by reaction of enantiomerically pure chiral bases such as brucine, quinine, ephedrine, strychnine, a-methyl-3-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts. Alternatively, by method (2), the substrate to be resolved is reacted with one enantiomer of a chiral compound to form a diastereomeric pair (Biel, E. and Wilen, S. (1994) 30 Stereochemistry of Organic Compounds, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester, e.g., (–) menthyl chloroformate in the presence of base, or Mosher ester, u-methoxy-a-(trifluoromethyl)phenyl acetate (Jacob I1. (1982), *J. Org. Chem.* 47:4165), of the racemic mixture, and analyzing the NMR spectrum for the presence of the two atropisomeric diastereomers. Stable diastereomers of atropisomeric compounds can be separated and isolated by normal- and reverse-phase chromatography following methods for separation of atropisomeric naphthyl-isoquinolines (Eloye, T., WO 96/15111). A racemic mixture of two enantiomers can be separated by chromatography using a chiral stationary phase (Chiral Liquid Chromatography 10 (1989) W. J. Lough, Ed. Chapman and Hall, New York; Okamoto, (1990) *J. of Chronatogr.* 513:375-378).

General Scheme of Making Compound of the Invention

Scheme 1 below outlines the general synthesis of the compounds in this invention. The benzazepin carboxylate (R=H or R=Br) 1.1 was prepared according to procedures reported (Peesapati, V.; Lingaiah, N.; OPPIAK; Organic Preparations and Procedures International; English; 25; 5; 1993; 602-606; ISSN: 0030-4948 and Heterocycles, 2005, 66, p481-502). The carboxylate functionality can be activated with a reagents such as Carbonyl diimidazole, benzotriazol-1-yl-oxytripyrrolidinophosphonium hexafluorophosphate, 2-(1H-7-Azabenzotriazol-1-yl)-1,1,3,3-tetramethyl uranium hexafluorophosphate methanaminium and the like to affect to formation of an amide bond upon reaction with a desired amine, to provide 1.2. The aniline product 1.2 is then reacted with a similarly activated carboxylic acid, preferably in the form of a carboxylic acid halide or the like, to form intermediate 1.3. Reduction of the nitro compound can be accomplished with a wide range of reagents and conditions, such a low valent metals (Pd, Fe, Zn) in the absence or presence of hydrogen or other reducing agents known in the literature to provide aniline 1.4. The third amide bond to prepare compound 1.5 is then introduced in a similar fashion as in the preparation of intermediate 1.3. Some example compounds 1.5 can then be further manipulated through Installation of additional groups, e.g. amines to generate, for example 1.6. This can be accomplished either via a SN-1(Ar)-type of reaction (heating in the presence of the desired amine in a polar erotic or aprotic solvent) or via a transition metal catalyzed reaction (see Buchwald-, Ullman-type couplings or the similar).

Scheme 1

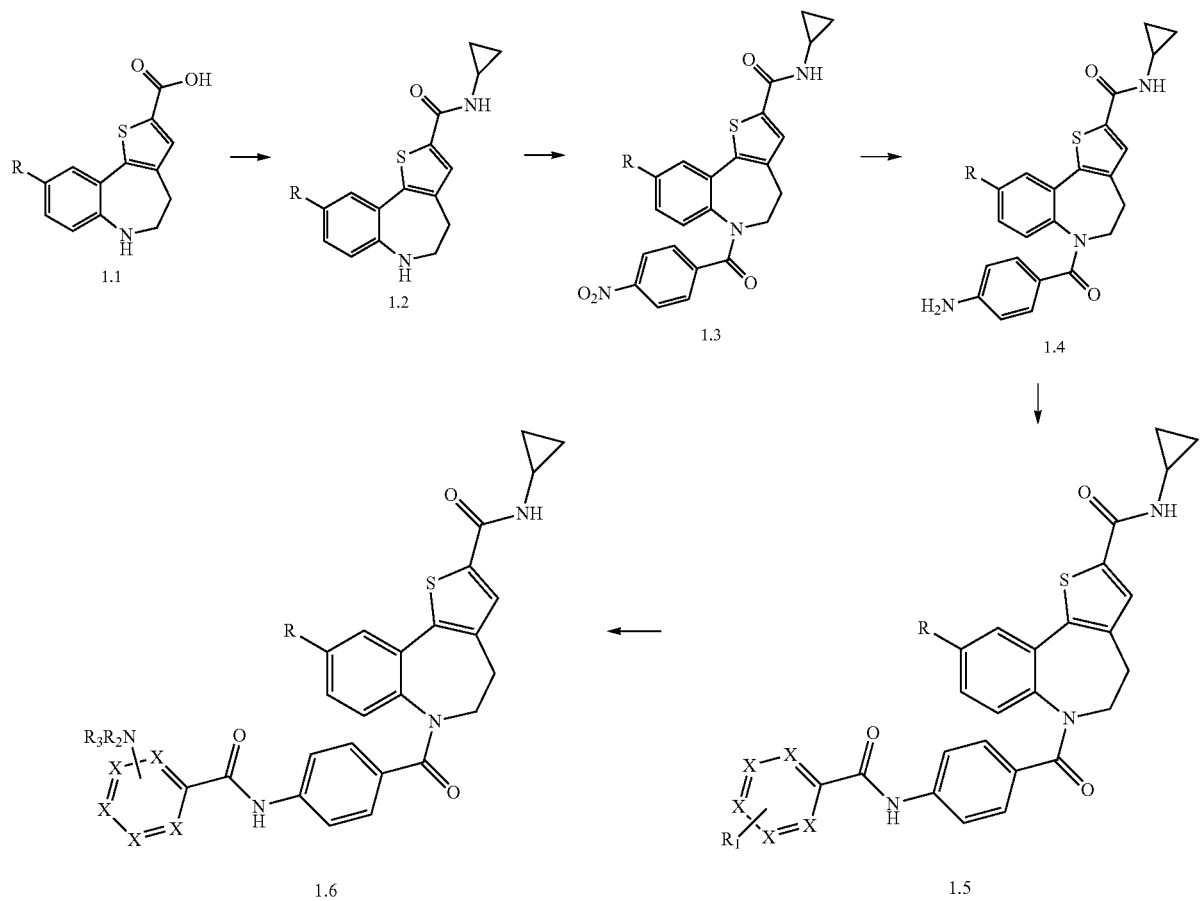

In another aspect, the present invention provides a pharmaceutical composition comprising a compound of the present invention and a pharmaceutically acceptable carrier. The pharmaceutical composition can be formulated for particular routes of administration such as intravenous administration, oral administration, parenteral administration, an intranasal administration, an intrabronchial administration, and rectal administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers etc.

The pharmaceutical compositions contain a therapeutically effective amount of a compound of the invention as defined above, either alone or in combination with one, two or three or more therapeutic agents, e.g., each at an effective therapeutic dose as reported in the art. In one embodiment, the compound of the present invention can be used in combination with an anti-inflammatory agent. Non-limiting examples of such anti-inflammatory agent include for example, salicylic acid, acetylsalicylic acid, methyl salicylate, diflunisal, salsalate, olsalazine; sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide; leukotriene antagonists including, but not limited to, zileuton, aurothioglucose, gold sodium thiomalate and auranofin; and other anti-inflammatory agents including, but not limited to, colchicine, allopurinol, probenecid, sulfinpyrazone and benzbromarone.

In one embodiment, the compound of the present invention can be used in combination with another anti-viral agent, such as an anti-influenza agent. Non-limiting examples of such anti-viral agent include nucleoside analogs, such as zidovudine, acyclovir, gangcyclovir, vidarabine, idoxuridine, trifluridine, and ribavirin, as well as foscarnet, amantadine, rimantadine, saquinavir, indinavir, ritonavir, and the alpha-interferons. Additionally, another anti-viral agent can function on a different target molecule involved in viral replication, or prevent or reduce the occurrence of viral resistance.

In one embodiment, the compound of the present invention can be used in combination with another anti-RSV agent, e.g., nucleoside analogs such as Ribavarin, monoclonal antibodies such as Synagis® (palivizumab), and antisense oligonucleotides or other small molecule inhibitors of RSV.

In one embodiment, the compound of the present invention can be used in combination with supportive care, such as of humidified oxygen and respiratory assistance, etc.

A compound of the present invention may be administered either simultaneously, before or after the other active ingredient, either separately by the same or different route of administration or together in the same pharmaceutical formulation.

Furthermore, the combinations as described above can be administered to a subject via simultaneous, separate or sequential administration (use). Simultaneous administration (use) can take place in the form of one fixed combination with two or three or more active ingredients, or by simultaneously administering two or three or more compounds that are formulated independently. Sequential administration (use) preferably means administration of one (or more) compounds or active ingredients of a combination at one time point, other compounds or active ingredients at a different time point, that is, in a chronically staggered manner, preferably such that the combination shows more efficiency than the single compounds administered independently (especially showing synergism). Separate administration (use) preferably means administration of the compounds or active ingredients of the combination independently of each other at different time points, preferably meaning that two, or three or more compounds are administered such that no overlap of measurable blood levels of both compounds are present in an overlapping manner (at the same time).

Also combinations of two or three or more of sequential, separate and simultaneous administrations are possible, preferably such that the combination compound-drugs show a joint therapeutic effect that exceeds the effect found when the combination compound-drugs are used independently at time intervals so large that no mutual effect on their therapeutic efficiency can be found, a synergistic effect being especially preferred.

The pharmaceutical composition or combination of the present invention can be in unit dosage of about 1-1000 mg of active ingredients for a subject of about 50-70 kg, preferably about 5-500 mg of active ingredients, preferably about 0.1-100 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

In another aspect, the activities of the compounds of the present invention can be assessed by the following assays.

Antiviral activity against RSV was determined using an in vitro cytoprotection assay in Hep2 cells. In this assay, compounds inhibiting the virus replication exhibit cytoprotective effect against the virus-induced cell killing that can be quantified using a cell viability reagent. The method used is similar to methods previously described in Chapman J et al., "RSV604 a novel inhibitor of respiratory syncytial virus replication," *Antimicrob Agents Chemother,* 51(9):3346-53 (2007).

Hep2 cells were obtained from ATCC (Manassas, Va.) and maintained in MEM media supplemented with 10% fetal bovine serum and penicillin/streptomycin. Cells were passaged twice a week and kept at subconfluent stage. Commercial stock of RSV strain A2 (Advanced Biotechnologies, Columbia, Md.) was titered before compound testing to determine the appropriate dilution of the virus stock that generates desirable cytopathic effect in Hep2 cells.

For antiviral tests, Hep2 cells were seeded into 96-well plates 24 hours before the assay at a density of 3,000 cells/well. On a separate 96well plate, tested compounds were serially diluted in cell culture media. Eight concentrations in 3-fold serial dilution increments were prepared for each tested compound and 100 uL/well of each dilution was transferred in duplicate onto plates with seeded Hep2 cells. Subsequently, appropriate dilution of virus stock previously determined by titration was prepared in cell culture media and 100 uL/well was added to test plates containing cells and serially diluted compounds. Each plate included three wells of infected untreated cells and three wells of uninfected cells that served as 0% and 100% virus inhibition control, respectively. Following the infection with RSV, testing plates were incubated for 4 days in a tissue culture incubator. After the incubation, RSV-induced cytopathic effect was determined using a Cell TiterGlo reagent (Promega, Madison, Wis.) followed by a luminescence read-out. The percentage inhibition was calculated for each tested concentration relative to the 0% and 100% inhibition controls and the EC50 value for each compound was determined by non-linear regression as a concentration inhibiting the RSV-induced cytopathic effect by 50%. Ribavirin (purchased from Sigma, St. Louis, Mo.) was used as a positive control for antiviral activity.

Cytotoxicity of tested compounds was determined in uninfected Hep2 cells in parallel with the antiviral activity using the cell viability reagent in a similar fashion as described before for other cell types. See Cihlar, T. et al., "Design and profiling of GS-9148, a novel nucleotide analog active against nucleoside-resistant variants of human immunodeficiency virus type 1, and its orally bioavailable phosphonoamidate prodrug, GS-9131," *Antimicrob Agents Chemother,* 52(2): 655-65 (2008). Same protocol as for the determination of antiviral activity was used for the measurement of compound cytotoxicity except that the cells were not infected with RSV. Instead, fresh cell culture media (100 uL/well) without the virus was added to tested plates with cells and prediluted compounds. Cell were then incubated for 4 days followed by a cell viability test using CellTiter Glo reagent and a luminescence read-out. Untreated cell and cells treated with 50 ug/mL puromycin (Sigma, St. Louis, Mo.) were used as 100% and 0% cell viability control, respectively. The percent of cell viability was calculated for each tested compound concentration relative to the 0% and 100% controls and the CC50 value was determined by non-linear regression as a compound concentration reducing the cell viability by 50%.

Table 1 below shows that the compounds of the present invention inhibit RSV. Those compounds that show at least 60% greater inhibition have a EC50 value in the range of 1 nM to 1 μM.

TABLE 1

Activities of Compounds

| Final compound of Example | RSV % inh. @ 1 uM |
|---|---|
| 1 | 76 |
| 2 | 78 |
| 3 | 100 |
| 4 | 78 |
| 5 | 79 |
| 6 | 100 |
| 7 | 100 |
| 8 | 100 |
| 9 | 100 |
| 10 | 100 |
| 11 | 99 |
| 12 | 97 |
| 13 | 99 |
| 14 | 100 |
| 15 | 97 |

TABLE 1-continued

Activities of Compounds

| Final compound of Example | RSV % inh. @ 1 uM |
|---|---|
| 16 | 0 |
| 17 | 100 |
| 18 | 98 |
| 19 | 100 |
| 20 | 99 |
| 21 | 94 |
| 22 | 90 |
| 23 | 93 |
| 24 | 78 |
| 25 | 64 |
| 26 | 47 |
| 27 | 41 |
| 28 | 15 |
| 29 | 22 |
| 31 | 30 |
| 34 | 90 |
| 37 | 100 |
| 38 | 99 |
| 39 | 94 |
| 40 | 98 |
| 41 | 99 |
| 42 | 99 |
| 43 | 99 |
| 44 | 77 |
| 45 | 100 |
| 46 | 98 |
| 47 | 100 |
| 48 | 100 |
| 49 | 30 |
| 50 | 100 |
| 51 | 46 |
| 52 | 100 |
| 53 | 1 |
| 54 | 99 |
| 55 | 16 |
| 56 | 93 |
| 57 | 95 |
| 58 | 100 |
| 59 | 43 |
| 60 | 35 |
| 61 | 84 |
| 62 | 90 |
| 63 | 99 |
| 64 | 99 |
| 65 | 95 |
| 66 | 100 |
| 67 | 98 |

ABBREVIATIONS

AcOH Acetic acid
ATCC American Type Culture Colection
C carbon
$CH_3CN$ Acetonitrile
$Cs_2CO_3$ Cesium carbonate
CuI Copper iodide
DMAP dimethylaminopyridine
DME Dimethoxyethane
DIPEA diisopropylethylamine
DMF dimethylformamide
DMSO dimethylsulfoxide
dt doublet of triplets
Et ethyl
EtOAc Ethyl acetate
EtOH Ethanol
EDTA ethylenediaminetetraacetic acid
FAB fast atom bombardment
gem geminal
HATU 2-(1H-7-Azabenzotriazol-1-yl)-1,1,3,3-tetramethyl uronium hexafluorophosphate Methanaminium
$H_2$ hydrogen gas
HBr hydrobromic acid
HCl hydrochloric acid
HPLC high performance liquid chromatography
HR high resolution
ipso
IR infrared spectroscopy
m multiplet
m meta
Me methyl
MeOH methanol
MeONa sodium methoxide
MS mass spectrometry
ν wave number
$N_2$ nitrogen gas
$NaHCO_3$ sodium bicarbonate
NaOH sodium hydroxide
$Na_2SO$ Sodium sulfate
$NEt_3$ triethylamine
$NH_4OH$ ammonium hydroxide
NMR nuclear magnetic resonance
ortho
p para
Pd Palladium
$POCl_3$ phosphorus oxychloride
Ph phenyl
$PPh_3$ triphenylphosphine
Py pyridyl
pyrr pyrrolyl
PyBroP Bromo-tris-pyrrolidino phosphoniumhexafluorophosphate
q quartet
rel. relative
RT room temperature
s singlet
sat. saturated
sol. solution
t triplet
TBS tert-butyldimethylsilyl
td triplet of doublets
TDA-1 tris[2-(2-methoxyethoxy)ethyl]amine
THF tetrahydrofuran
TFA trifluoroacetic acid
TPPTS sodium triphenylphosphine trisulfonate
Tr trityl, triphenylmethyl
vic vicinal
HPLC high-pressure liquid chromatography
FBS fetal bovine serum
RPMI Royal Park Memorial Institute
TCA trichloroacetic acid
DIAD di-isopropyl azaodicarboxylate
PyBOP benzotriazol-1-yl-oxytripyrrolidinophosphonium hexafluorophosphate
DME dimethoxyethane

EXAMPLES

The following examples are intended to illustrate the invention and are not to be construed as being limitations thereon.

Intermediate A

The synthesis of intermediate A has been reported in Heterocycles, 2005, 66, p481-502 and the method described below was based on the methods cited in this reference.

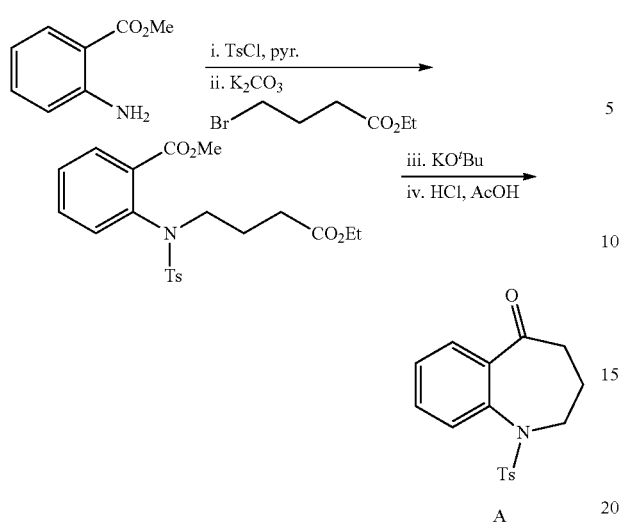

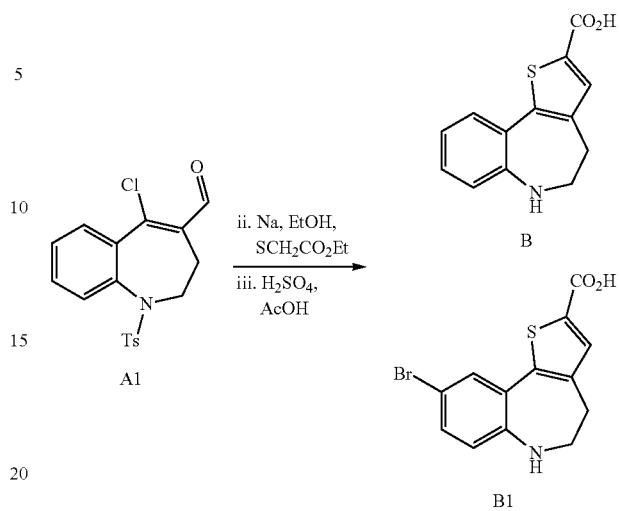

Step (i): 2-amino benzoic acid methyl ester (330 g) was dissolved in dichloromethane (1 L) and treated with pyridine and tosyl chloride (1.1 equiv). The mixture was stirred for 4 h and then washed with 1N HCl (aq), followed by brine, dried over magnesium sulfate and concentrated. The residue was purified using silica gel chromatography to isolate the tosylated product.

Step (ii): The tosylated product from step (i) (330 g) and potassium carbonate (520 g) were added to n-butanone (1.5 L) and treated with 4-bromobutyric acid ethyl ester (234 g). The mixture was stirred overnight and then concentrated under reduced pressure to give a crude product. The crude product was combined with another equivalent batch prepared in parallel.

Step (iii): Crude product from step (ii) (1100 g) was added to toluene (2 L). The mixture was treated with potassium t-butoxide (800 g) and stirred overnight. The mixture was washed with 1N HCl, followed by brine, and dryied over magnesium sulfate. The organic solution was concentrated under reduced pressure to provide crude product.

Step (iv): The crude product from step (iii) was treated with 6N HCl (1.5 L) and AcOH (3.5 L) and stirred overnight. The solution was washed with dichloromethane several times and the combined organic washes, washed with brine, dried over magnesium sulfate and concentrated. The residue was chromatographed on silica gel to isolate intermediate A.

Intermediate B

The preparation of intermediate B from Intermediate A was described in Organic Preparations and Procedures International, 1993, 25, p602-606

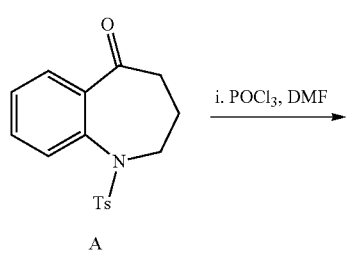

Step (i): $POCl_3$ (3.0 eq) was added to dry DMF and cooled in an ice bath. Then the solution of compound A (20 g) in dry DMF was added into the mixture. The mixture was stirred 1 h at room temperature and then refluxed for 4 h. The solution was added to ice water and saturated NaOAc aqueous solution added until the pH was neutral. The mixture was extracted with ethyl acetate (500 mL×3). The combined organic layers were washed with water, saturated $NaHCO_3$ solution, brine and dried over anhydrous $NaSO_4$. The mixture was filtered and concentrated under reduced pressure to provide 15 g of crude aldehyde A1

Step (ii) Metal sodium (2.0 eq based on A1) was dissolved in ethanol and cooled with an ice bath. Ethyl 2-mercaptoacetate was added to the solution and after 30 min, aldehyde A1 (15 g) was added. The mixture was kept around 0° C. for 30 min and then refluxed for 3 h. The mixture was cooled and 2N HCl aqueous solution added to adjust the pH to neutral. The mixture was then extracted with ethyl acetate and the organic layer, washed with water, saturated $NaHCO_3$ aqueous solution and saturated NaCl aqueous solution. The organic layer was dried over anhydrous $NaSO_4$, filtered and concentrated under reduced pressure to obtain a crude product (13 g) which was moved to step (iii).

Step (iii). The crude product from (ii) was dissolved in HBr in acetic acid (200 mL) and boiled. Sulfuric acid (50%, v/v 100 mL) was added dropwise to the boiling mixture and heating continued for another 6 h. The solution was cooled and concentrated to a crude residue. The residue was chromatographed over silica gel to provide intermediate B and intermediate B1.

$^1$H-NMR of B (DMSO, 300 MHz): δ 7.47 (d, J=7.8 Hz, 1H), 7.42 (s, 1H), 6.97 (d, J=8.1 Hz, 1H), 6.72 (d, J=8.4 Hz, 1H), 6.72 (d, J=8.4 Hz, 1H), 6.60 (s, 1H), 3.23-3.20 (m, 2H), 2.94-2.90 (m, 2H).

$^1$H-NMR of B1 (DMSO, 300 MHz): 7.51 (s, 1H), 7.43 (s, 1H), 7.11 (d, J=8.1 Hz, 1H), 6.69 (d, J=8.4 Hz, 1H), 6.61 (s, 1H), 3.1 (m, 2H), 2.3 (m, 2H).

Intermediate C

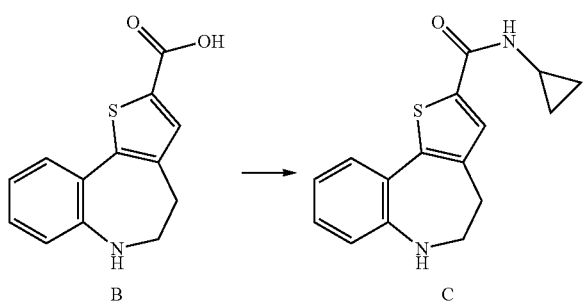

To a solution of the acid B (2.5 g, 0.01 M) in dry pyridine (10 mL) was added cyclopropylamine (5.8 g, 0.1 M) and stirred under N₂. HATU (4.56 g, 0.012 M) was added portion wise and the solution stirred for 16 h at RT under N₂. Volatiles were removed under reduced pressure at 40° C. The resulting residue was dissolved in EtOAc (200 mL), the organic phase was washed 2× each with aqueous dilute NaHCO₃, then H₂O followed by brine. Volatiles were removed under reduced pressure at 40° C. and the resulting residue was purified by silica gel column using 50% EtOAc in hexanes with a gradient from 50% to 100% to afford the product C (2.73 g, 96%) as a yellow oil.

$^1$H-NMR (DMSO, 300 MHz): δ 8.63 (d, J=4.5 Hz, 1H), 7.65 (t, J=7.5 Hz, 1H), 7.30 (s, 1H), 7.06 (t, J=8.4 Hz, 1H), 6.80 (t, J=8.1 Hz, 1H), 6.66 (d, J=8.1 Hz, 1H), 6.13 (s, 1H), 3.42 (d, J=5.1 Hz, 2H), 3.05 (d, J=5.4 Hz, 2H), 2.89 (m, 1H), 0.86 (m, 1H), 0.63 (m, 1H).

LC-MS m/z [M+H]⁺ $C_{16}H_{16}N_2OS$ requires: 284.38. Found 285.02.

HPLC Tr (min), purity %: 3.27, 95%.

Intermediate D

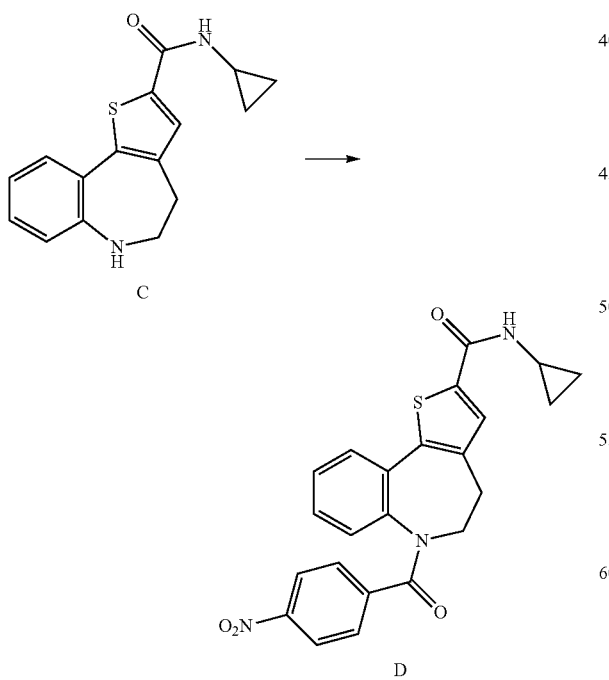

To a solution of the amine C (1.5 g, 5.3 mM) in dry pyridine (10 mL) was added slowly a solution of p-nitrobenzoyl chloride (0.97 g, 5.3 mM) in CH₃CN (10 mL) and stirred under N₂ at RT for 2 h. Volatiles were removed under reduced pressure at 40° C., the resulting residue dissolved in EtOAc (150 mL) and the organic phase was washed 2× each with aqueous dilute NaHCO₃, then H₂O followed by brine. Volatiles were removed under reduced pressure at 40° C., the resulting residue was purified by silica gel column using 50% EtOAc in hexanes with a gradient from 50% to 100% EtOAc to afford intermediate D (1.47 g, 65%) as a yellow oil.

$^1$H-NMR (DMSO, 300 MHz): δ 8.50 (d, J=4.2 Hz, 1H), 7.99 (d, J=8.7 Hz, 2H), 7.71 (d, J=8.1 Hz, 1H), 7.62 (s, 1H), 7.23-7.16 (m, 3H), 7.00 (t, J=8.4 Hz, 1H), 6.87 (d, J=7.5 Hz, 1H), 4.83-4.78 (m, 1H), 3.29-3.16 (m, 2H), 3.06-3.01 (m, 1H), 2.79-2.73 (m, 1H), 0.66-0.58 (m, 2H), 0.53-0.48 (m, 2H).

LCMS m/z [M+H]⁺ $C_{23}H_{19}N_3O_4S$ requires: 433.11. Found 433.97.

HPLC Tr (min), purity %: 3.88, 90%

Intermediate E

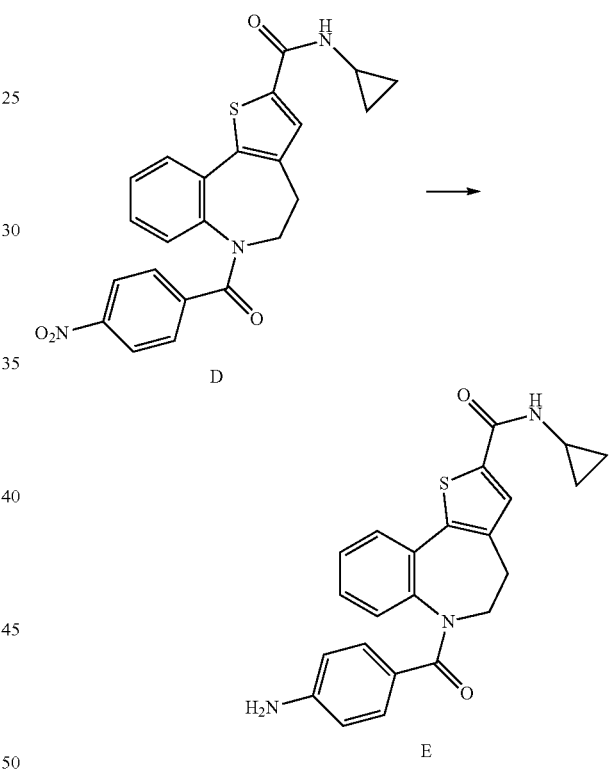

Intermediate D (1.47 g, 3.4 mM) was dissolved in hot EtOH (100 mL) and 1N HCl (5 mL) and cooled to RT. Pd/C (10%, 150 mg) was added under N₂ and H₂ bubbled through the suspension for 20 min. The suspension was then stirred under H₂ (balloon) for 2 h. After flushing with N₂, the suspension was filtered and the volatiles removed under reduced pressure to afford intermediate E (1.32 g, 97%) as an off-white powder.

$^1$H-NMR (DMSO, 300 MHz): δ 8.53 (d, J=3.9 Hz, 1H), 7.75 (d, J=7.8 Hz, 1H), 7.64 (s, 1H), 7.23 (t, J=7.5 Hz, 1H), 7.07 (t, J=6.3 Hz, 1H), 6.82-6.78 (m, 2H), 6.48 (d, J=7.8 Hz, 2H), 3.22 (mc, 4H), 2.79 (mc, 1H), 0.70-0.68 (m, 2H), 0.57-0.55 (m, 2H).

LCMS m/z [M+H]⁺ $C_{23}H_{21}N_3O_2S$ requires: 403.14. Found 404.07.

HPLC Tr (min), purity %: 3.18, 95%

Intermediate F

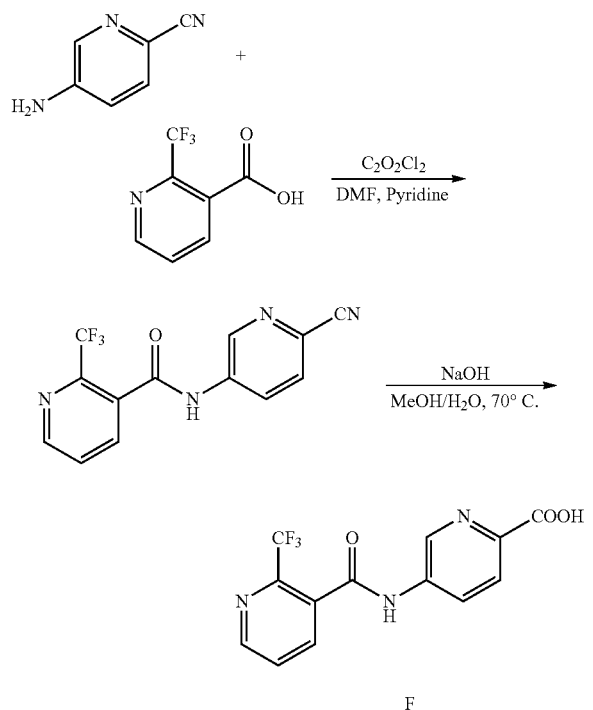

To a 50 mL flask containing 20 mL of DMF was added 1 mL of oxalyl chloride slowly and stirred for 10 min at RT. 100 mg of 2-trifluoromethyl nicotinic acid was dissolved in 2 mL of the above solution and stirred for 5 min at RT. Then 50 mg of 2-cyano-5-aminopyridine was dissolved in 1 mL pyridine and added to the above solution. The reaction was completed in 5 min at RT and quenched with 1 mL $NH_4OH$. The solvent was then evaporated under vacuum and the residue was used directly in the next step. The nitrile was dissolved in methanol (10 mL) and water (10 mL). Sodium hydroxide (300 mg) was added to the above solution and the solution heated at 70° C. for 16 h. The reaction mixture was quenched with 1N HCl (10 mL), and extracted with EtOAc four times (15 mL). Volatiles were evaporated and the intermediate F used without further purification in the next steps.

Intermediate G,

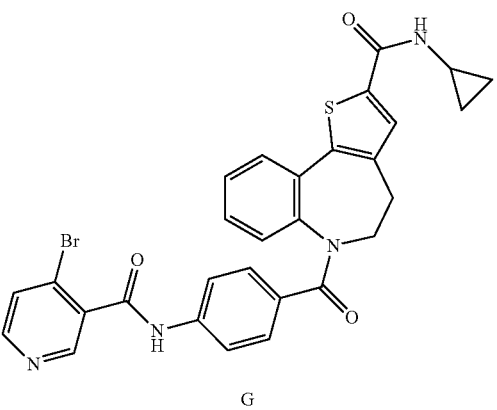

To a 50 mL flask containing 20 mL of DMF was added 1 mL of oxalyl chloride slowly and stirred for 10 min at RT. The 4-bromo nicotinic acid (100 mg) was added to 2 mL of the above solution and stirred for 5 min at RT. Aniline E (50 mg) was dissolved in pyridine (1 mL) and added to the solution. The reaction was completed in 5 min at RT and quenched with 1 mL $NH_4OH$. The solvent was then evaporated under vacuum and the residue dissolved in $CH_3CN$ and water and purified with prep HPLC (0% to 95% water/$CH_3CN$) to afford intermediate G (31 mg, 44%).

$^1$H-NMR (DMSO, 300 MHz): δ 8.90 (s, 1H), 8.44 (d, J=3.3 Hz, 1H), 7.71 (t, J=7.5 Hz, 1H), 7.65 (d, J=8.7 Hz, 1H), 7.41 (t, J=8.1 Hz, 1H), 7.27 (s, 1H), 7.12 (d, J=7.5 Hz, 2H), 7.06-7.01 (m, 2H), 6.80 (s, 1H), 6.67 (d, J=7.5 Hz, 1H), 5.20 (s, 1H), 4.81 (d, J=8.1 Hz, 1H), 3.24-3.11 (m, 3H), 2.92 (d, J=12.3 Hz, 1H), 2.82 (s, 1H), 0.89-0.82 (m, 2H), 0.65 (m, 2H).

LCMS m/z [M+H]$^+$ $C_{29}H_{23}BrN_4O_3S$ requires: 587.07. Found 587.56.

HPLC Tr (min), purity %: 3.37, 98%

Intermediate H

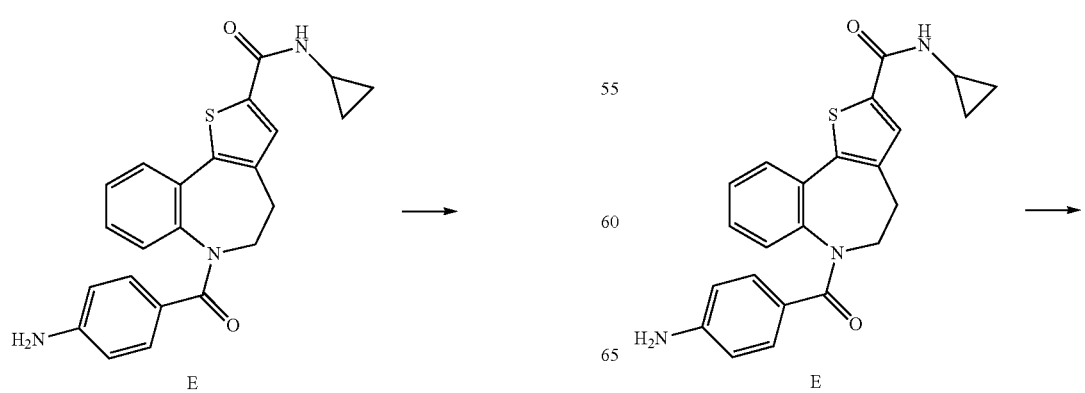

-continued

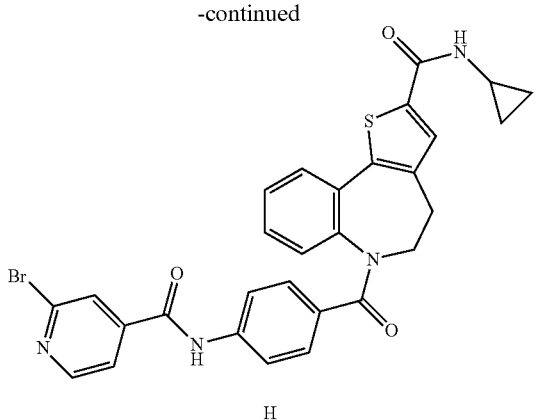

H

To a 50 mL flask containing 20 mL of DMF was added 1 mL of oxalyl chloride slowly and stirred for 10 min at RT. 2-Bromo-isonicotinic acid (100 mg) was added to 2 mL of the above solution and stirred for 5 min at RT. Aniline E (50 mg) was dissolved in pyridine (1 mL) and added to the above solution. The reaction was completed in 5 min at RT and quenched with 1 mL NH$_4$OH. The solvent was then evaporated under vacuum and the residue dissolved in CH$_3$CN and water and purified with prep HPLC (0% to 95% water/CH$_3$CN) to afford intermediate H (32 mg, 43%).

$^1$H-NMR (DMSO, 300 MHz): δ 8.91 (s, 1H), 8.43 (d, J=3.3 Hz, 1H), 7.74 (d, J=7.5 Hz, 1H), 7.64 (d, J=8.5 Hz, 1H), 7.45 (d, J=8.1 Hz, 1H), 7.23 (s, 1H), 7.15 (d, J=7.5 Hz, 2H), 7.12-7.04 (m, 2H), 6.68 (s, 1H), 6.54 (d, J=7.5 Hz, 1H), 5.22 (s, 1H), 4.76 (d, J=8.1 Hz, 1H), 3.34-3.15 (m, 3H), 2.97-2.91 (m Hz, 1H), 2.81 (s, 1H), 0.91-0.84 (m, 2H), 0.65 (m, 2H).

LCMS m/z [M+H]$^+$ C$_{29}$H$_{23}$BrN$_4$O$_3$S requires: 587.07. Found 587.45.

HPLC Tr (min), purity %: 3.33, 98%

Intermediate J

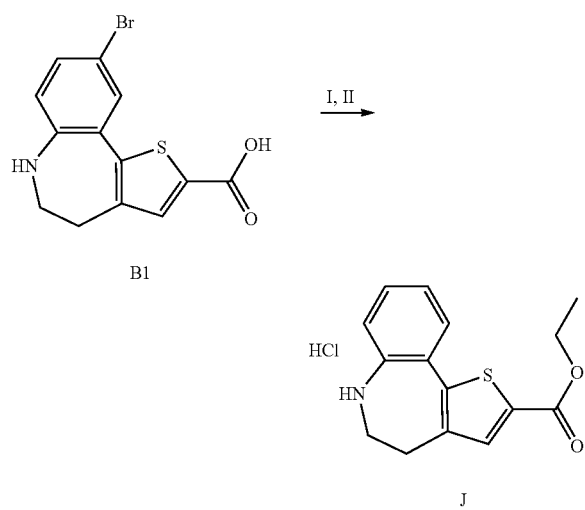

I. SOCl$_2$, EtOH, 70° C.; II. EtOH, Pd/C, H$_2$

Mixed B1 (648 mg, 2 mmol) with EtOH (40 mL). Thionyl chloride (1.5 mL, 20 mmol) was added dropwise over 10-15 mins. The reaction mixture was then stirred at 70° C. for 16 hrs. The mixture was concentrated under reduced pressure to give a solid which was then suspended in hexanes and stirred for 30 mins. The solid was collected by filtration, washed with hexanes, and dried under high vacuum. The solid was dissolved in EtOH (50 mL). 5% Pd/C was added and the mixture stirred under 1 atm of H$_2$ for 3 hrs. The mixture was filtered through Celite and concentrated under reduced pressure to give a solid. The solid was dried under high vacuum to give (632 mg, 99%).

$^1$H NMR (300 MHz, CD$_3$OD): δ 7.80 (m, 2H), 7.59 (m, 3H), 4.39 (q, J=6.9 Hz, 2H), 3.95 (t, J=7.2 Hz, 2H), 3.09 (t, J=6.9 Hz, 2H), 1.39 (t, J=7.2 Hz, 3H).

LC/MS (m/e): 274.1 [M+H]$^+$

Intermediate K

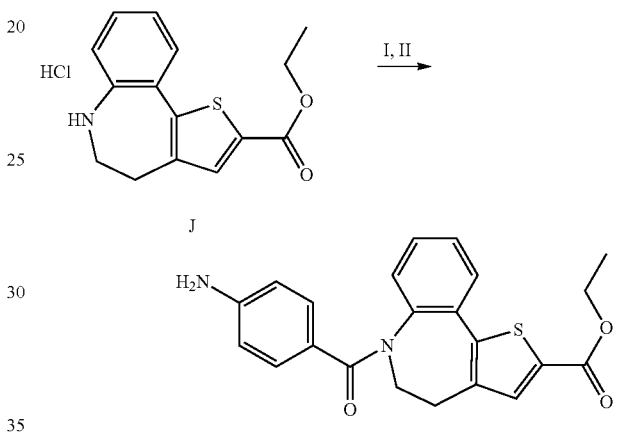

I. p-nitrobenzoyl chloride, DIPEA, DMAP, DMF, 50° C.; II. Zn, HOAc/ACN

Intermediate J (632 mg, 2 mmol) was dissolved in anhydrous DMF (20 mL). p-nitrobenzoyl chloride (197 mg, 2.68 mmol) was added followed by DIPEA (930 uL, 5.34 mmol). DMAP (44 mg, 0.35 mmol) was added and the reaction stirred at 50° C. for 4 hrs. Diluted reaction with EtOAc and washed with saturated aqueous sodium bicarbonate solution (2×), 5% aqueous citric acid solution and saturated sodium chloride solution. Dried organic extract over anhydrous sodium sulfate and concentrated under reduced pressure to give solid. Dissolved solid in acetonitrile and acetic acid. Added zinc powder and stirred for 6 hrs. Filtered off solid and washed with acetonitrile. Concentrated under reduced pressure. Dissolved in EtOAc and washed with saturated aqueous sodium bicarbonate solution (2×) and saturated sodium chloride solution. Dried organic extract over anhydrous sodium sulfate and concentrated under reduced pressure. Purified with Combiflash (0-70% EtOAc in hexanes) to give K (740 mg, 94%).

$^1$H NMR (300 MHz, CDCl$_3$): δ 7.79 (d, J=7.8 Hz, 1H), 7.67 (s, 1H), 7.20 (m, 1H), 7.04 (m, 1H), 6.99 (d, J=8.7 Hz, 2H), 6.79 (d, J=7.8 Hz, 1H), 6.41 (d, J=8.7 Hz, 2H), 5.11 (bs, 1H), 4.39 (q, J=6.9 Hz, 2H), 3.41-3.11 (m, 3H), 1.41 (t, J=7.2 Hz, 3H)

LC/MS (m/e): 393.1 [M+H]$^+$

Intermediate L

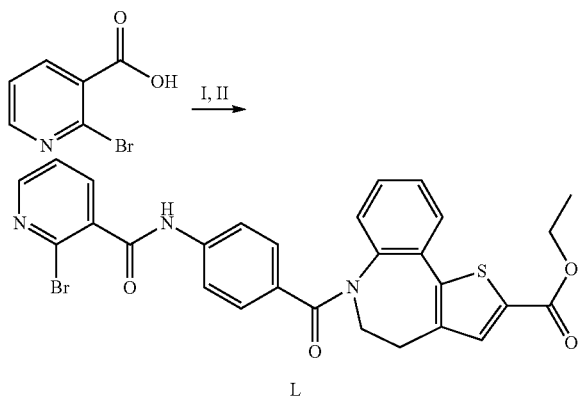

L

I. K₂CO₃, isobutyl chloroformate, THF; II. K

Dissolved 2-bromo nicotinic acid (360 mg, 1.78 mmol) in anhydrous THF. Added potassium carbonate (738 mg, 5.34 mmol) and then isobutyl chloroformate (233 uL, 1.78 mmol). Stirred for 60 mins. Added intermediate K (698 mg, 1.78 mmol) and stirred for 72 hrs. Diluted with EtOAc and washed with saturated aqueous sodium bicarbonate solution (2×) and saturated sodium chloride solution. Dried organic extract over anhydrous sodium sulfate and concentrated under reduced pressure. Purified with Combiflash (20-70% EtOAc in hexanes) to give L (465 mg, 45%).

¹H NMR (300 MHz, CDCl₃): δ 8.48 (m, 1H), 7.98 (m, 2H), 7.80 (d, J=7.8 Hz, 1H), 7.69 (s, 1H), 7.39 (m, 3H), 7.18 (m, 4H), 7.06 (m, 1H), 6.78 (d, J=7.8 Hz, 1H), 5.08 (m, 1H), 5.11 (bs, 1H), 4.40 (q, J=7.2 Hz, 2H), 3.49 (m, 1H), 3.14 (m, 2H), 1.41 (t, J=7.2 Hz, 3H)

LC/MS (m/e): 576.0 and 578.0 [M+H]⁺

Intermediate M

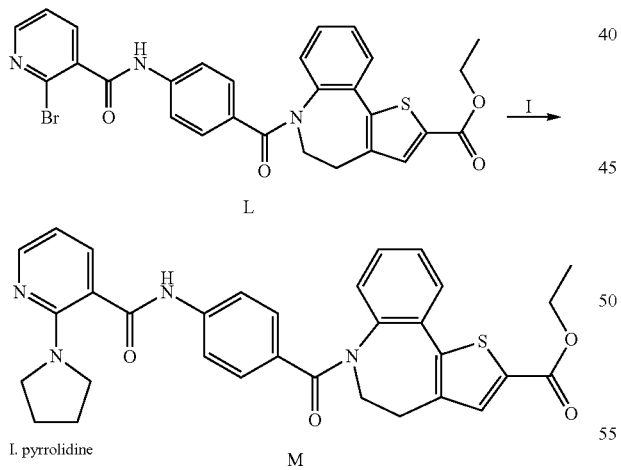

Dissolved L (460 mg, 0.8 mmol) in pyrrolidine and stirred for 16 hrs at room temperature. Concentrated under reduced pressure and purified with Combiflash (20-100% EtOAc in hexanes) to give M (214 mg, 47%).

¹H NMR (300 MHz, CDCl₃): δ 8.46 (s, 1H), 8.28 (d, J=5.1 Hz, 1H), 7.88 (d, J=7.2 Hz, 1H), 7.80 (d, J=7.8 Hz, 1H), 7.69 (s, 1H), 7.43 (m, 2H), 7.16 (m, 4H), 7.04 (m, 1H), 6.79 (m, 2H), 5.12 (m, 1H), 4.40 (q, J=7.2 Hz, 2H), 3.41 (m, 5H), 3.14 (m, 2H), 1.90 (m, 4H), 1.41 (t, J=7.2 Hz, 3H)

LC/MS (m/e): 567.1 [M+H]⁺

Intermediate N

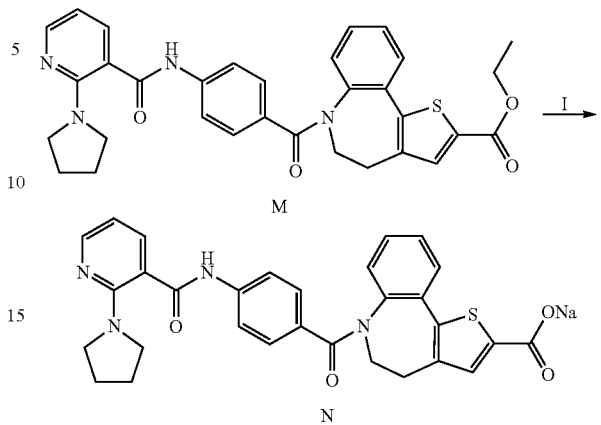

I. NaOH(aq), ACN/MeOH

Mixed M (194 mg, 0.34 mmol) in MeOH and acetonitrile. Dissolved NaOH (42 mg, 1.1 mmol) in water and added to the reaction mixture in one portion. Stirred for 6 hrs. Neutralized reaction to pH of 9 with HCl(aq) and then concentrated under reduced pressure to give yellow solid of N (quantitative) which was used without further process.

¹H NMR (300 MHz, DMSO-d₆): δ 7.82 (m, 1H), 7.70 (d, J=7.8 Hz, 1H), 7.29 (d, J=7.2 Hz, 1H), 7.18 (m, 1H), 7.07 (m, 4H), 6.75 (m, 3H), 6.36 (m, 1H), 3.41 (m, 4H), 3.04 (m, 3H), 1.72 (m, 4H).

LC/MS (m/e): 539.1 [M+H]⁺

Intermediate P

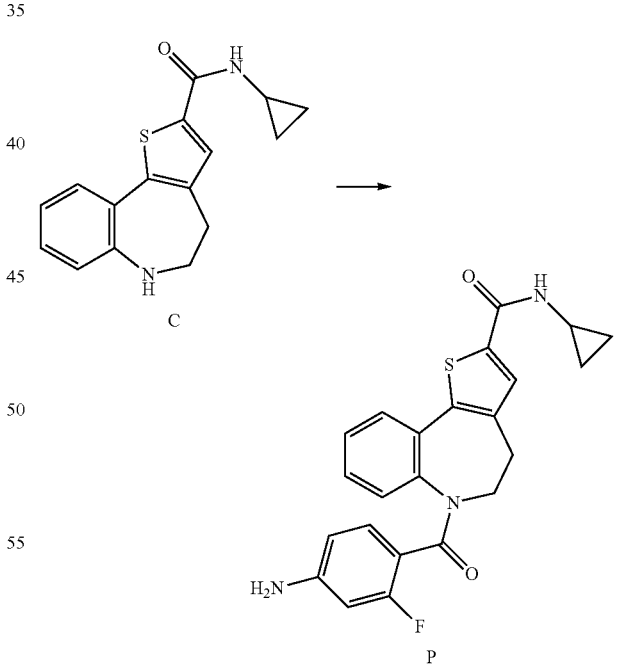

To a solution of the amine C (0.3 g, 0.1 mM) in dry pyridine (1.5 mL) was added slowly a solution of 2-Fluoro-4-nitrobenzoyl chloride (0.2 g, 0.1 mM) in CH₃CN (1 mL) and stirred under N₂ at RT fro 2 h. Volatiles were removed under reduced pressure at 40° C., the resulting residue dissolved in EtOAc (50 mL) and the organic phase was washed 2× each with aqueous dilute NaHCO₃, then H₂O followed by brine. Volatiles were removed under reduced pressure at 40° C. The resulting residue was purified by silica gel column using 50% EtOAc in hexanes with a gradient from 50% to 100% to afford the corresponding nitro intermediate (0.31 g, 64. The nitro compound was hydrogenated using Pd on C (10%, 0.2 g) in 150 mL Ethanol and 1 mL 1N HCl under an atmosphere of H₂ (balloon). Volatiles were removed under reduced pressure at 40° C. to afford P (0.31 g, 99%).

LC/MS (m/e): 522.03 [M+H]⁺

Intermediate Q

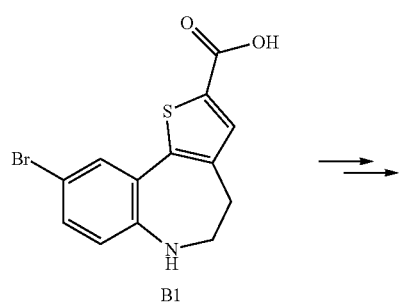

B1

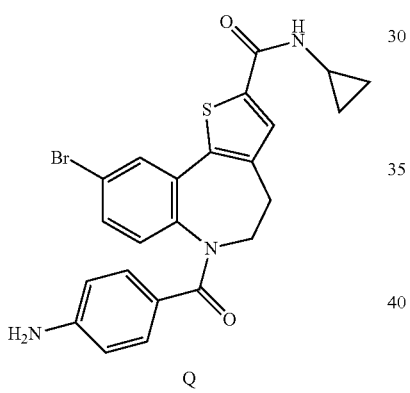

Q

Preparation of intermediate Q was performed as shown for intermediate D followed by a reduction of the nitro precursor (0.51 g) with iron powder (1.1 g) in HOAc (50 mL) at 70° C. with vigorous stirring for 5 min. Volatiles were removed under reduced pressure at 40° C., the resulting residue dissolved in EtOAc (150 mL) and the organic phase was washed 2× each with aqueous dilute NaHCO₃, then H₂O followed by brine. Volatiles were removed under reduced pressure at 40° C., the resulting residue was purified by silica gel column using 50% EtOAc in hexanes with a gradient from 50% to 100% to afford intermediate Q (0.41 g, 85%).

¹H-NMR (DMSO, 300 MHz): δ 8.55 (d, J=3.6 Hz, 1H), 7.84 (d, J=2.1 Hz, 1H), 7.64 (s, 1H), 7.27 (d, J=8.7 Hz, 1H), 6.73-6.70 (m, 3H), 6.28 (d, J=8.7 Hz, 2H), 5.52 (s, 1H), 3.10 (m, 2H), 2.49 (m, 2H), 0.70 (m, 2H), 0.56 (m, 2H).

LCMS m/z [M+H]⁺ C₂₃H₁₈BrN₃O₄S requires: 512.38. Found 513.89.

HPLC Tr (min), purity %: 2.53, 90%

Intermediate R

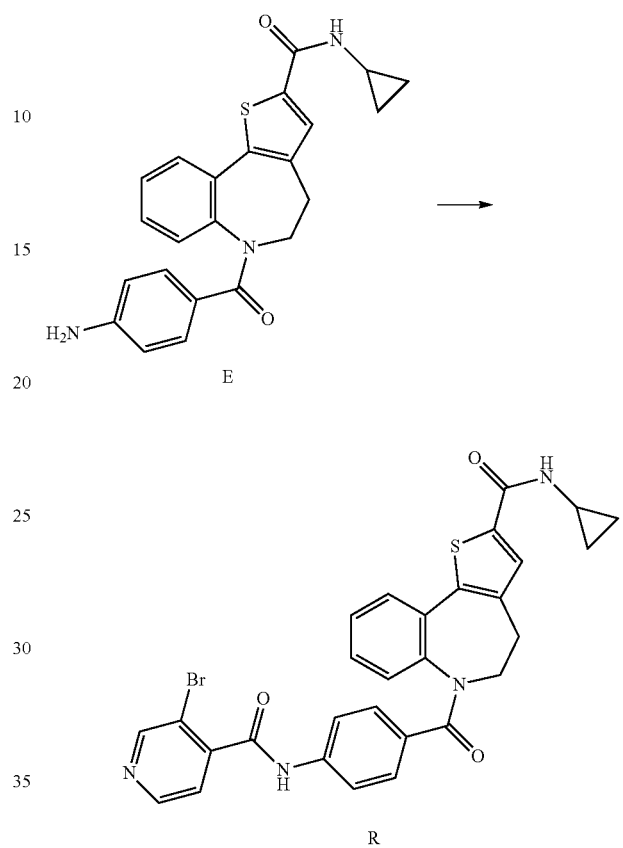

To a 50 mL flask containing 20 mL of DMF added 1 mL of oxalyl chloride slowly, an orange solution formed after the addition. 100 mg of 3-Bromo-4-Pyridinecarboxylic Acid was dissolved in 2 mL of the above orange solution and stirred for 5 mins at room temperature. Then 50 mg of the intermediate E was dissolved in 1 mL pyridine and then this pyridine solution was added to the above orange carboxylic acid solution. Reaction was finished in 5 mins at room temperature and was quenched with 1 mL NH₄OH. The solvent was then evaporated under vacuum and the residue was dissolved in CH₃CN and water and purified with prep HPLC to afford intermediate R (27 mg, 40%).

¹H-NMR (DMSO, 300 MHz): δ 8.95 (s, 1H), 8.43 (d, J=3.3 Hz, 1H), 7.76 (t, J=7.5 Hz, 1H), 7.68 (d, J=8.1 Hz, 1H), 7.40 (d, J=8.1 Hz, 1H), 7.25 (s, 2H), 7.15 (t, J=7.8 Hz, 1H), 7.07-7.02 (m, 2H), 6.82 (s, 1H), 6.67 (d, J=7.2 Hz, 1H), 5.22 (s, 1H), 4.88 (d, J=8.7 Hz, 1H), 3.28-3.12 (m, 3H), 2.95 (d, J=12.3 Hz, 1H), 2.82 (s, 1H), 0.84-0.80 (m, 2H), 0.66 (mc, 2H).

LCMS m/z [M+H]⁺ C₂₉H₂₃BrN₄O₃S requires: 587.07. Found 587.02.

HPLC Tr (min), purity %: 3.30, 98%

Intermediate S

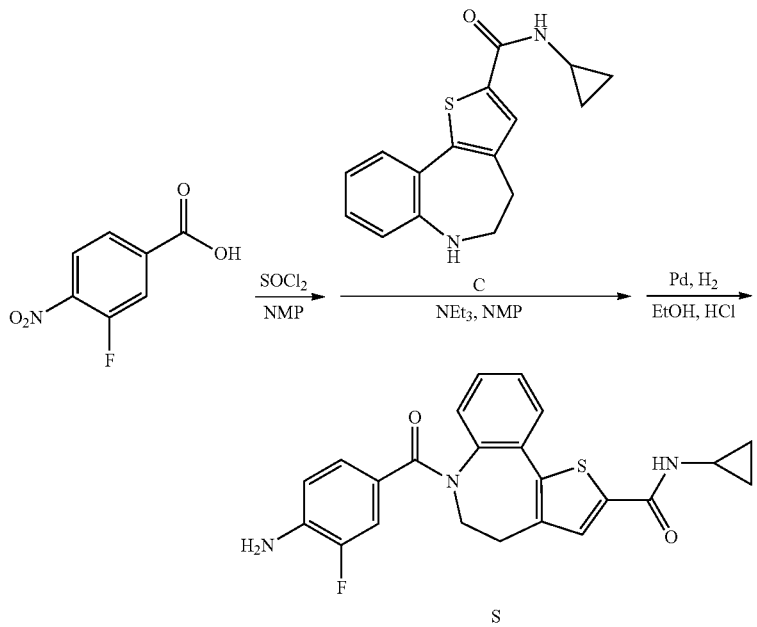

To a 10 mL flask containing 2 mL of NMP was added 100 mg of 3-Fluoro-4-Nitro, to the above solution was added 0.1 mL of Thionyl Chloride and stirred for 10 min at RT. Then 77 mg of intermediate C was dissolved in 1 mL NMP and added to the above solution followed by addition of 0.7 mL of Triethylamine. The reaction was completed in 5 min at RT and quenched with 1 mL NH$_4$OH. The solvent was then evaporated under vacuum and the residue was used directly in the next step. The nitro intermediate was dissolved in ethanol (5 mL), 0.1 mL of 1N HCl solution and 100 mg Pd—C (10%) catalyst were added and the reaction mixture was stirred under H$_2$ balloon overnight at RT. After flushing with N$_2$, the catalyst was filtered over celite and the filtrate was evaporated and purified with prep HPLC to afford intermediate S (100 mg, 88%) as an off-white powder.

$^1$H-NMR (DMSO, 300 MHz): δ 8.51 (d, J=4.2 Hz, 1H), 7.76 (d, J=6.9 Hz, 1H), 7.63 (s, 1H), 7.27 (t, J=7.2 Hz, 1H), 7.11 (t, J=7.5 Hz, 1H), 6.83 (d, J=8.4 Hz, 1H), 6.64 (d, J=12.3 Hz, 1H), 6.51-6.40 (m, 2H), 4.87 (s, 1H), 3.09 (mc, 3H), 2.79 (mc, 1H), 0.70-0.69 (m, 2H), 0.56-0.55 (m, 2H).

LCMS m/z [M+H]$^+$ C$_{23}$H$_{20}$FN$_3$O$_2$S requires: 421.49. Found 421.28.

HPLC Tr (min), purity %: 3.08, 98%

Intermediate T

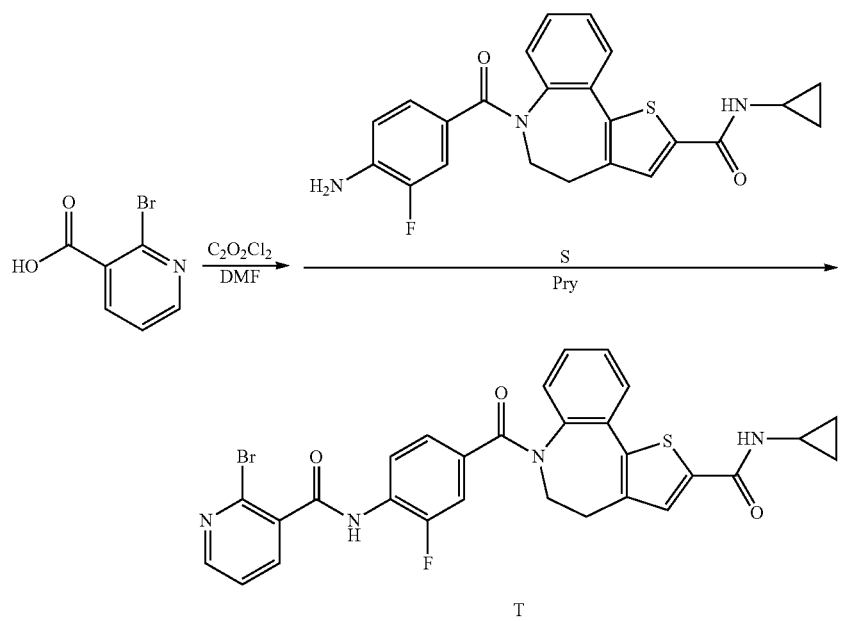

To a 20 mL flask containing 20 mL of DMF was added 1 mL of oxalyl chloride slowly. An orange solution formed after the addition. 100 mg of 2-Bromo-3-Pyridinecarboxylic Acid was dissolved in 2 mL of the above orange solution and stirred for 5 mins at room temperature. Then 50 mg of the intermediate S was dissolved in 1 mL pyridine and this pyridine solution was added to the above orange carboxylic acid solution. Reaction was finished in 5 mins at room temperature and quenched with 1 mL NH$_4$OH. The solvent was then evaporated under vacuum and the residue was dissolved in CH$_3$CN and water and purified with prep HPLC to afford intermediate T (53 mg, 74%).

$^1$H-NMR (DMSO, 300 MHz): δ 10.56 (s, 1H), 8.54 (d, J=4.2 Hz, 1H), 8.46 (d, J=4.8 Hz, 1H), 7.94 (d, J=6.3 Hz, 1H), 7.78 (d, J=7.8 Hz, 2H), 7.66 (s, 1H), 7.53 (dd, J=4.8, 7.2 Hz, 1H), 7.29 (t, J=7.8 Hz, 1H), 7.14 (t, J=4.2 Hz, 1H), 6.95-6.90 (m, 2H), 6.78 (d, J=7.5 Hz, 1H), 4.88 (d, J=8.7 Hz, 1H), 3.25-3.05 (m, 3H), 2.81-2.80 (m, 1H), 0.70 (m, 2H), 0.56 (m, 2H)

LCMS m/z [M+H]$^+$ C$_{29}$H$_{22}$BrFN$_4$O$_3$S requires: 605.48. Found 605.52.

HPLC Tr (min), purity %: 3.15, 98%

Intermediate U

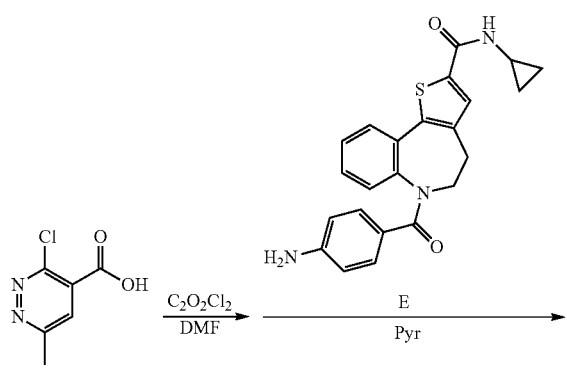

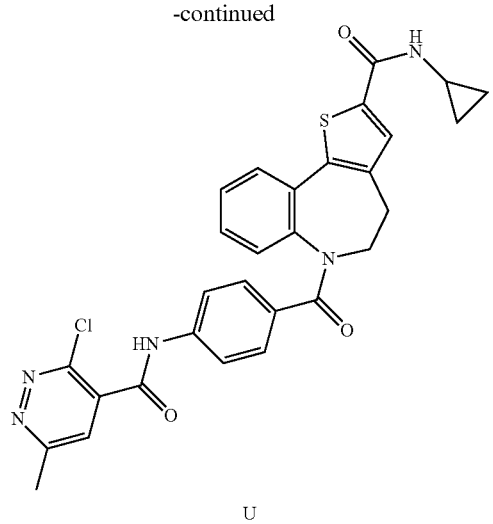

U

To a 20 mL flask containing 20 mL of DMF added 1 mL of oxalyl chloride slowly, an orange solution formed after the addition. 300 mg of 3-Chloro-6-methyl-pyridazine-4-carboxylic acid was dissolved in 4 mL of the above orange solution and stirred for 5 mins at room temperature. Then 150 mg of the intermediate E was dissolved in 2 mL pyridine and then this pyridine solution was added to the above orange carboxylic acid solution. Reaction was finished in 5 mins at room temperature and was quenched with 1 mL NH$_4$OH. The solvent was then evaporated under vacuum and the residue was dissolved in CH$_3$CN and water and purified with prep HPLC to afford intermediate U (110 mg, 53%).

$^1$H-NMR (DMSO, 300 MHz): δ 8.35 (d, J=4.2 Hz, 1H), 7.94 (s, 1H), 7.66 (s, 1H), 7.53 (d, J=7.2 Hz, 2H), 7.19 (t, J=7.8 Hz, 1H), 6.98-6.80 (m, 3H), 6.75 (d, J=7.5 Hz, 1H), 4.18 (mc, 1H), 3.28-3.05 (m, 3H), 2.35-2.30 (m, 1H), 1.82 (s, 3H), 0.73 (m, 2H), 0.55 (m, 2H)

LCMS m/z [M+H]$^+$ C$_{29}$H$_{24}$ClN$_5$O$_3$S requires: 558.05. Found 558.21.

HPLC Tr (min), purity %: 3.18, 98%

Intermediate V

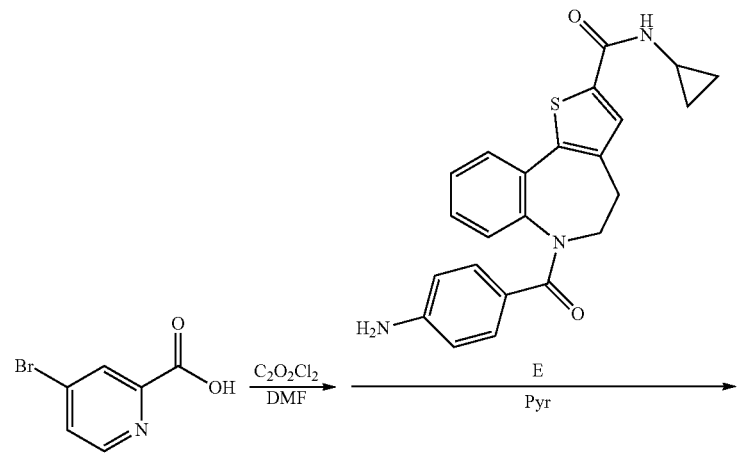

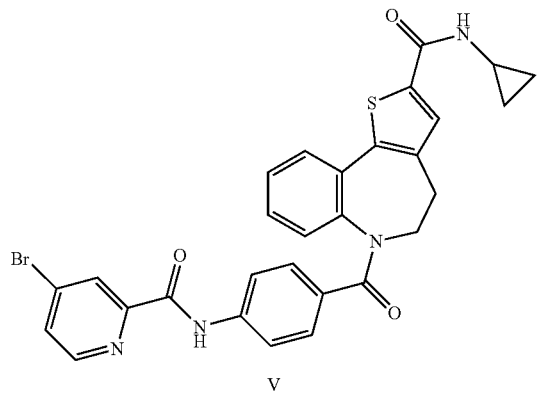

V

To a 20 mL flask containing 20 mL of DMF added 1 mL of oxalyl chloride slowly, an orange solution formed after the addition. 60 mg of 4-bromopiconilic acid was dissolved in 2 mL of the above orange solution and stirred for 5 mins at room temperature. Then 30 mg of the intermediate E was dissolved in 1 mL pyridine and then this pyridine solution was added to the above orange carboxylic acid solution. Reaction was finished in 5 mins at room temperature and was quenched with 1 mL NH$_4$OH. The solvent was then evaporated under vacuum and the residue was dissolved in CH$_3$CN and water and purified with prep HPLC to afford intermediate V (25 mg, 58%).

$^1$H-NMR (DMSO, 300 MHz): δ 8.75 (s, 1H), 8.32 (s, 1H), 7.65 (d, J=7.2 Hz, 1H), 7.40 (s, 1H), 7.38 (d, J=7.5 Hz, 2H), 7.36 (s, 1H), 7.18 (t, J=7.8 Hz, 1H), 7.08-7.02 (m, 2H), 6.84 (s, 1H), 6.75 (d, J=7.2 Hz, 1H), 5.20 (s, 1H), 4.92 (s, 1H), 3.30-3.08 (m, 3H), 2.96 (s, 1H), 2.82 (s, 1H), 0.85-0.83 (m, 2H), 0.65 (mc, 2H).

LCMS m/z [M+H]$^+$ C$_{29}$H$_{23}$BrN$_4$O$_3$S requires; 587.07. Found 587.28.

HPLC Tr (min), purity %: 3.30, 98%

Example 1

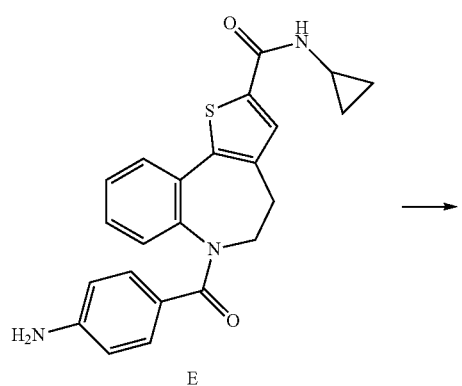

E

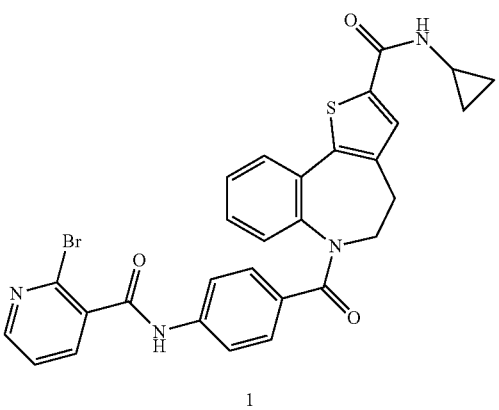

1

To a solution of intermediate E (80 mg, 0.2 mM) in dry pyridine (2 mL) was added 2-bromonicotinic acid (60 mg, 0.3 mM) and HATU (114 mg, 0.3 mM) and the solution stirred under N$_2$ at RT for 2 h. Volatiles were removed under reduced pressure at 40° C. and the resulting residue was purified by preparative HPLC (20% CH$_3$CN in H$_2$O with a gradient from 20% to 95%) to afford example 1 (63 mg, 54%) as a white powder after lyophilization.

$^1$H-NMR (DMSO, 300 MHz): δ 8.82 (s, 1H), 8.41 (d, J=3.3 Hz, 1H), 7.89 (d, J=7.5 Hz, 1H), 7.70 (d, J=8.1 Hz, 1H), 7.44 (d, J=8.1 Hz, 2H), 7.34 (s, 1H), 7.21 (t, J=7.8 Hz, 1H), 7.04-7.01 (m, 2H), 6.84 (s, 1H), 6.73 (d, J=7.5 Hz, 1H), 5.27 (s, 1H), 4.96 (d, J=11.7 Hz, 1H), 3.32-3.16 (m, 3H), 2.97 (d, J=16.2 Hz, 1H), 2.83 (s, 1H), 0.85-0.83 (m, 2H), 0.66 (mc, 2H).

LCMS m/z [M+H]$^+$ C$_{29}$H$_{23}$BrN$_4$O$_3$S requires: 587.07. Found 587.23.

HPLC Tr (min), purity %: 3.31, 95%

Example 2

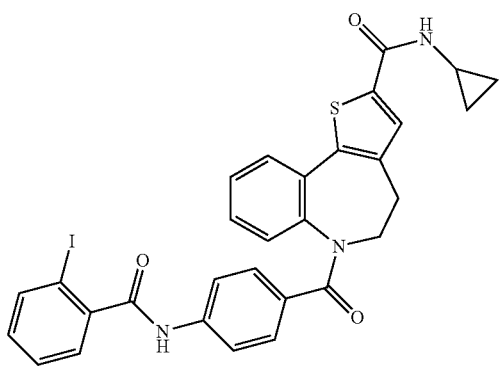

To a solution of the amine E (0.050 g, 0.12 mM) in dry pyridine (1 mL) was added slowly a solution of 2-iodobenzoyl chloride (0.065 g, 0.27 mM) in CH$_3$CN (1 mL) and stirred under N$_2$ at RT fro 2 h. Volatiles were removed under reduced pressure at 40° C., the resulting residue dissolved in EtOAc (150 mL) and the organic phase was washed 2× each with aqueous dilute NaHCO$_3$, then H$_2$O followed by brine. The residue was purified by prep HPLC (0% to 95% water/CH$_3$CN) to afford 2 (3.2 mg, 5%).

$^1$H-NMR (DMSO, 300 MHz): δ 10.44 (s, 1H), 8.48 (d, J=4.2 Hz, 1H), 7.84 (d, J=7.8 Hz, 1H), 7.71 (d, J=6.9 Hz, 1H), 7.60 (s, 1H), 7.46-7.39 (m, 3H), 7.22 (m, 2H), 7.05 (m, 1H), 7.94 (d, J=6.3 Hz, 2H), 7.81 (m, 1H), 3.16-3.05 (m, 2H), 2.76 (m, 2H), 0.66 (m, 2H), 0.51 (m, 2H).

LCMS m/z [M+H]$^+$ C$_{30}$H$_{24}$IN$_3$O$_3$S requires: 633.50. Found 633.93.

HPLC Tr (min), purity %: 2.45, 90%.

Example 3

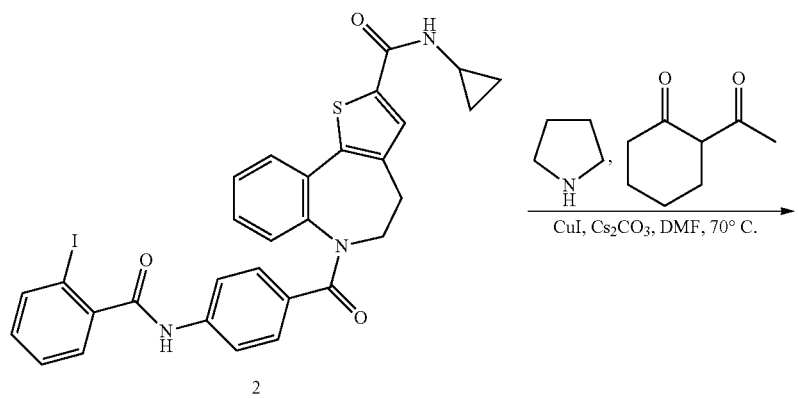

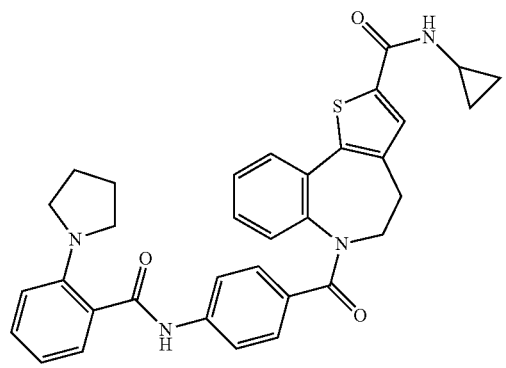

An oven-dried Schlenk tube equipped with a teflon valve was charged with a magnetic stir bar, CuI (0.6 mg, 0.003 mmol, 5 mol %), $Cs_2CO_3$ (39 mg, 0.12 mmol). The tube was evacuated and backfilled with argon (this procedure was repeated three times). Under a counter flow of argon, pyrrolidine and the aryl iodide 2 and DMF (2 mL) were added. Finally, 2-acetylcyclohexanone (1.8 mg, 0.013 mmol, 20 mol %) was added via syringe, the tube was sealed and the mixture was allowed to stir under argon at 70° C. overnight. Upon completion of the reaction, the mixture was diluted with ethyl acetate, passed through a fritted glass filter to remove the inorganic salts and the solvent was removed with the aid of a rotary evaporator. The residue was purified by prep HPLC (0% to 95% water/$CH_3CN$) to afford 3 (14 mg, 28%).

$^1$H-NMR (DMSO, 300 MHz): δ10.41 (s, 1H), 8.54 (d, J=2.7 Hz, 1H), 7.77 (d, J=8.1 Hz, 1H), 7.65 (s, 1H), 7.50 (d, J=7.8 Hz, 2H), 7.25-7.23 (m, 3H), 7.10 (t, J=7.5 Hz, 1H), 6.96 (d, J=6.9 Hz, 2H), 6.84 (d, J=6.9 Hz, 1H), 6.75 (d, J=8.7 Hz, 1H), 6.69 (t, J=7.2 Hz, 1H), 4.89 (s, 1H), 3.25-3.05 (m, 7H), 2.81-2.80 (m, 1H), 1.81 (s, 4H), 0.70 (m, 2H), 0.56 (m, 2H).

LCMS m/z $[M+H]^+$ $C_{34}H_{32}N_4O_3S$ requires: 577.70. Found 577.15.

HPLC Tr (min), purity %: 3.63, 98%.

Example 4

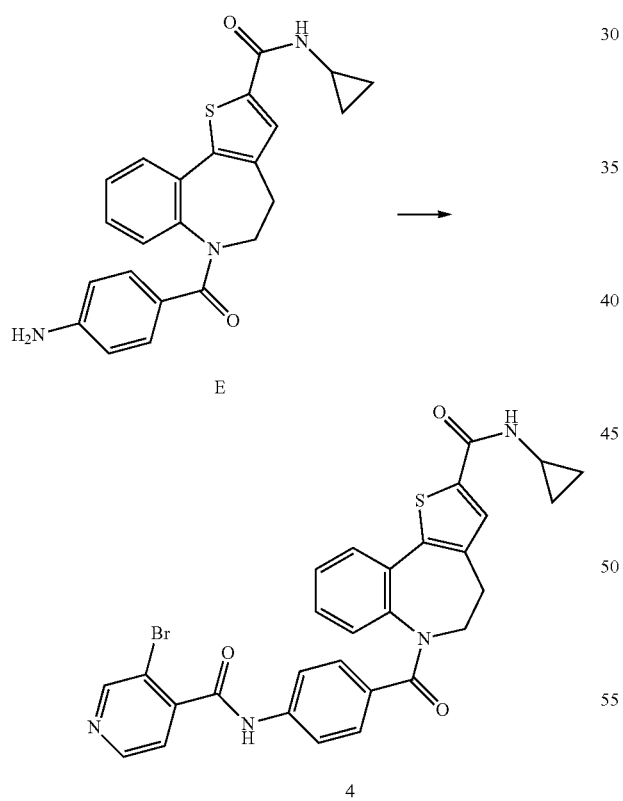

4

To a 50 mL flask containing 20 mL of DMF was added 1 mL of oxalyl chloride slowly and stirred for 10 min at RT. 100 mg of 3-bromo-isonicotinic acid was dissolved in 2 mL of the above solution and stirred for 5 min at RT. Then 50 mg of intermediate E was dissolved in 1 mL pyridine and added to the above solution. The reaction was completed in 5 min at RT and quenched with 1 mL $NH_4OH$. The solvent was then evaporated under vacuum and the residue dissolved in $CH_3CN$ and water and purified with prep HPLC (0% to 95% water/Acetonitrile) to afford 4 (27 mg, 40%).

$^1$H-NMR (DMSO, 300 MHz): δ 8.95 (s, 1H), 8.43 (d, J=3.3 Hz, 1H), 7.76 (t, J=7.5 Hz, 1H), 7.68 (d, J=8.1 Hz, 1H), 7.40 (d, J=8.1 Hz, 1H), 7.25 (s, 2H), 7.15 (t, J=7.8 Hz, 1H), 7.07-7.02 (m, 2H), 6.82 (s, 1H), 6.67 (d, J=7.2 Hz, 1H), 5.22 (s, 1H), 4.88 (d, J=8.7 Hz, 1H), 3.28-3.12 (m, 3H), 2.95 (d, J=12.3 Hz, 1H), 2.82 (s, 1H), 0.84-0.80 (m, 2H), 0.66 (mc, 2H).

LCMS m/z $[M+H]^+$ $C_{29}H_{23}BrN_4O_3S$ requires: 587.07. Found 587.02.

HPLC Tr (min), purity %: 3.30, 98%

Example 5

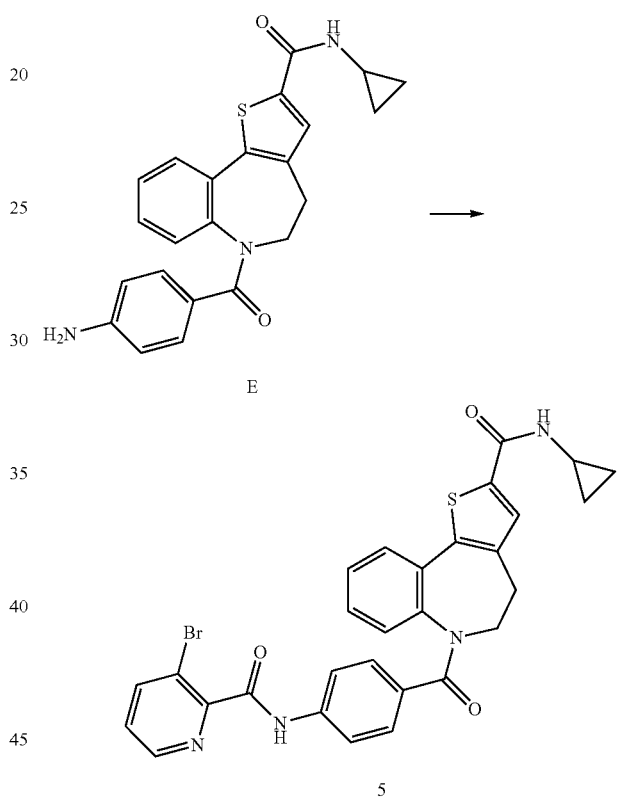

5

To a 50 mL flask containing 20 mL of DMF was added 1 mL of oxalyl chloride slowly and stirred for 10 min at RT. 100 mg of 3-bromo-pyridine-2-carboxylic acid was dissolved in 2 mL of the solution and stirred for 5 min at RT. A solution of E (50 mg) dissolved in pyridine (1 mL) and added to the above solution. The reaction was completed in 5 min at RT and quenched with 1 mL $NH_4OH$. The solvent was then evaporated under vacuum and the residue dissolved in $CH_3CN$ and water and purified with prep HPLC (0% to 95% water/Acetonitrile) to afford 5 (29 mg, 42%).

$^1$H-NMR (DMSO, 300 MHz): δ 8.92 (s, 1H), 8.45 (d, J=3.3 Hz, 1H), 7.70 (d, J=7.5 Hz, 1H), 7.63 (d, J=8.1 Hz, 1H), 7.42 (d, J=8.1 Hz, 1H), 7.28 (s, 1H), 7.13 (d, J=7.8 Hz, 2H), 7.09-7.04 (m, 2H), 6.81 (s, 1H), 6.64 (d, J=7.5 Hz, 1H), 5.21 (s, 1H), 4.85 (d, J=8.5 Hz, 1H), 3.23-3.16 (m, 3H), 2.94 (d, J=12.3 Hz, 1H), 2.80 (s, 1H), 0.86-0.81 (m, 2H), 0.66 (s, 2H).

LCMS m/z $[M+H]^+$ $C_{29}H_{23}BrN_4O_3S$ requires: 587.07. Found 587.34.

HPLC Tr (min), purity %: 3.31, 98%

Example 6

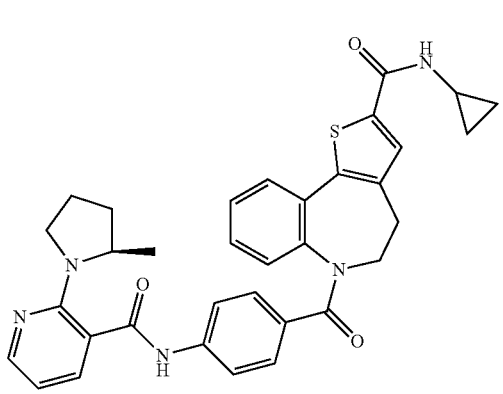

Compound 1 (16 mg, 0.03 mM) and 2-methylpyrrolidine (0.1 mL) were dissolved in DMF (1 mL) and stirred at 70° C. overnight. Volatiles were removed under reduced pressure at 40° C. and the resulting residue was purified by preparative HPLC (0% to 95% water/Acetonitrile) to afford 6 (15 mg, 94%) as a white powder.

$^1$H-NMR (DMSO, 300 MHz): δ 10.53 (s, 1H), 8.50 (d, J=3.9 Hz, 1H), 8.08 (d, J=4.5 Hz, 1H), 7.73 (t, J=7.8 Hz, 2H), 7.61 (s, 1H), 7.43 (d, J=8.1 Hz, 2H), 7.22 (t, J=7.8 Hz, 1H), 7.05 (t, J=7.5 Hz, 1H), 6.94 (d, J=7.8 Hz, 2H), 6.71 (t, J=7.5 Hz, 1H), 4.82 (mc, 1H), 4.21 (dd, J=6.0, 12.3 Hz, 1H), 3.66-3.37 (m, 2H), 3.16-3.00 (m, 3H), 2.76-2.44 (m, 1H), 2.01-1.87 (m, 1H), 1.85-1.72 (m, 1H), 1.70-1.67 (m, 1H), 1.56-1.48 (m, 1H), 1.11 (d, J=5.7 Hz, 1H), 0.65 (m, 2H), 0.51 (m, 2H).

LCMS m/z [M+H]$^+$ C$_{34}$H$_{33}$N$_5$O$_3$S requires: 591.72. Found 591.68.

HPLC Tr (min), purity %: 3.25, 98%

Example 7

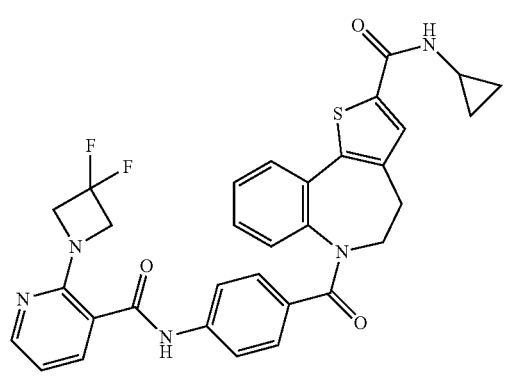 [SMILES: O=C(NC1CC1)c1cc2c(s1)-c1ccccc1N(C(=O)c1ccc(NC(=O)c3cccnc3N3CC(F)(F)C3)cc1)CC2]

Compound 1 (14 mg, 0.02 mM) and 3,3-difluoroazetidine (20 mg) were dissolved in DMF (1 mL) and triethylamine (0.5 mL). The reaction mixture was stirred at 70° C. overnight. Volatiles were removed under reduced pressure at 40° C. and the resulting residue was purified by preparative HPLC (0% to 95% water/Acetonitrile) to afford 7 (6 mg, 42%) as a white powder.

$^1$H-NMR (DMSO, 300 MHz): δ 10.47 (s, 1H), 8.54 (d, J=3.3 Hz, 1H), 8.26 (d, J=3.3 Hz, 1H), 7.77 (d, J=7.8 Hz, 2H), 7.66 (s, 1H), 7.47 (d, J=7.5 Hz, 2H), 7.27 (t, J=7.5 Hz, 1H), 7.09 (t, J=7.5 Hz, 1H), 6.98 (d, J=8.1 Hz, 2H), 6.88-6.85 (m, 2H), 4.92 (mc, 1H), 4.32-4.20 (m, 4H), 3.19-3.11 (m, 3H), 2.80 (s, 1H), 0.70 (m, 2H), 0.57 (s, 2H).

LCMS m/z [M+H]$^+$ C$_{32}$H$_{27}$F$_2$N$_5$O$_3$S requires: 600.65. Found 600.48.

HPLC Tr (min), purity %: 3.18, 98%

Example 8

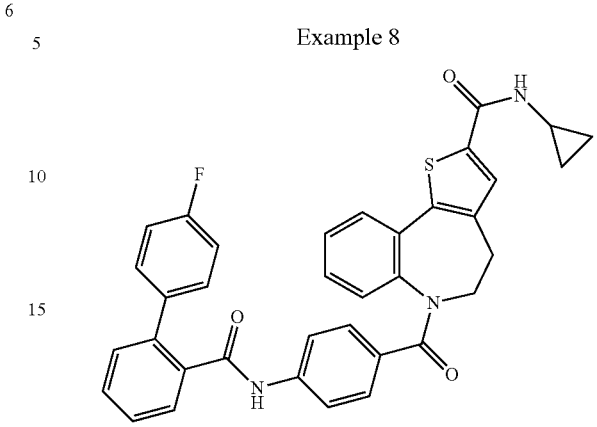

Compound 2 (23 mg, 0.036 mM) and 4-fluorophenylboronic acid (10 mg) were dissolved in DME (2 mL) and water (1 mL). To the above solution was added Palladium tetrakis (triphenylphosphine) (6 mg) and potassium carbonate (20 mg). The reaction mixture was heated to 120° C. for 10 min in a microwave reactor. The reaction mixture was filtered and volatiles were removed under reduced pressure at 40° C. and the resulting residue was purified by preparative HPLC (0% to 95% water/Acetonitrile) to afford 8 (8 mg, 36%).

$^1$H-NMR (DMSO, 300 MHz): δ 8.57 (s, 1H), 8.31 (dd, J=1.2, 7.8 Hz, 1H), 8.17-7.90 (m, 7H), 7.79-7.74 (m, 3H), 7.77-7.49 (m, 5H), 7.32 (d, J=7.2 Hz, 1H), 5.46 (s, 1H), 3.85-3.61 (m, 4H), 3.36-3.30 (m, 1H), 0.69 (m, 2H), 0.55 (m, 2H).

LCMS m/z [M+H]$^+$ C$_{34}$H$_{27}$N$_3$O$_3$S$_2$ requires: 602.70. Found 602.02.

HPLC Tr (min), purity %: 3.37, 98%.

Example 9

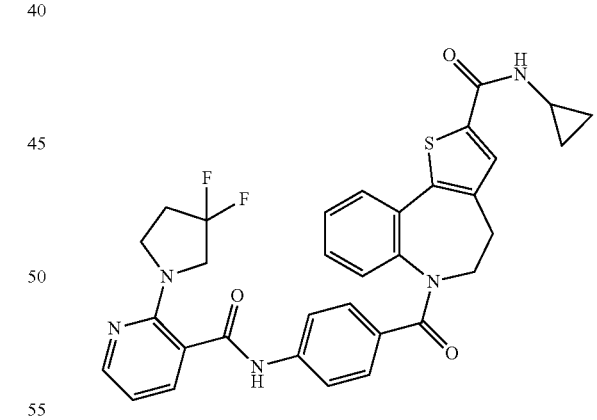

Compound 1 (14 mg, 0.02 mM) and 3,3-difluoropyrrolidine (20 mg) were dissolved in DMF (1 mL) and triethylamine (0.5 mL). The reaction mixture was heated to 140° C. for 8 h in a microwave reactor. Volatiles were removed under reduced pressure at 40° C. and the resulting residue was purified by preparative HPLC (0% to 95% water/Acetonitrile) to afford 9 (8 mg, 44%).

$^1$H-NMR (DMSO, 300 MHz): δ 10.55 (s, 1H), 8.53 (d, J=4.2 Hz, 1H), 8.22 (d, J=4.8 Hz, 1H), 7.77 (d, J=7.8 Hz, 2H), 7.70 (d, J=7.8 Hz, 1H), 7.65 (s, 1H), 7.49 (d, J=8.1 Hz, 1H), 7.24 (t, J=7.2 Hz, 1H), 7.09 (t, J=6.9 Hz, 1H), 6.98 (d, J=8.4

Hz, 1H), 6.86-6.77 (m, 3H), 4.87 (mc, 1H), 3.77-3.59 (m, 6H), 3.15-3.09 (m, 3H), 2.82-2.80 (m, 1H), 0.69 (m, 2H), 0.55 (m, 2H).

LCMS m/z [M+H]$^+$ C$_{33}$H$_{29}$F$_2$N$_5$O$_3$S requires: 613.68. Found 614.03.

HPLC Tr (min), purity %: 2.61, 98%

Example 10

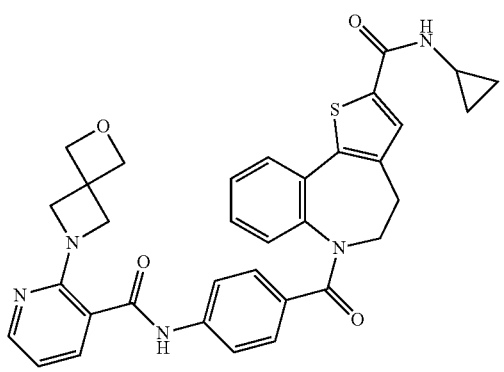 [SMILES: O=C(NC1CC1)c1cc2c(s1)-c1ccccc1N(C(=O)c1ccc(NC(=O)c3cccnc3N3CC4(COC4)C3)cc1)CC2]

Compound 1 (15 mg, 0.02 mM) and spirocyclicamine (25 mg) [Angew Chem Intl edition English 2008, 47, p4512] were dissolved in DMF (1 mL) and triethylamine (0.5 mL). The reaction mixture was stirred at 70° C. for 16 h. Volatiles were removed under reduced pressure at 40° C. and the resulting residue was purified by preparative HPLC using a gradient 0% to 95% water/Acetonitrile to afford 10 (5 mg, 35%) as a white powder.

$^1$H-NMR (DMSO, 300 MHz): δ 10.52 (s, 1H), 8.49 (d, J=3.3 Hz, 1H), 8.11 (d, J=3.3 Hz, 1H), 8.08 (d, J=5.7 Hz, 1H), 7.75-7.65 (m, 2H), 7.61 (s, 1H), 7.44 (d, J=7.5 Hz, 2H), 7.22 (t, J=7.8 Hz, 1H), 7.05 (t, J=7.5 Hz, 1H), 6.95 (d, J=8.1 Hz, 1H), 6.81-6.71 (m, 2H), 4.82 (mc, 1H), 3.69 (s, 3H), 3.39 (s, 2H), 3.16-3.05 (m, 4H), 2.88 (s, 2H), 2.75 (s, 1H), 0.65 (d, J=6.6 Hz, 2H), 0.50 (s, 2H).

LCMS m/z [M+H]$^+$ C$_{34}$H$_{31}$N$_5$O$_4$S requires: 606.71. Found 606.48.

HPLC Tr (min), purity %: 3.15, 98%

Example 11

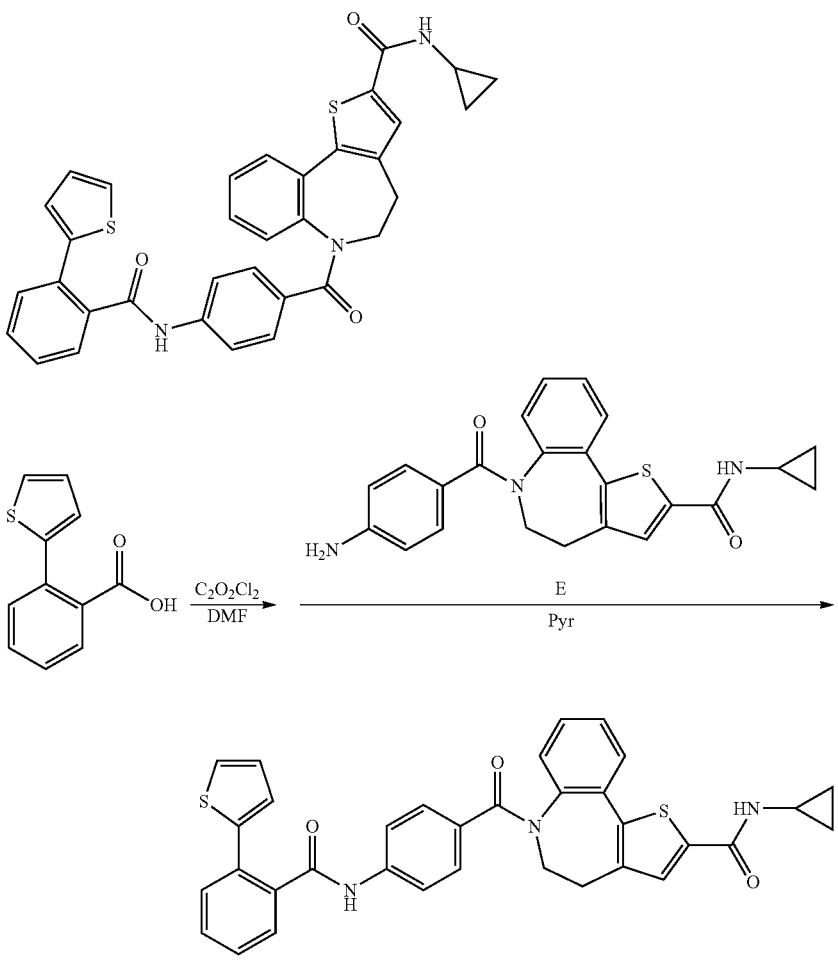

To a 50 mL flask containing 20 mL of DMF was added 1 mL of oxalyl chloride slowly and stirred for 10 min at RT. 100 mg of the 2-thiophen-2-yl-benzoic acid was dissolved in 2 mL of the above solution and stirred for 5 min at RT. Then 50 mg of intermediate E was dissolved in 1 mL pyridine and added to the above solution. The reaction was completed in 5 min at RT and quenched with 1 mL NH$_4$OH. The solvent was then evaporated under vacuum and the residue dissolved in CH$_3$CN and water and purified with prep HPLC (0% to 95% water/Acetonitrile) to afford the product 11 (27 mg, 40%).

$^1$H-NMR (DMSO, 300 MHz): δ 8.51 (s, 1H), 7.78 (d, J=7.8 Hz, 1H), 7.55-7.51 (m, 3H), 7.40-7.26 (m, 3H), 7.26-7.22 (m, 3H), 7.02-6.97 (m, 5H), 6.79 (d, J=7.8 Hz, 1H), 4.98-4.90 (m, 1H), 3.26-3.07 (m, 4H), 2.81-2.76 (m, 1H), 0.76-0.62 (m, 2H), 0.60-0.56 (m, 2H).

LCMS m/z [M+H]$^+$ C$_{34}$H$_{27}$N$_3$O$_3$S$_2$ requires: 590.70. Found 590.97.

HPLC Tr (min), purity %: 3.20, 98%.

Example 12

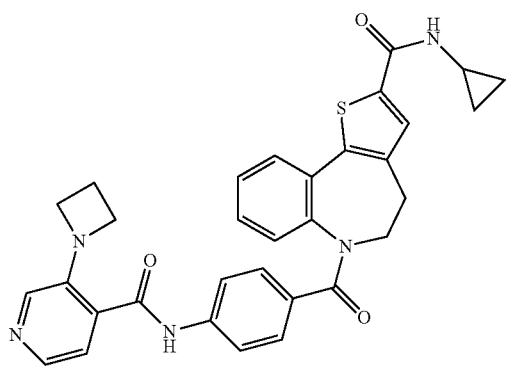 [SMILES: O=C(NC1CC1)c1cc2c(s1)-c1ccccc1N(C(=O)c1ccc(NC(=O)c3ccncc3N3CCC3)cc1)CC2]

Compound 4 (15 mg, 0.02 mM) was dissolved in azetidine (0.5 mL) and the reaction mixture was stirred at 70° C. for 16 h. Volatiles were removed under reduced pressure at 40° C. and the resulting residue was purified by preparative HPLC (0% to 95% water/Acetonitrile) to afford 12 (10 mg, 71%).

$^1$H-NMR (DMSO, 300 MHz): δ 10.69 (s, 1H), 8.54 (s, 1H), 8.05 (d, J=5.4 Hz, 1H), 7.98 (s, 1H), 7.77 (d, J=8.1 Hz, 1H), 7.66 (s, 1H), 7.55 (d, J=9.0 Hz, 1H), 7.48 (d, J=9.0 Hz, 1H), 7.26 (t, J=8.1 Hz, 1H), 7.09-6.83 (m, 3H), 4.87 (mc, 1H), 3.91 (t, J=6.9 Hz, 3H), 3.21-3.05 (m, 4H), 2.81 (s, 1H), 2.28 (t, J=7.2 Hz, 2H), 0.70 (d, J=6.6 Hz, 2H), 0.55 (s, 2H).

LCMS m/z [M+H]$^+$ C$_{32}$H$_{29}$N$_5$O$_3$S requires: 564.67. Found 564.28.

HPLC Tr (min), purity %: 2.60, 98%

Example 13

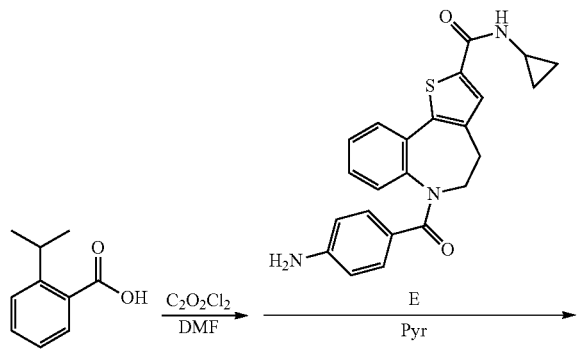

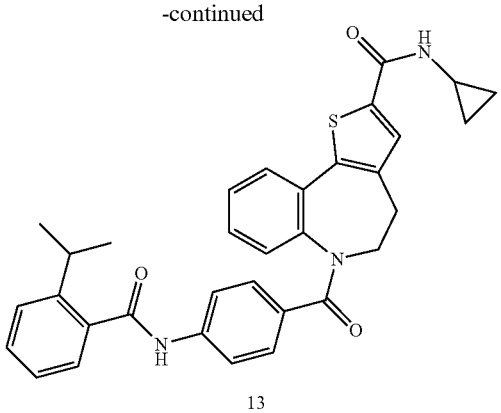

To a 50 mL flask containing 20 mL of DMF was added 1 mL of oxalyl chloride slowly and stirred for 10 min at RT. 100 mg of 2-isopropyl-benzoic acid was dissolved in 2 mL of the above solution and stirred for 5 min at RT. Then 50 mg of E was dissolved in 1 mL pyridine and added to the above solution. The reaction was completed in 5 min at RT and quenched with 1 mL NH$_4$OH. The solvent was then evaporated under vacuum and the residue dissolved in CH$_3$CN and water and purified with prep HPLC (0% to 95% water/Acetonitrile) to afford 13 (127 mg, 62%).

$^1$H-NMR (DMSO, 300 MHz): δ 8.59 (s, 1H), 7.80 (d, J=7.5 Hz, 1H), 7.46-7.33 (m, 6H), 7.26-7.06 (m, 2H), 7.06-7.04 (m, 4H), 6.82 (d, J=6.3 Hz, 1H), 4.94 (s, 1H), 3.29-3.08 (m, 1H), 3.08-2.77 (m, 4H), 1.19 (d, J=6.6 Hz, 1H), 0.74-0.70 (m, 2H), 0.62-0.57 (m, 2H).

LCMS m/z [M+H]$^+$ C$_{33}$H$_{31}$N$_3$O$_3$S requires: 550.75. Found 550.08.

HPLC Tr (min), purity %: 3.40, 98%.

Example 14

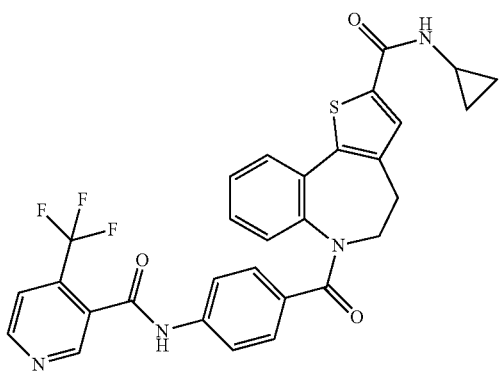 [SMILES: O=C(NC1CC1)c1cc2c(s1)-c1ccccc1N(C(=O)c1ccc(NC(=O)c3cnccc3C(F)(F)F)cc1)CC2]

To a 50 mL flask containing 20 mL of DMF was added 1 mL of oxalyl chloride slowly and stirred for 10 min at RT. 100 mg of the 4-trifluoromethyl nicotinic acid was dissolved in 2 mL of the above solution and stirred for 5 min at RT. Then 50 mg of E was dissolved in 1 mL pyridine and added to the above solution. The reaction was completed in 5 min at RT and quenched with 1 mL NH$_4$OH. The solvent was then evaporated under vacuum and the residue dissolved in CH$_3$CN and water and purified with prep HPLC (0% to 95% water/Acetonitrile) to afford 14 (56 mg, 82%).

$^1$H-NMR (DMSO, 300 MHz): δ 10.83 (s, 1H), 8.95-8.97 (m, 1H), 8.54 (d, J=3.9 Hz, 1H), 7.88 (d, J=5.1 Hz, 1H), 7.77

(d, J=7.5 Hz, 1H), 7.47 (d, J=8.4 Hz, 2H), 7.27 (t, J=7.2 Hz, 1H), 7.11 (t, J=6.6 Hz, 1H), 7.01 (d, J=8.1 Hz, 2H), 6.84 (d, J=8.1 Hz, 1H), 4.88 (s, 1H), 3.05-3.22 (m, 4H), 2.80-2.81 (m, 1H), 0.70 (m, 2H), 0.56 (m, 2H).

LCMS m/z [M+H]$^+$ $C_{30}H_{23}F_3N_4O_3S$ requires: 577.60. Found 577.11.

HPLC Tr (min), purity %: 3.16, 98%.

Example 15

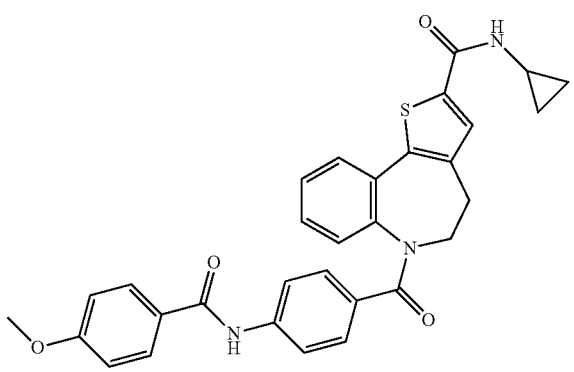 [SMILES: COc1ccc(C(=O)Nc2ccc(C(=O)N3CCc4cc(C(=O)NC5CC5)sc4-c4ccccc43)cc2)cc1]

To a 50 mL flask containing 20 mL of DMF was added 1 mL of oxalyl chloride slowly and stirred for 10 min at RT. 100 mg of 4-methoxy benzoic acid was dissolved in 2 mL of the above solution and stirred for 5 min at RT. Then 50 mg of E was dissolved in 1 mL pyridine and added to the above solution. The reaction was completed in 5 min at RT and quenched with 1 mL NH$_4$OH. The solvent was then evaporated under vacuum and the residue dissolved in CH$_3$CN and water and purified with prep HPLC (0% to 95% water/Acetonitrile) to afford 15 (26 mg, 48%).

$^1$H-NMR (DMSO, 300 MHz): δ 10.03 (s, 1H), 8.45 (d, J=4.2 Hz, 1H), 7.84 (d, J=8.4 Hz, 2H), 7.71 (d, J=7.8 Hz, 1H), 7.53 (s, 1H), 7.50 (d, J=8.4 Hz, 2H), 7.18 (t, J=6.9 Hz, 1H), 7.03-6.92 (m, 4H), 6.78 (d, J=6.9 Hz, 1H), 4.84 (mc, 2H), 3.16-2.78 (m, 3H), 2.77-2.75 (m, 1H), 0.65 (m, 2H), 0.51 (m, 2H).

LCMS m/z [M+H]$^+$ $C_{31}H_{27}N_3O_4S$ requires: 538.63. Found 538.01.

HPLC Tr (min), purity %: 3.19, 98%

Example 16

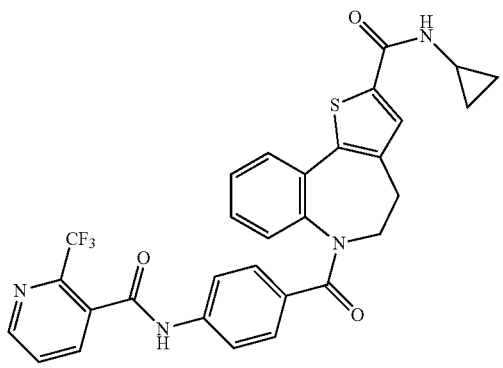 [SMILES: O=C(NC1CC1)c1cc2c(s1)-c1ccccc1N(C(=O)c1ccc(NC(=O)c3cccnc3C(F)(F)F)cc1)CC2]

Intermediate C (80 mg) and intermediate F (20 mg) were dissolved in DMF (3 mL), and PyBroP (65 mg) and DMAP (17 mg) were added to the above solution. The reaction mixture was heated at 80° C. for 1 hour. The solvent was evaporated and the residue was purified with preparative HPLC (0% to 95% water/Acetonitrile) to afford 16 (30 mg, 20%).

$^1$H-NMR (DMSO, 300 MHz): δ 10.39 (s, 1H), 8.55 (d, J=3.9 Hz, 1H), 7.82 (d, J=7.2 Hz, 1H), 7.65 (d, J=7.5 Hz, 1H), 7.60-7.46 (m, 3H), 7.32 (d, J=7.2 Hz, 1H), 7.12 (t, J=7.5 Hz, 1H), 7.06 (t, J=7.5 Hz, 1H), 6.85 (d, J=7.5 Hz, 1H), 4.76 (mc, 1H), 3.38-3.10 (m, 3H), 2.82-2.75 (m, 1H), 0.65 (m, 2H), 0.51 (m, 2H).

LCMS m/z [M+H]$^+$ $C_{30}H_{22}F_4N_4O_3S$ requires: 595.58. Found 595.20.

HPLC Tr (min), purity %: 3.30, 98%

Example 17

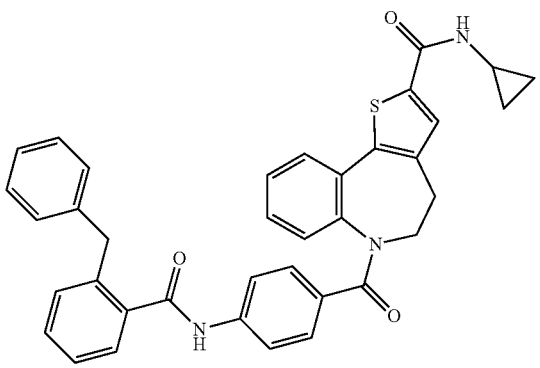 [SMILES: O=C(NC1CC1)c1cc2c(s1)-c1ccccc1N(C(=O)c1ccc(NC(=O)c3ccccc3Cc3ccccc3)cc1)CC2]

2-Benzylbenzoic acid (100 mg) was dissolved in NMP (3 mL) and thionyl chloride (0.41 mL) was added. After stirring for 5 min, intermediate E (50 mg) was added to the above solution. The reaction was completed after stirring for 10 min at RT. The reaction mixture was quenched with water and extracted with EtOAc. The solvent was evaporated and the residue was purified with preparative HPLC (0% to 95% water/Acetonitrile) to afford 17 (30 mg, 45%).

$^1$H-NMR (DMSO, 300 MHz): δ 10.36 (s, 1H), 8.50 (d, J=3.9 Hz, 1H), 7.72 (d, J=7.8 Hz, 1H), 7.61 (s, 1H), 7.45 (d, J=8.4 Hz, 1H), 7.37-7.34 (m, 2H), 7.32-7.11 (m, 3H), 7.10-7.03 (m, 5H), 6.92 (d, J=7.8 Hz, 2H), 6.80 (d, J=6.9 Hz, 1H), 4.83 (mc, 1H), 4.01 (s, 2H), 3.22-3.00 (m, 3H), 2.78-2.73 (m, 1H), 0.65 (m, 2H), 0.51 (m, 2H).

LCMS m/z [M+H]$^+$ $C_{37}H_{31}N_3O_3S$ requires: 598.73. Found 598.12.

HPLC Tr (min), purity %: 3.45, 98%

Example 18

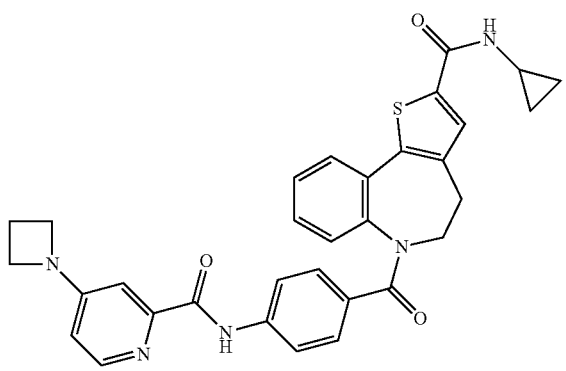 [SMILES: O=C(Nc1ccc(C(=O)N2CCc3cc(C(=O)NC4CC4)sc3-c3ccccc32)cc1)c1cc(N2CCC2)ccn1]

Intermediate V (10 mg, 0.013 mM) was dissolved in azetidine (0.5 mL) and the reaction mixture was stirred at 70° C. for 3 h. Volatiles were removed under reduced pressure at 40° C. and the resulting residue was purified by preparative HPLC (0% to 95% water/MeCN) to afford 18 (5 mg, 45%).

$^1$H-NMR (DMSO, 300 MHz): δ 10.61 (s, 1H), 8.55 (d, J=3.6 Hz, 1H), 8.14 (d, J=5.1 Hz, 1H), 7.72 (d, J=7.8 Hz, 1H), 7.73-7.62 (m, 3H), 7.24 (s, 1H), 7.01 (t, J=8.7 Hz, 1H), 6.84 (s, 1H), 6.57-6.52 (m, 1H), 4.87 (mc, 1H), 4.08-3.58 (m, 3H), 2.85-2.66 (m, 4H), 2.53 (s, 1H), 2.29-2.15 (m, 2H), 0.70 (m, 2H), 0.56 (m, 2H).

LCMS m/z [M+H]$^+$ C$_{32}$H$_{29}$N$_5$O$_3$S requires: 564.67. Found 564.45.

HPLC Tr (min), purity %: 2.56, 98%

Example 19

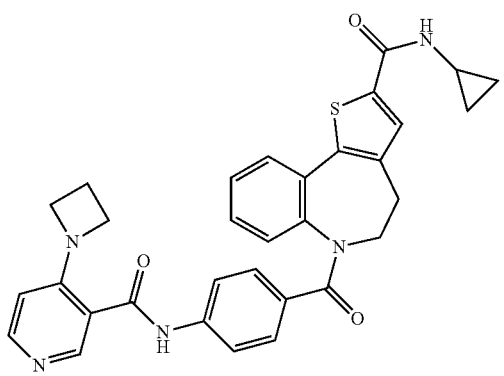 [SMILES: O=C(NC1CC1)c1cc2c(s1)-c1ccccc1N(C(=O)c1ccc(NC(=O)c3cnccc3N3CCC3)cc1)CC2]

Intermediate G (15 mg, 0.02 mM) was dissolved in azetidine (0.5 mL) and the reaction mixture was stirred at 70° C. for 16 h. Volatiles were removed under reduced pressure at 40° C. and the resulting residue was purified by preparative HPLC (0% to 95% water/Acetonitrile) to afford 19 (10 mg, 70%).

$^1$H-NMR (DMSO, 300 MHz): δ 10.55 (s, 1H), 8.55 (d, J=3.6 Hz, 1H), 8.18 (d, J=5.1 Hz, 1H), 7.77 (d, J=7.8 Hz, 1H), 7.70-7.66 (m, 3H), 7.25 (t, J=7.8 Hz, 1H), 7.07 (t, J=6.9 Hz, 1H), 6.85-6.83 (m, 1H), 6.49-6.47 (m, 1H), 4.88 (mc, 1H), 4.01-3.38 (m, 3H), 2.95-2.56 (m, 4H), 2.49 (s, 1H), 2.39-2.30 (m, 2H), 0.70 (m, 2H), 0.56 (m, 2H).

LCMS m/z [M+H]$^+$ C$_{32}$H$_{29}$N$_5$O$_3$S requires: 564.67. Found 564.39.

HPLC Tr (min), purity %: 2.54, 98%

Example 20

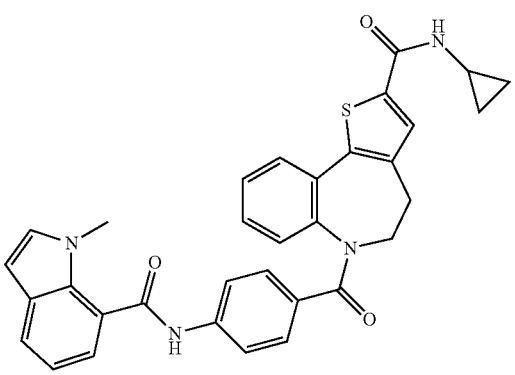 [SMILES: Cn1ccc2cccc(C(=O)Nc3ccc(C(=O)N4CCc5cc(C(=O)NC6CC6)sc5-c5ccccc54)cc3)c21]

To a 50 mL flask containing 20 mL of DMF was added 1 mL of oxalyl chloride slowly and stirred for 10 min at RT. 100 mg of 1-Methyl-1H-indole-7-carboxylic acid was dissolved in 2 mL of the above solution and stirred for 5 min at RT. Then 50 mg of E was dissolved in 1 mL pyridine and added to the above solution. The reaction was completed in 5 min at RT and quenched with 1 mL NH$_4$OH. The solvent was then evaporated under vacuum and the residue dissolved in CH$_3$CN and water and purified with prep HPLC (0% to 95% water/Acetonitrile) to afford 20 (14 mg, 20%).

$^1$H-NMR (DMSO, 300 MHz): δ 10.66 (s, 1H), 8.52 (d, J=3.6 Hz, 1H), 7.77 (d, J=7.8 Hz, 1H), 7.66 (s, 1H), 7.58 (d, J=8.1 Hz, 1H), 7.35 (d, J=3.0 Hz, 1H), 7.28-7.22 (m, 2H), 7.11-6.99 (m, 4H), 6.51 (d, J=2.4 Hz, 1H), 4.88 (mc, 1H), 3.68 (s, 3H), 3.25-3.10 (m, 3H), 2.80-2.75 (m, 1H), 0.70 (m, 2H), 0.55 (m, 2H).

LCMS m/z [M+H]$^+$ C$_{33}$H$_{28}$N$_4$O$_3$S requires: 561.67. Found 561.39.

HPLC Tr (min), purity %: 2.58, 98%

Example 21

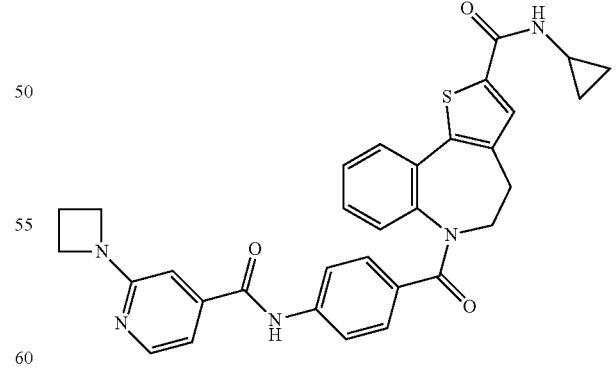

Intermediate H (15 mg, 0.02 mM) was dissolved in azetidine (0.5 mL) and the reaction mixture was stirred at 70° C. overnight. Volatiles were removed under reduced pressure at 40° C. and the resulting residue was purified by preparative HPLC (0% to 95% water/Acetonitrile) to afford 21 (13 mg, 73%).

¹H-NMR (DMSO, 300 MHz): δ 10.50 (s, 1H), 8.54 (d, J=3.9 Hz, 1H), 8.11 (d, J=5.7 Hz, 1H), 7.76 (d, J=8.1 Hz, 1H), 7.66 (s, 1H), 7.52 (d, J=8.7 Hz, 2H), 7.31-7.23 (m, 1H), 7.05-6.98 (m, 4H), 6.83-6.80 (m, 1H), 4.86 (mc, 1H), 4.13 (t, J=7.8 Hz, 4H), 3.21-3.05 (m, 3H), 2.81-2.80 (m, 1H), 2.42 (t, J=7.2 Hz, 2H), 0.70 (m, 2H), 0.55 (m, 2H).

LCMS m/z [M+H]⁺ $C_{32}H_{29}N_5O_3S$ requires: 564.67. Found 564.21.

HPLC Tr (min), purity %: 2.58, 98%

Example 22

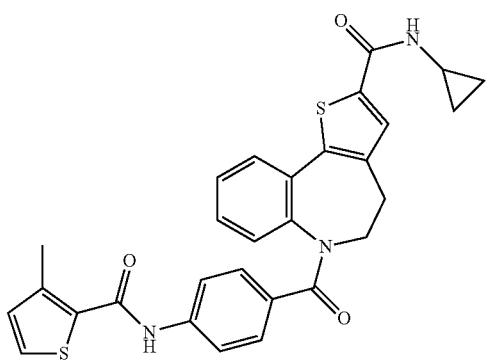 [SMILES: Cc1ccsc1C(=O)Nc1ccc(C(=O)N2CCc3cc(C(=O)NC4CC4)sc3-c3ccccc32)cc1]

To a 50 mL flask containing 20 mL of DMF was added 1 mL of oxalyl chloride slowly and stirred for 10 min at RT. 100 mg of 3-methyl-thiophene-2-carboxylic acid was dissolved in 2 mL of the above solution and stirred for 5 min at RT. Then 50 mg of E was dissolved in 1 mL pyridine and added to the above solution. The reaction was completed in 5 min at RT and quenched with 1 mL NH₄OH. The solvent was then evaporated under vacuum and the residue dissolved in CH₃CN and water and purified with prep HPLC (0% to 95% water/Acetonitrile) to afford 22 (11 mg, 17%).

¹H-NMR (DMSO, 300 MHz): δ 10.02 (s, 1H), 8.54 (d, J=4.2 Hz, 1H), 7.77 (d, J=7.8 Hz, 1H), 7.66 (s, 2H), 7.47 (d, J=7.5 Hz, 2H), 7.26 (t, J=7.5 Hz, 1H), 7.09 (t, J=7.5 Hz, 1H), 7.01-6.98 (m, 2H), 6.85-9.82 (m, 1H), 4.90 (mc, 1H), 3.21-3.11 (m, 3H), 2.83-2.80 (m, 1H), 2.38 (s, 3H), 0.70 (m, 2H), 0.56 (m, 2H).

LCMS m/z [M+H]⁺ $C_{29}H_{25}N_3O_3S_2$ requires: 528.66. Found 528.04.

HPLC Tr (min), purity %: 3.23, 98%

Example 23

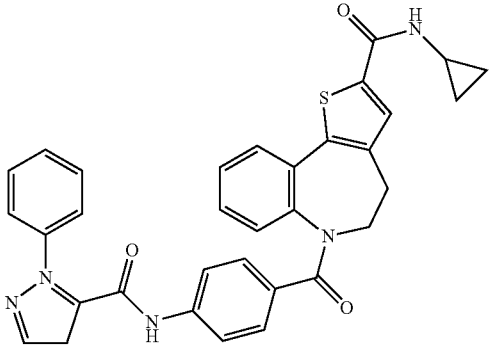

Intermediate E (20 mg) and 1-Phenyl-1H-Pyrazole-5-carboxylic acid chloride (18 mg) was dissolved in Pyridine (2 mL) and the reaction mixture was stirred for 30 min. The reaction was quenched with water and extracted with EtOAc (20 mL). The solvent was evaporated and the residue was purified with preparative HPLC (0% to 95% water/Acetonitrile) to afford 23 (24 mg, 60%).

¹H-NMR (DMSO, 300 MHz): δ 10.59 (s, 1H), 8.53 (d, J=4.2 Hz, 1H), 7.79 (s, 1H), 7.75 (d, J=6.9 Hz, 1H), 7.65 (s, 1H), 7.42-7.36 (m, 6H), 7.25 (t, J=7.5 Hz, 1H), 7.08 (t, J=7.5 Hz, 1H), 6.95 (d, J=8.4 Hz, 2H), 6.82 (d, J=7.8 Hz, 1H), 4.86 (mc, 1H), 3.20-3.04 (m, 3H), 2.80-2.78 (m, 1H), 0.70 (m, 2H), 0.55 (m, 2H).

LCMS m/z [M+H]⁺ $C_{33}H_{27}N_5O_3S$ requires: 574.66. Found 574.19.

HPLC Tr (min), purity %: 315, 98%

Example 24

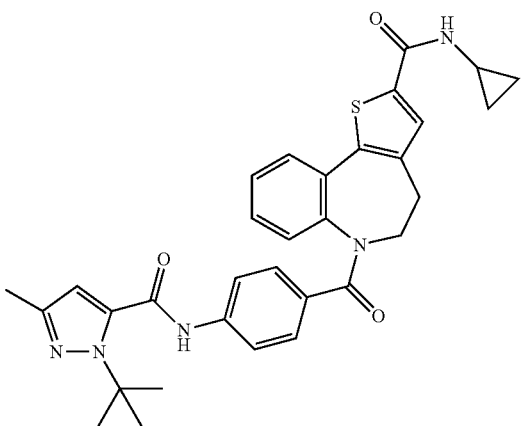 [SMILES: Cc1cc(C(=O)Nc2ccc(C(=O)N3CCc4cc(C(=O)NC5CC5)sc4-c4ccccc43)cc2)n(C(C)(C)C)n1]

Intermediate E (100 mg) and 1-(tert-butyl)-3-methyl-1H-pyrazole-5-carbonyl chloride (50 mg) was dissolved in pyridine (2 mL) and the reaction mixture was stirred at 60° C. for 30 min. The reaction was quenched with water and extracted with EtOAc (20 mL). The solvent was evaporated and the residue was purified with preparative HPLC (0% to 95% water/Acetonitrile) to afford 24 (25 mg, 15%).

¹H-NMR (DMSO, 300 MHz): δ 9.64 (s, 1H), 8.54 (d, J=4.2 Hz, 1H), 7.76 (d, J=7.5 Hz, 1H), 7.66 (s, 1H), 7.57 (d, J=8.7 Hz, 2H), 7.25 (t, J=7.2 Hz, 1H), 7.07 (t, J=7.5 Hz, 1H), 6.96 (d, J=8.4 Hz, 1H), 6.83-6.81 (m, 1H), 6.54 (s, 1H), 4.91 (mc, 1H), 3.20-3.10 (m, 3H), 2.81-2.80 (m, 1H), 2.44 (s, 3H), 1.60 (s, 9H), 0.70 (m, 2H), 0.56 (m, 2H).

LCMS m/z [M+H]⁺ $C_{32}H_{33}N_5O_3S$ requires: 568.70. Found 568.11.

HPLC Tr (min), purity %: 3.44, 98%

Example 25

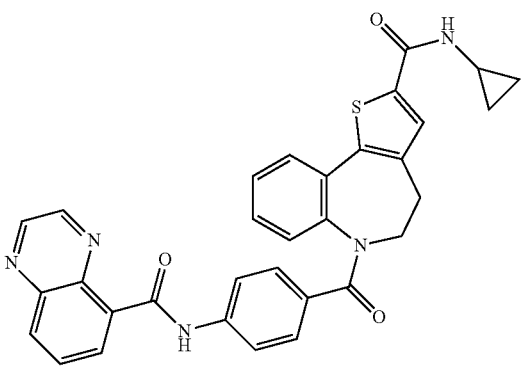 [SMILES: O=C(NC1CC1)c1cc2c(s1)-c1ccccc1N(C(=O)c1ccc(NC(=O)c3cccc4nccnc34)cc1)CC2]

To a 50 mL flask containing 20 mL of DMF was added 1 mL of oxalyl chloride slowly and stirred for 10 min at RT. 100 mg of quinoxaline-5-carboxylic acid was dissolved in 2 mL of the above solution and stirred for 5 min at RT. Then 50 mg of E was dissolved in 1 mL pyridine and added to the above solution. The reaction was completed in 5 min at RT and quenched with 1 mL NH$_4$OH. The solvent was then evaporated under vacuum and the residue dissolved in CH$_3$CN and water and purified with prep HPLC (0% to 95% water/Acetonitrile) to afford 25 (26.7 mg, 54%).

$^1$H-NMR (DMSO, 300 MHz): δ 9.04-9.02 (m, 2H), 8.49 (d, J=3.9 Hz, 1H), 8.31 (d, J=6.0 Hz, 1H), 8.24 (d, J=8.4 Hz, 1H), 7.94 (t, J=7.2 Hz, 1H), 7.73 (d, J=6.9 Hz, 1H), 7.62-7.57 (m, 2H), 7.22 (t, J=8.4 Hz, 1H), 7.06 (t, J=6.6 Hz, 1H), 6.98 (d, J=7.8 Hz, 2H), 6.80 (d, J=7.5 Hz, 1H), 4.83 (mc, 1H), 3.18-3.06 (m, 3H), 2.77-2.75 (m, 1H), 0.65 (m, 2H), 0.51 (m, 2H).

LCMS m/z [M+H]$^+$ C$_{32}$H$_{25}$N$_5$O$_3$S requires: 560.64. Found 560.08.

HPLC Tr (min), purity %: 3.36, 98%

Example 26

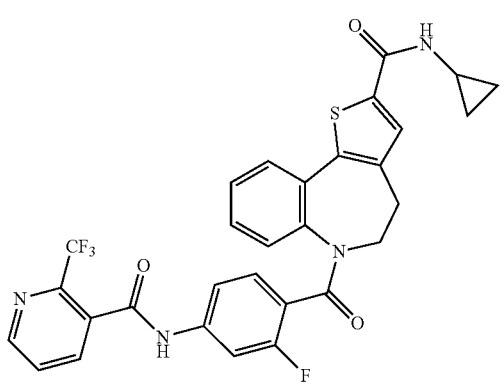 [SMILES: O=C(NC1CC1)c1cc2c(s1)-c1ccccc1N(C(=O)c1ccc(NC(=O)c3cccnc3C(F)(F)F)cc1F)CC2]

To a 50 mL flask containing 20 mL of DMF was added 1 mL of oxalyl chloride slowly and stirred for 10 min at RT. 100 mg of the carboxylic acid was dissolved in 2 mL of the above solution and stirred for 5 min at RT. Then 50 mg of P was dissolved in 1 mL pyridine and added to the above solution. The reaction was completed in 5 min at RT and quenched with 1 mL NH$_4$OH. The solvent was then evaporated under vacuum and the residue dissolved in CH$_3$CN and water and purified with prep HPLC (0% to 95% water/Acetonitrile) to afford 26 (26.7 mg, 54%).

$^1$H-NMR (DMSO, 300 MHz): δ 8.52 (d, J=3.9 Hz, 1H), 7.87 (d, J=7.5 Hz, 1H), 7.72 (d, J=7.5 Hz, 1H), 7.64-7.43 (m, 3H), 7.24 (t, J=7.5 Hz, 1H), 7.15 (t, J=8.1 Hz, 1H), 7.08 (t, J=7.2 Hz, 1H), 6.90 (d, J=7.5 Hz, 1H), 4.86-4.81 (m, 1H), 3.34-3.04 (m, 3H), 2.84-2.78 (m, 1H), 0.65 (m, 2H), 0.51 (m, 2H).

LCMS m/z [M+H]$^+$ C$_{30}$H$_{22}$F$_4$N$_4$O$_3$S requires: 595.58. Found 595.00.

HPLC Tr (min), purity %: 3.33, 98%

Example 27

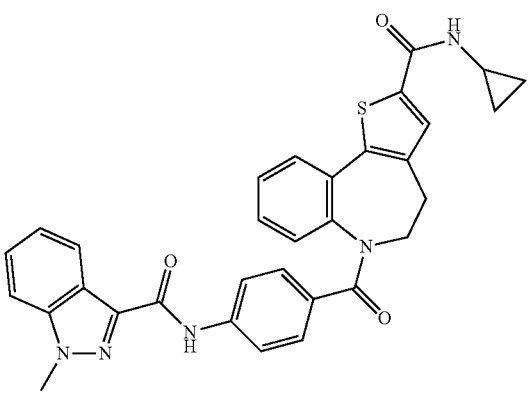 [SMILES: Cn1nc(C(=O)Nc2ccc(C(=O)N3CCc4cc(C(=O)NC5CC5)sc4-c4ccccc43)cc2)c2ccccc21]

To a 50 mL flask containing 20 mL of DMF was added 1 mL of oxalyl chloride slowly and stirred for 10 min at RT. 100 mg of 1-Methyl-1H-indazole-3-carboxylic acid was dissolved in 2 mL of the above solution and stirred for 5 min at RT. Then 50 mg of E was dissolved in 1 mL pyridine and added to the above solution. The reaction was completed in 5 min at RT and quenched with 1 mL NH$_4$OH. The solvent was evaporated under vacuum and the residue dissolved in CH$_3$CN and water and purified with prep HPLC (0% to 95% water/Acetonitrile) to afford 27 (32 mg, 43%).

$^1$H-NMR (DMSO, 300 MHz): δ 10.37 (s, 1H), 8.50 (s, 1H), 8.10 (d, J=6.9 Hz, 1H), 7.72-7.64 (m, 4H), 7.40 (s, 1H), 7.26-7.23 (m, 2H), 7.04-6.80 (m, 4H), 4.85 (mc, 1H), 4.12 (s, 3H), 3.22-3.10 (m, 3H), 2.78-2.70 (m, 1H), 0.66 (m, 2H), 0.52 (m, 2H).

LCMS m/z [M+H]$^+$ C$_{32}$H$_{27}$N$_5$O$_3$S requires: 561.65. Found 562.04.

HPLC Tr (min), purity %: 3.46, 98%

Example 28

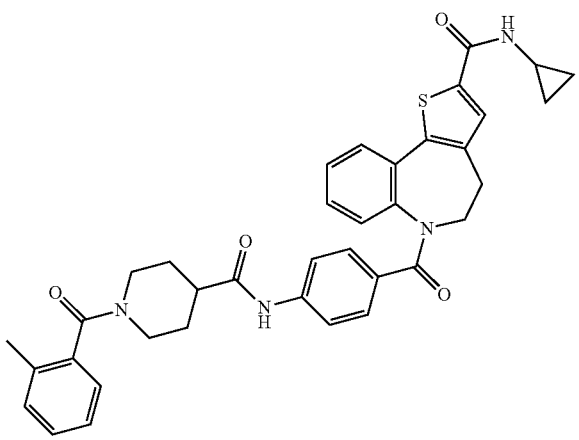 [SMILES: Cc1ccccc1C(=O)N1CCC(C(=O)Nc2ccc(C(=O)N3CCc4cc(C(=O)NC5CC5)sc4-c4ccccc43)cc2)CC1]

To a 50 mL flask containing 20 mL of DMF was added 1 mL of oxalyl chloride slowly and stirred for 10 min at RT. 100 mg of 1-(2-Methyl-benzoyl)-piperidine-4-carboxylic acid was dissolved in 2 mL of the above solution and stirred for 5 min at RT. Then 50 mg of E was dissolved in 1 mL pyridine and added to the above solution. The reaction was completed in 5 min at RT and quenched with 1 mL NH$_4$OH. The solvent was then evaporated under vacuum and the residue dissolved in CH₃CN and water and purified with prep HPLC (0% to 95% water/Acetonitrile) to afford 28 (51 mg, 65%).

¹H-NMR (DMSO, 300 MHz): δ 10.02 (s, 1H), 8.54 (d, J=4.2 Hz, 1H), 7.75 (d, J=8.4 Hz, 1H), 7.64 (s, 1H), 7.37 (d, J=8.1 Hz, 2H), 7.31-7.10 (m, 3H), 7.08-7.03 (m, 2H), 6.92 (d, J=7.5 Hz, 1H), 6.78 (d, J=6.9 Hz, 1H), 4.85 (mc, 1H), 4.54 (d, J=12.0 Hz, 1H), 3.43-2.99 (m, 4H), 2.95-2.79 (m, 1H), 2.49 (s, 3H), 2.18 (d, J=10.8 Hz, 2H), 1.86 (d, J=11.4 Hz, 2H), 1.64-1.50 (m, 2H), 0.69 (m, 2H), 0.55 (m, 2H).

LCMS m/z [M+H]⁺ C₃₇H₃₆N₄O₄S requires: 633.77. Found 633.92.

HPLC Tr (min), purity %: 3.13, 98%

Example 29

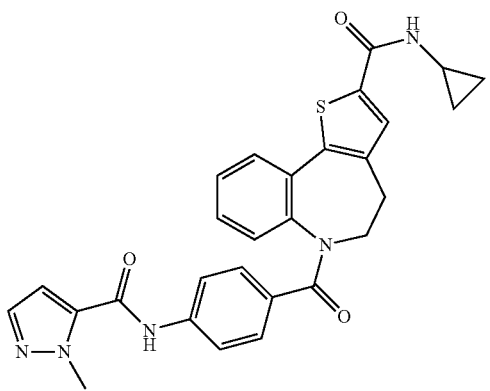 [SMILES: Cn1nccc1C(=O)Nc1ccc(C(=O)N2CCc3cc(C(=O)NC4CC4)sc3-c3ccccc32)cc1]

To a 50 mL flask containing 20 mL of DMF was added 1 mL of oxalyl chloride slowly and stirred for 10 min at RT. 100 mg of 2-Methyl-2H-pyrazole-3-carboxylic acid was dissolved in 2 mL of the above solution and stirred for 5 min at RT. Then 50 mg of E was dissolved in 1 mL pyridine and added to the above solution. The reaction was completed in 5 min at RT and quenched with 1 mL NH₄OH. The solvent was then evaporated under vacuum and the residue dissolved in CH₃CN and water and purified with prep HPLC (0% to 95% water/Acetonitrile) to afford 29 (29 mg, 46%).

¹H-NMR (DMSO, 300 MHz): δ 10.23 (s, 1H), 8.54 (d, J=3.9 Hz, 1H), 7.77 (d, J=6.9 Hz, 1H), 7.66 (s, 1H), 7.52 (d, J=7.8 Hz, 2H), 7.26 (t, J=6.6 Hz, 1H), 7.08 (t, J=7.8 Hz, 1H), 6.99-6.91 (m, 3H), 6.82 (d, J=7.2 Hz, 1H), 4.87 (mc, 1H), 4.03 (s, 3H), 3.22-3.10 (m, 3H), 2.83-2.80 (m, 1H), 0.70 (m, 2H), 0.56 (m, 2H).

LCMS m/z [M+H]⁺ C₂₈H₂₅N₅O₃S requires: 512.59. Found 512.12.

HPLC Tr (min), purity %: 2.95, 98%

Example 30

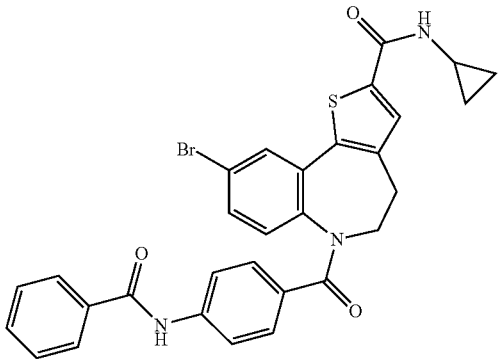 [SMILES: O=C(Nc1ccc(C(=O)N2CCc3cc(C(=O)NC4CC4)sc3-c3cc(Br)ccc32)cc1)c1ccccc1]

To a 50 mL flask containing 20 mL of DMF was added 1 mL of oxalyl chloride slowly and stirred for 10 min at RT. 100 mg of the benzoic acid was dissolved in 2 mL of the above solution and stirred for 5 min at RT. Then 50 mg of Q was dissolved in 1 mL pyridine and added to the above solution. The reaction was completed in 5 min at RT and quenched with 1 mL NH₄OH. The solvent was then evaporated under vacuum and the residue dissolved in CH₃CN and water and purified with prep HPLC (0% to 95% water/Acetonitrile) to afford 30 (10 mg, 8.5%).

¹H-NMR (DMSO, 300 MHz): δ 10.28 (s, 1H), 8.54 (d, J=3.6 Hz, 1H), 7.84 (d, J=7.5 Hz, 3H), 7.62-7.43 (m, 5H), 7.24 (d, J=9.6 Hz, 1H), 6.95 (d, J=7.5 Hz, 2H), 6.76 (d, J=7.8 Hz, 1H), 4.83 (mc, 1H), 3.15-3.07 (m, 3H), 2.77-2.76 (m, 1H), 0.65 (m, 2H), 0.51 (m, 2H).

LCMS m/z [M+H]⁺ C₃₀H₂₄BrN₃O₃S requires: 587.50. Found 587.99.

HPLC Tr (min), purity %: 2.55, 98%

Example 31

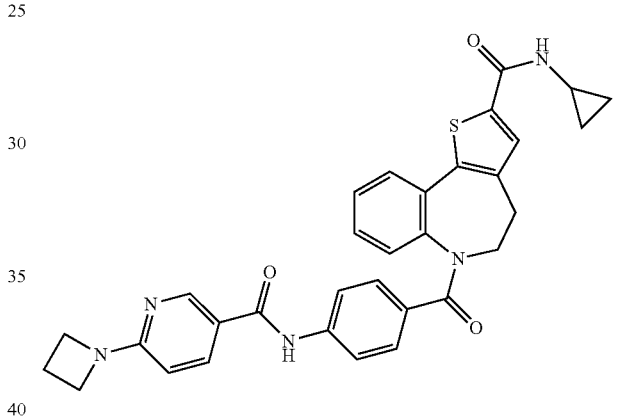

To a 50 mL flask containing 20 mL of DMF was added 1 mL of oxalyl chloride slowly and stirred for 10 min at RT. 100 mg of 2-bromo-5-pyridinecarboxylic acid was dissolved in 2 mL of the above solution and stirred for 5 min at RT. Then 50 mg of intermediate E was dissolved in 1 mL pyridine and added to the above solution. The reaction was completed in 5 min at RT. The solvent was then evaporated under vacuum, water added and the precipitate filtered. The precipitate was then dissolved in azetidine (1 mL) and stirred at RT for 2 h. Volatiles were removed under reduced pressure and the residue dissolved in CH₃CN and water and purified with prep HPLC (0% to 95% water/Acetonitrile) to afford 31 (24.6 mg, 20%).

¹H-NMR (DMSO, 300 MHz): δ 10.15 (s, 1H), 8.55 (s, 1H), 8.09 (d, J=9.3 Hz, 1H), 7.77 (d, J=7.5 Hz, 1H), 7.66 (s, 1H), 7.53 (d, J=8.7 Hz, 1H), 7.25 (t, J=7.5 Hz, 1H), 7.07 (t, J=7.5 Hz, 1H), 6.97 (d, J=7.8 Hz, 1H), 6.82 (d, J=9.1 Hz, 1H), 6.58 (d, J=9.6 Hz, 1H), 4.87 (mc, 1H), 4.16-3.97 (m, 5H), 3.21-3.11 (m, 3H), 2.81-2.80 (m, 1H), 2.39-2.36 (m, 1H), 0.70 (m, 2H), 0.56 (m, 2H).

LCMS m/z [M+H]⁺ C₃₂H₂₉N₅O₃S requires: 564.67. Found 564.14.

HPLC Tr (min), purity %: 2.58, 98%

Example 32

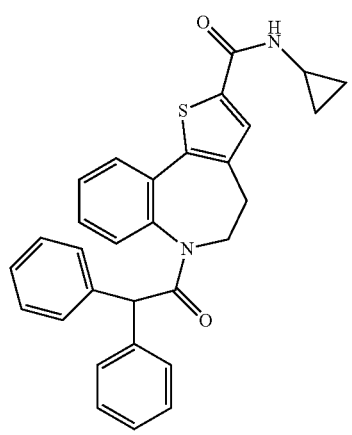 [SMILES: O=C(NC1CC1)c1cc2c(s1)-c1ccccc1N(C(=O)C(c1ccccc1)c1ccccc1)CC2]

To a 50 mL flask containing 20 mL of DMF was added 1 mL of oxalyl chloride slowly and stirred for 10 min at RT. The 2,2-diphenyl-acetic acid was dissolved in 2 mL of the above solution and stirred for 5 min at RT. Then 50 mg of intermediate C was dissolved in 1 mL pyridine and added to the above solution. The reaction was completed in 5 min at RT and quenched with NH$_4$OH (1 mL). Volatiles were removed under reduced pressure and the residue dissolved in CH$_3$CN and water and purified with prep HPLC (0% to 95% water/Acetonitrile) to afford 32 (40 mg, 20%).

$^1$H-NMR (DMSO, 300 MHz): δ 8.41 (d, J=3.9 Hz, 1H), 7.60-7.52 (m, 1H), 7.44 (s, 1H), 7.37-7.34 (m, 3H), 7.27-7.15 (m, 4H), 6.95-6.82 (m, 3H), 6.50 (d, J=7.5 Hz, 2H), 5.07 (s, 1H), 4.59-4.55 (m, 1H), 3.25-3.20 (m, 1H), 3.05-2.96 (m, 1H), 2.89-2.76 (m, 1H), 0.65 (m, 2H), 0.51 (m, 2H).

LCMS m/z [M+H]$^+$ C$_{30}$H$_{26}$N$_2$O$_2$S requires: 479.60. Found 479.10.

HPLC Tr (min), purity %: 2.63, 98%

Example 33

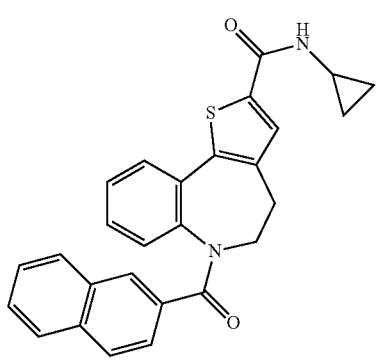 [SMILES: O=C(NC1CC1)c1cc2c(s1)-c1ccccc1N(C(=O)c1ccc3ccccc3c1)CC2]

Intermediate C (100 mg) and naphthalene-2-carbonyl chloride (50 mg) was dissolved in pyridine (2 mL) and the reaction mixture was stirred for 30 min. The reaction was quenched with water and extracted with EtOAc (20 mL). The solvent was evaporated and the residue was purified with preparative HPLC (0% to 95% water/Acetonitrile) to afford 33 (70 mg, 65%).

$^1$H-NMR (DMSO, 300 MHz): δ 8.52 (d, J=3.9 Hz, 1H), 7.72 (d, J=7.8 Hz, 1H), 7.77-7.61 (m, 6H), 7.48-7.40 (m, 2H), 7.15 (d, J=7.2 Hz, 1H), 6.92 (d, J=8.1 Hz, 2H), 6.78 (d, J=7.8 Hz, 1H), 4.87 (mc, 1H), 4.01 (s, 2H), 3.36-3.04 (m, 3H), 2.80-2.74 (m, 1H), 0.66 (m, 2H), 0.52 (m, 2H).

LCMS m/z [M+H]$^+$ C$_{27}$H$_{22}$N$_2$O$_2$S requires: 439.54. Found 439.13.

HPLC Tr (min), purity %: 3.21, 98%

Example 34

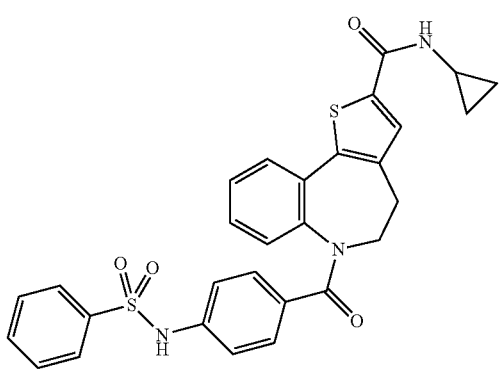 [SMILES: O=C(NC1CC1)c1cc2c(s1)-c1ccccc1N(C(=O)c1ccc(NS(=O)(=O)c3ccccc3)cc1)CC2]

To a 50 mL flask containing 20 mL of DMF was added 1 mL of oxalyl chloride slowly and stirred for 10 min at RT. 100 mg of the phenyl sulfonic acid was dissolved in 2 mL of the above solution and stirred for 5 min at RT. Then 50 mg of E was dissolved in 1 mL pyridine and added to the above solution. The reaction was completed in 5 min at RT and quenched with 1 mL NH$_4$OH. The solvent was then evaporated under vacuum and the residue dissolved in CH$_3$CN and water and purified with prep HPLC (0% to 95% water/Acetonitrile) to afford 34 (32 mg, 43%).

$^1$H-NMR (DMSO, 300 MHz): δ 10.39 (s, 1H), 8.47 (d, J=3.9 Hz, 1H), 7.68 (d, J=6.9 Hz, 1H), 7.63-7.43 (m, 6H), 7.19 (t, J=7.5 Hz, 1H), 6.94 (t, J=7.2 Hz, 2H), 6.80 (s, 1H), 6.66-6.60 (m, 1H), 4.76 (mc, 1H), 3.11-2.96 (m, 3H), 2.77-2.72 (m, 1H), 0.64 (m, 2H), 0.51 (m, 2H).

LCMS m/z [M+H]$^+$ C$_{29}$H$_{25}$N$_3$O$_4$S$_2$ requires: 544.66. Found 544.09.

HPLC Tr (min), purity %: 2.35, 98%

Example 35

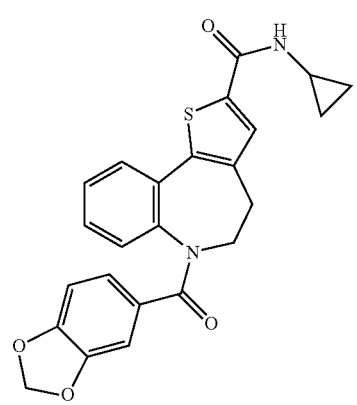 [SMILES: O=C(NC1CC1)c1cc2c(s1)-c1ccccc1N(C(=O)c1ccc3c(c1)OCO3)CC2]

To a 50 mL flask containing 20 mL of DMF was added 1 mL of oxalyl chloride slowly and stirred for 10 min at RT. 100 mg of benzo[1,3]dioxole-5-carboxylic acid was dissolved in 2 mL of the above solution and stirred for 5 min at RT. Then 50 mg of C was dissolved in 1 mL pyridine and added to the above solution. The reaction was completed in 2 h at RT and quenched with 1 mL NH$_4$OH. The solvent was then evaporated under vacuum and the residue dissolved in CH$_3$CN and water and purified with prep HPLC (0% to 95% water/Acetonitrile) to afford 35 (67 mg, 86%).

$^1$H-NMR (DMSO, 300 MHz): δ 8.48 (d, J=3.3 Hz, 1H), 7.70 (d, J=7.5 Hz, 1H), 7.60 (s, 1H), 7.21 (t, J=7.2 Hz, 2H), 7.06 (t, J=7.5 Hz, 1H), 6.81 (d, J=7.8 Hz, 1H), 6.64 (d, J=8.1 Hz, 1H), 6.53 (s, 1H), 6.36 (d, J=8.4 Hz, 1H), 5.92 (s, 2H), 4.79 (mc, H), 3.14 (m, 3H), 2.78-2.72 (m, 1H), 0.64 (m, 2H), 0.51 (m, 2H).

LCMS m/z [M+H]$^+$ C$_{24}$H$_{20}$N$_2$O$_4$S requires: 433.49. Found 433.05.

Example 36

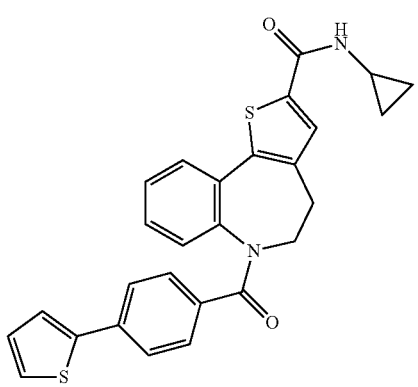 [SMILES: O=C(NC1CC1)c1cc2c(s1)-c1ccccc1N(C(=O)c1ccc(-c3cccs3)cc1)CC2]

To a 50 mL flask containing 20 mL of DMF was added 1 mL of oxalyl chloride slowly and stirred for 10 min at RT. 100 mg of 4-thiophen-2-yl-benzoic acid was dissolved in 2 mL of the above solution and stirred for 5 min at RT. Then 50 mg of C was dissolved in 1 mL pyridine and added to the above solution. The reaction was completed in 2 h at RT and quenched with 1 mL NH$_4$OH. The solvent was then evaporated under vacuum and the residue dissolved in CH$_3$CN and water and purified with prep HPLC (0% to 95% water/Acetonitrile) to afford 36 (31.8 mg, 25%).

$^1$H-NMR (DMSO, 300 MHz): δ 8.55 (d, J=3.9 Hz, 1H), 7.77 (d, J=7.5 Hz, 1H), 7.67 (s, 1H), 7.55 (d, J=4.8 Hz, 1H), 7.50-7.47 (m, 3H), 7.26 (d, J=7.5 Hz, 1H), 7.11-7.00 (m, 4H), 6.87 (d, J=9.1 Hz, 1H), 4.88 (mc, 1H), 3.29-3.06 (m, 3H), 2.86-2.78 (m, 1H), 0.70 (m, 2H), 0.57 (m, 2H).

LCMS m/z [M+H]$^+$ C$_{27}$H$_{22}$N$_2$O$_2$S$_2$ requires: 471.61. Found 471.00.

HPLC Tr (min), purity %: 2.59, 98%

Example 37

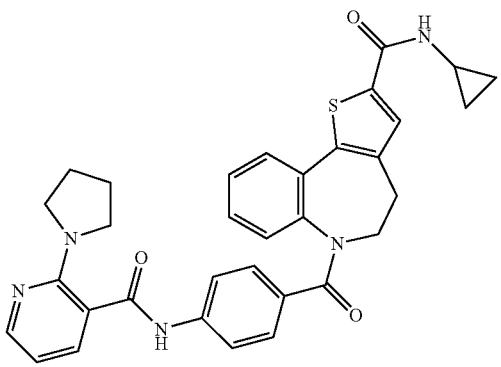 [SMILES: O=C(NC1CC1)c1cc2c(s1)-c1ccccc1N(C(=O)c1ccc(NC(=O)c3cccnc3N3CCCC3)cc1)CC2]

Compound 1 (15 mg) and pyrrolidine (25 mg) were dissolved in DMF (1 mL) and triethylamine (0.5 mL). The reaction mixture was stirred at 70° C. for 16 h. Volatiles were removed under reduced pressure at 40° C. and the resulting residue was purified by preparative HPLC (0% to 95% water/Acetonitrile) to afford 37 (7.6 mg, 26%).

$^1$H-NMR (DMSO, 300 MHz): δ 8.54 (d, J=3.6 Hz, 1H), 8.12 (d, J=3.6 Hz, 1H), 7.81 (d, J=7.5 Hz, 1H), 7.76 (d, J=7.5 Hz, 1H), 7.48 (d, J=8.1 Hz, 1H), 7.26 (t, J=7.8 Hz, 1H), 7.09 (t, J=8.1 Hz, 1H), 6.99 (d, J=8.1 Hz, 1H), 6.84 (d, J=6.9 Hz, 1H), 6.76 (d, J=6.3 Hz, 1H), 4.82 (mc, 1H), 3.91-3.37 (m, 4H), 3.37-2.81 (m, 5H), 0.68 (mc, 2H), 0.55 (mc, 2H).

LCMS m/z [M+H]$^+$ C$_{33}$H$_{31}$N$_5$O$_3$S requires: 577.21. Found 578.23.

HPLC Tr (min), purity %: 3.01, 95%

Examples 38-46 follow the procedure for example 37 except substituting pyrollidine with the appropriate amine.

Example 38

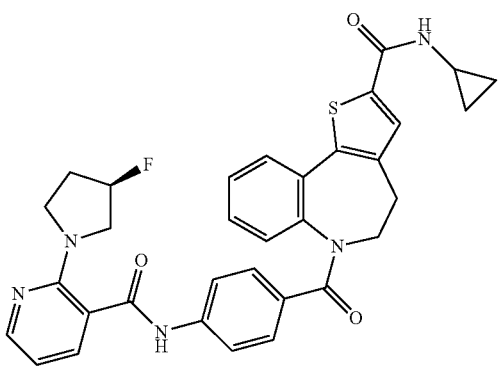 [SMILES: O=C(NC1CC1)c1cc2c(s1)-c1ccccc1N(C(=O)c1ccc(NC(=O)c3cccnc3N3CC[C@@H](F)C3)cc1)CC2]

Yield 83%

$^1$H-NMR (DMSO, 300 MHz): δ 10.57 (s, 1H), 8.54 (d, J=3.9 Hz, 1H), 8.18 (d, J=4.5 Hz, 1H), 7.75 (t, J=8.1 Hz, 2H), 7.65 (s, 1H), 7.49 (d, J=8.1 Hz, 1H), 7.27 (t, J=7.5 Hz, 1H), 7.10 (t, J=8.1 Hz, 1H), 6.99 (d, J=8.1 Hz, 1H), 6.75 (t, J=5.1 Hz, 1H), 5.44 (s, 1H), 5.27 (s, 1H), 4.88 (mc, 1H), 3.84-3.73 (m, 3H), 3.20-3.10 (m, 4H), 2.82-2.79 (m, 1H), 2.20-2.12 (m, 1H), 0.70 (m, 2H), 0.55 (m, 2H).

LCMS [M+H]+ C33H30FN5O3S requires: 595.69. Found 595.23.

HPLC Tr (min), purity %: 3.21, 98%

Example 39

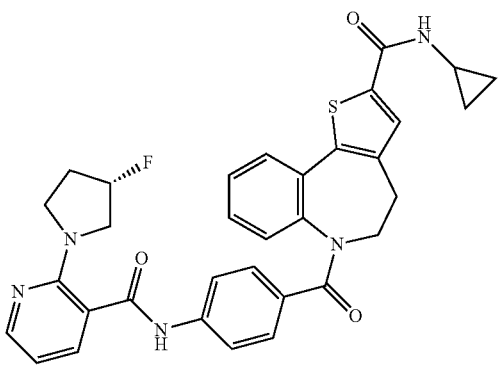 [SMILES: O=C(NC1CC1)c1cc2c(s1)-c1ccccc1N(C(=O)c1ccc(NC(=O)c3cccnc3N3CC[C@H](F)C3)cc1)CC2]

Yield 87%

¹H-NMR (DMSO, 300 MHz): δ 10.57 (s, 1H), 8.49 (d, J=3.9 Hz, 1H), 8.13 (d, J=5.1 Hz, 1H), 7.72 (t, J=8.1 Hz, 2H), 7.60 (s, 1H), 7.44 (d, J=8.1 Hz, 1H), 7.22 (t, J=7.5 Hz, 1H), 7.05 (t, J=8.1 Hz, 1H), 6.94 (d, J=8.1 Hz, 1H), 6.67 (t, J=5.1 Hz, 1H), 5.38 (s, 1H), 5.21 (s, 1H), 4.83 (mc, 1H), 3.74-3.62 (m, 3H), 3.15-3.10 (m, 4H), 2.79-2.70 (m, 1H), 2.16-2.12 (m, 1H), 0.65 (m, 2H), 0.50 (m, 2H).

LCMS m/z [M+H]+ C33H30FN5O3S requires: 595.69. Found 595.23.

HPLC Tr (min), purity %: 3.21, 98%

Example 40

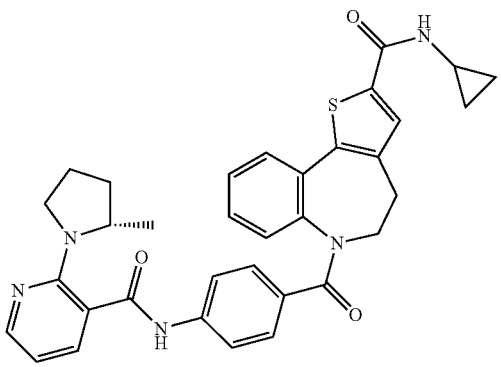 [SMILES: C[C@H]1CCCN1c1ncccc1C(=O)Nc1ccc(C(=O)N2CCc3cc(C(=O)NC4CC4)sc3-c3ccccc32)cc1]

Yield 96%

¹H-NMR (DMSO, 300 MHz): δ 10.52 (s, 1H), 8.49 (d, J=3.9 Hz, 1H), 8.08 (d, J=5.1 Hz, 1H), 7.72 (t, J=7.8 Hz, 2H), 7.61 (s, 1H), 7.43 (d, J=8.1 Hz, 2H), 7.22 (t, J=7.8 Hz, 1H), 7.05 (t, J=7.5 Hz, 1H), 6.94 (d, J=7.8 Hz, 2H), 6.71 (t, J=7.5 Hz, 1H), 4.83 (mc, 1H), 4.21 (dd, J=6.0, 12.3 Hz, 1H), 3.66-3.37 (m, 2H), 3.16-3.00 (m, 3H), 2.76-2.48 (m, 1H), 2.03-1.97 (m, 1H), 1.85-1.72 (m, 1H), 1.70-1.67 (m, 1H), 1.54-1.50 (m, 1H), 1.12 (d, J=6.3 Hz, 1H), 0.65 (m, 2H), 0.50 (m, 2H).

LCMS m/z [M+H]+ C34H33N5O3S requires: 591.72. Found 591.68.

HPLC Tr (min), purity %: 3.25, 98%

Example 41

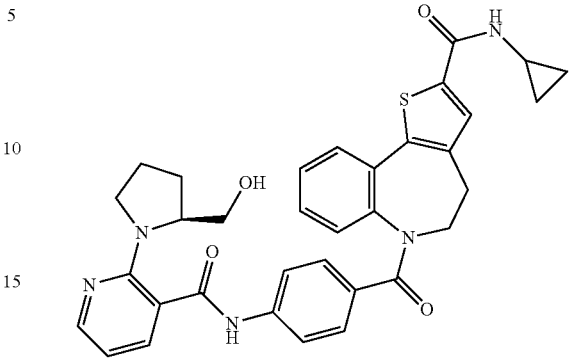

Yield 98%

¹H-NMR (DMSO, 300 MHz): δ 10.43 (s, 1H), 8.54 (d, J=3.9 Hz, 1H), 8.14 (d, J=4.8 Hz, 1H), 7.77 (d, J=7.8 Hz, 1H), 7.72 (d, J=7.2 Hz, 1H), 7.65 (s, 1H), 7.47 (d, J=8.4 Hz, 2H), 7.27 (t, J=7.5 Hz, 1H), 7.10 (t, J=7.5 Hz, 1H), 6.98 (d, J=8.1 Hz, 2H), 6.85 (d, J=6.9 Hz, 1H), 6.74 (t, J=7.2 Hz, 1H), 4.87 (mc, 1H), 4.31 (s, 1H), 3.12-3.10 (m, 3H), 2.81-2.77 (m, 1H), 1.89-1.83 (m, 4H), 1.75-1.68 (m, 2H), 0.70 (m, 2H), 0.55 (m, 2H).

LCMS m/z [M+H]+ C35H35N5O3S requires: 622.75. Found 622.18.

HPLC Tr (min), purity %: 3.21, 98%

Example 42

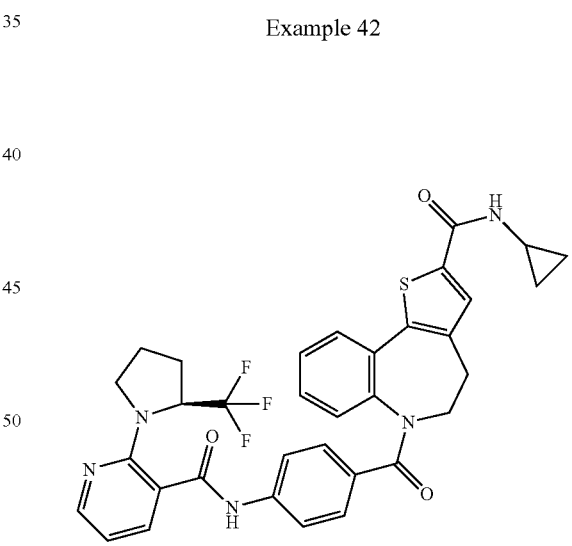

Yield 34%

¹H-NMR (DMSO, 300 MHz): δ 10.55 (s, 1H), 8.55 (d, J=3.6 Hz, 1H), 8.23 (d, J=3.6 Hz, 1H), 7.75 (t, J=7.2 Hz, 2H), 7.66 (s, 1H), 7.49 (d, J=8.1 Hz, 1H), 7.27 (t, J=7.8 Hz, 1H), 7.10 (t, J=8.1 Hz, 1H), 7.00 (d, J=8.1 Hz, 1H), 6.87 (t, J=6.9 Hz, 1H), 5.55 (mc, 1H), 3.15-3.05 (m, 3H), 2.82-2.75 (m, 1H), 3.37-2.81 (m, 5H), 0.69 (m, 2H), 0.55 (m, 2H).

LCMS m/z [M+H]+ C34H30F3N5O3S requires: 646.69. Found 646.20.

HPLC Tr (min), purity %: 3.25, 98%

Example 43

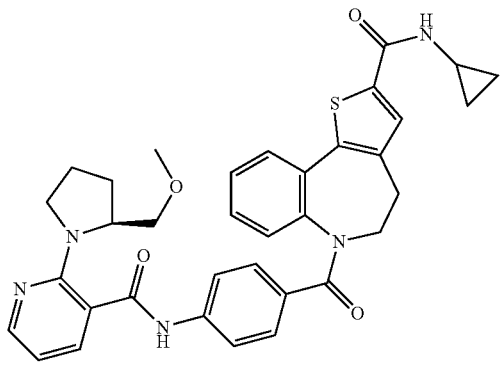 [SMILES: COC[C@@H]1CCCN1c1ncccc1C(=O)Nc1ccc(C(=O)N2CCc3cc(C(=O)NC4CC4)sc3-c3ccccc32)cc1]

Yield 95%

$^1$H-NMR (DMSO, 300 MHz): δ 10.49 (s, 1H), 8.54 (d, J=3.3 Hz, 1H), 8.11 (d, J=3.3 Hz, 1H), 7.76 (d, J=7.5 Hz, 1H), 7.65 (s, 2H), 7.47 (d, J=7.5 Hz, 2H), 7.27 (t, J=7.5 Hz, 1H), 7.09 (t, J=7.5 Hz, 1H), 6.98 (d, J=8.1 Hz, 2H), 6.86 (mc, 1H), 6.72-6.68 (m, 1H), 4.87 (mc, 1H), 4.42 (s, 1H), 3.19-3.11 (m, 3H), 2.0 (s, 1H), 2.01-1.83 (m, 2H), 0.70 (m, 2H), 0.55 (m, 2H).

LCMS m/z [M+H]$^+$ $C_{35}H_{35}N_5O_3S$ requires: 622.75. Found 622.18.

HPLC Tr (min), purity %: 3.21, 98%

Example 44

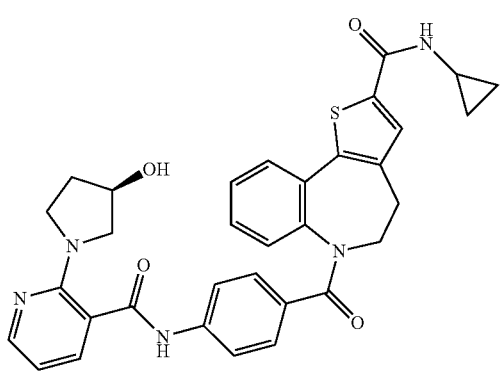 [SMILES: O=C(NC1CC1)c1cc2c(s1)-c1ccccc1N(C(=O)c1ccc(NC(=O)c3cccnc3N3CC[C@@H](O)C3)cc1)CC2]

Yield 94%

$^1$H-NMR (DMSO, 300 MHz): δ 10.59 (s, 1H), 8.54 (d, J=3.3 Hz, 1H), 8.13 (d, J=4.8 Hz, 1H), 7.77 (d, J=7.5 Hz, 2H), 7.66 (s, 1H), 7.49 (d, J=7.8 Hz, 2H), 7.25 (t, J=7.5 Hz, 1H), 7.10 (t, J=7.5 Hz, 1H), 6.99 (d, J=8.1 Hz, 2H), 6.85 (d, J=6.9 Hz, 1H), 6.75 (t, J=7.2 Hz, 1H), 4.87 (mc, 1H), 4.30 (s, 1H), 3.21-3.11 (m, 7H), 2.81-2.77 (m, 1H), 1.89-1.83 (m, 2H), 0.70 (m, 2H), 0.55 (m, 2H).

LCMS m/z [M+H]$^+$ $C_{33}H_{31}N_5O_4S$ requires: 593.70. Found 593.68.

HPLC Tr (min), purity %: 2.98, 98%

Example 45

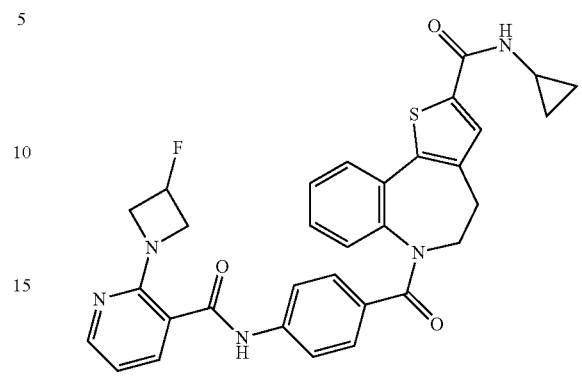

Yield 38%

$^1$H-NMR (DMSO, 300 MHz): δ 10.47 (s, 1H), 8.51 (d, J=3.3 Hz, 1H), 8.26 (d, J=3.3 Hz, 1H), 7.75 (d, J=7.5 Hz, 2H), 7.63 (s, 1H), 7.23 (t, J=7.8 Hz, 1H), 7.08 (t, J=7.2 Hz, 1H), 6.88-6.85 (m, 2H), 6.77 (d, J=7.5 Hz, 1H), 6.72 (d, J=8.1 Hz, 1H), 6.28 (d, J=8.7 Hz, 1H), 4.92 (mc, 1H), 4.32-4.20 (m, 4H), 4.14 (s, 1H), 3.19-3.10 (m, 3H), 2.79 (s, 1H), 0.69 (m, 2H), 0.56 (m, 2H).

LCMS m/z [M+H]$^+$ $C_{32}H_{28}FN_5O_3S$ requires: 582.66. Found 582.54.

HPLC Tr (min), purity %: 3.15, 98%

Example 46

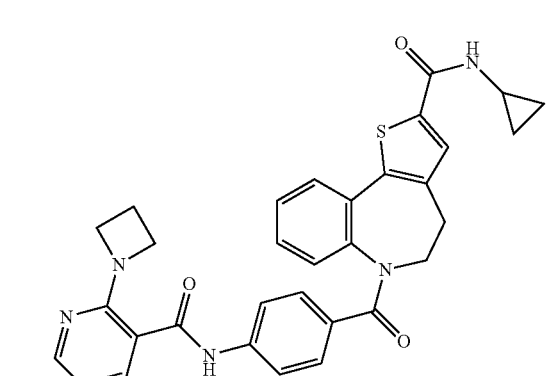

Yield 75%

$^1$H-NMR (DMSO, 300 MHz): δ 10.45 (s, 1H), 8.55 (s, 1H), 8.11 (d, J=3.3 Hz, 1H), 7.77 (d, J=7.5 Hz, 2H), 7.65 (s, 1H), 7.48 (d, J=8.1 Hz, 2H), 7.26 (t, J=8.1 Hz, 1H), 7.07-6.93 (m, 3H), 6.74 (t, J=6.9 Hz, 2H), 4.87 (mc, 1H), 4.33 (s, 1H), 3.93 (t, J=6.9 Hz, 2H), 3.11-3.05 (m, 3H), 2.81 (s, 1H), 2.30 (t, J=7.2 Hz, 1H), 2.08 (s, 1H), 0.70 (m, 2H), 0.55 (m, 2H).

LCMS m/z [M+H]$^+$ $C_{32}H_{29}N_5O_3S$ requires: 564.67. Found 564.31.

HPLC Tr (min), purity %: 2.53, 98%

Example 47

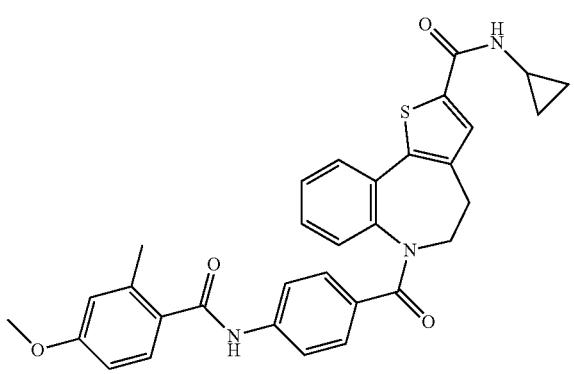 [SMILES: COc1ccc(C(=O)Nc2ccc(C(=O)N3CCc4cc(C(=O)NC5CC5)sc4-c4ccccc43)cc2)c(C)c1]

To a 50 mL flask containing 20 mL of DMF added 1 mL of oxalyl chloride slowly, an orange solution formed after the addition. 100 mg of 2-methyl-4-methoxybenzoic acid was dissolved in 2 mL of the above orange solution and stirred for 5 mins at room temperature. Then 50 mg of the intermediate E was dissolved in 1 mL pyridine and then this pyridine solution was added to the above orange carboxylic acid solution. Reaction was finished in 5 mins at room temperature and was quenched with 1 mL NH$_4$OH. The solvent was then evaporated under vacuum and the residue was dissolved in CH$_3$CN and water and purified with prep HPLC to afford 47 (19 mg, 28%).

$^1$H-NMR (DMSO, 300 MHz): δ 10.21 (s, 1H), 8.54 (d, J=3.3 Hz, 1H), 7.77 (d, J=7.5 Hz, 1H), 7.66 (s, 1H), 7.51 (d, J=7.8 Hz, 1H), 7.40 (d, J=8.4 Hz, 2H), 7.26 (d, J=7.8 Hz, 1H), 7.10 (t, J=7.8 Hz, 1H), 6.96 (d, J=8.1 Hz, 3H), 6.83-6.80 (m, 3H), 4.88-4.86 (m, 1H), 3.76 (s, 3H), 3.22-3.12 (m, 4H), 2.85-2.75 (m, 1H), 2.33 (s, 3H), 0.70 (m, 2H), 0.56 (m, 2H).

LCMS m/z [M+H]$^+$ C$_{32}$H$_{29}$N$_3$O$_4$S requires: 552.70. Found 552.05.

HPLC Tr (min), purity %: 3.23, 95%.
HPLC Tr (min), purity %: 3.23, 95%.

Example 48

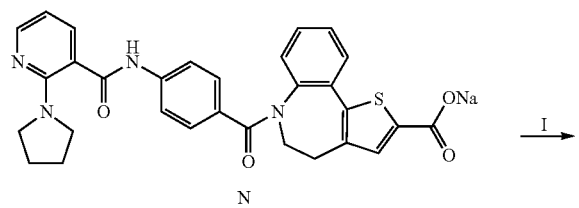
N

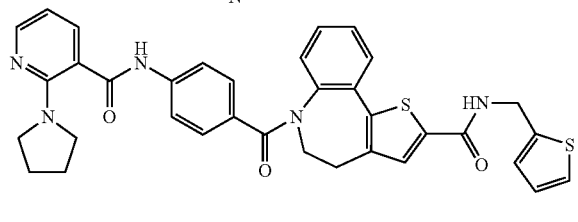
48

I. HATU, DIPEA, DMF, amine

Mixed N (12 mg, 0.02 mmol) with DMF (300 uL), DIPEA (5.5 uL, 0.03 mmol) and HATU (10 mg, 0.025 mmol). Added 2-aminomethylthiophene (0.026 mmol). Stirred for 3 hrs. Diluted reaction with acetonitrile and water and purified with prep HPLC to give 48.

$^1$H NMR (300 MHz, CD$_3$OD): δ 8.16 (m, 1H), 8.02 (m, 1H), 7.82 (m, 1H), 7.61 (s, 1H), 7.51 (m, 2H), 7.29 (m, 2H), 7.09-6.94 (m, 6H), 6.83 (m, 1H), 5.02 (m, 1H), 4.73 (s, 2H), 3.58 (m, 5H), 3.14 (m, 2H), 2.07 (m, 4H).

LC/MS (m/e): 634.1 [M+H]$^+$

The following examples 49-62 were prepared from intermediate N using the same procedure as described for 48 above except substituting the appropriate amine for instead of 2-aminomethyl thiophene.

Example 49

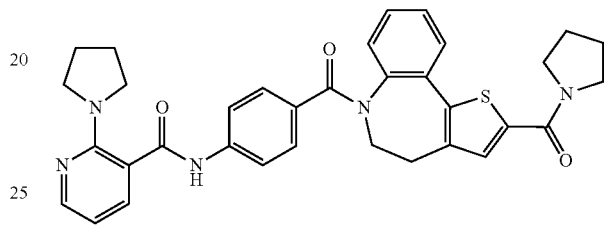

$^1$H NMR (300 MHz, CD$_3$OD): δ 8.13 (m, 1H), 7.83 (m, 1H), 7.66 (m, 1H), 7.59 (s, 1H), 7.51 (m, 2H), 7.29 (m, 1H), 7.09 (m, 3H), 6.87 (m, 1H), 6.66 (m, 1H), 5.02 (m, 1H), 3.86 (m, 2H), 3.65 (m, 2H), 3.41 (m, 5H), 3.12 (m, 2H), 1.90 (m, 4H), 2.02 (m, 8H).

LC/MS (m/e): 592.2 [M+H]$^+$

Example 50

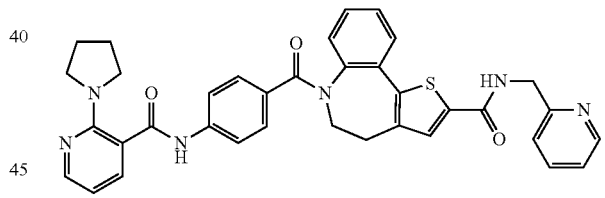

$^1$H NMR (300 MHz, CD$_3$OD): δ 8.77 (m, 1H), 8.49 (m 1H), 8.16 (m, 1H), 8.02 (m, 2H), 7.90 (m, 1H), 7.80 (m, 1H), 7.74 (s, 1H), 7.53 (m, 2H), 7.27 (m, 1H), 7.09 (m, 3H), 6.99 (m, 1H), 6.87 (m, 1H), 5.02 (m, 1H), 4.73 (s, 2H), 3.58 (m, 5H), 3.19 (m, 2H), 2.07 (m, 4H).

LC/MS (m/e): 629.1 [M+H]$^+$

Example 51

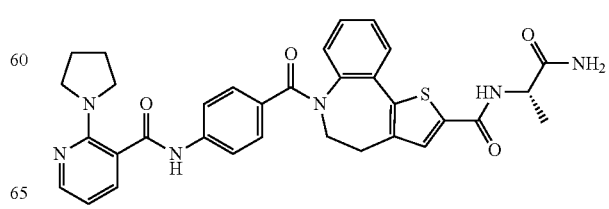

¹H NMR (300 MHz, CD₃OD): δ 8.17 (m, 1H), 8.02 (m, 1H), 7.80 (m, 1H), 7.73 (s, 1H), 7.52 (m, 2H), 7.28 (m, 1H), 7.11 (m, 3H), 6.99 (m, 1H), 6.87 (m, 1H), 5.02 (m, 1H), 4.56 (m, 1H), 3.58 (m, 5H), 319 (m, 2H), 2.07 (m, 4H), 1.51 (d, J=7.2 Hz, 3H).

LC/MS (m/e): 609.2 [M+H]⁺

Example 52

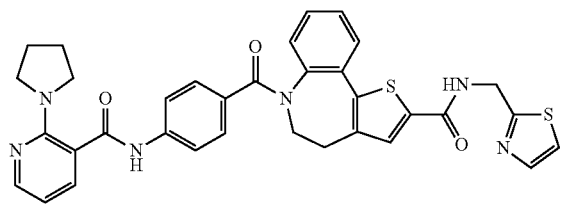 [SMILES: O=C(NCc1nccs1)c1cc2c(s1)-c1ccccc1N(C(=O)c1ccc(NC(=O)c3cccnc3N3CCCC3)cc1)CC2]

¹H NMR (300 MHz, CD₃OD): δ 8.17 (m, 1H), 8.02 (m, 1H), 7.84 (m, 1H), 7.75 (m, 1H), 7.67 (s, 1H), 7.53 (m, 3H), 7.27 (m, 1H), 7.11 (m, 3H), 6.99 (m, 1H), 6.88 (m, 1H), 5.02 (m, 1H), 4.88 (s, 2H), 3.58 (m, 5H), 3.18 (m, 2H), 2.08 (m, 4H).

LC/MS (m/e): 635.1 [M+H]⁺

Example 53

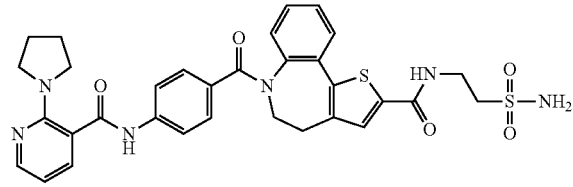 [SMILES: NS(=O)(=O)CCNC(=O)c1cc2c(s1)-c1ccccc1N(C(=O)c1ccc(NC(=O)c3cccnc3N3CCCC3)cc1)CC2]

¹H NMR (300 MHz, CD₃OD): δ 8.17 (m, 1H), 8.02 (m, 1H), 7.82 (m, 1H), 7.60 (s, 1H), 7.52 (m, 2H), 729 (m, 1H), 7.09 (m, 3H), 6.99 (m, 1H), 6.87 (m, 1H), 5.02 (m, 1H), 3.84 (m, 2H), 3.58 (m, 5H), 3.36 (m, 2H), 3.17 (m, 2H), 2.07 (m, 4H).

LC/MS (m/e): 6452 [M+H]⁺

Example 54

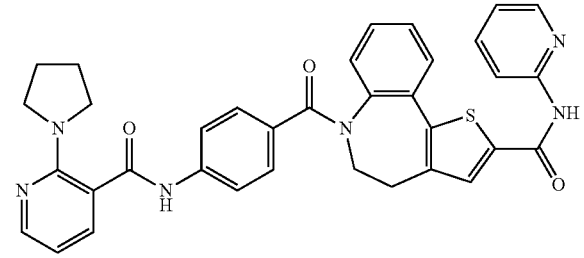 [SMILES: O=C(Nc1ccccn1)c1cc2c(s1)-c1ccccc1N(C(=O)c1ccc(NC(=O)c3cccnc3N3CCCC3)cc1)CC2]

¹H NMR (300 MHz, CD₃OD): δ 8.41 (m 1H), 8.16 (m, 2H), 8.00 (m, 3H), 7.89 (m, 1H), 7.54 (m, 2H), 7.33 (m, 2H), 7.13 (m, 3H), 6.99 (m, 1H), 6.92 (m, 1H), 5.02 (m, 1H), 3.58 (m, 5H), 3.19 (m, 2H), 2.07 (m, 4H).

LC/MS (m/e): 615.2 [M+H]⁺

Example 55

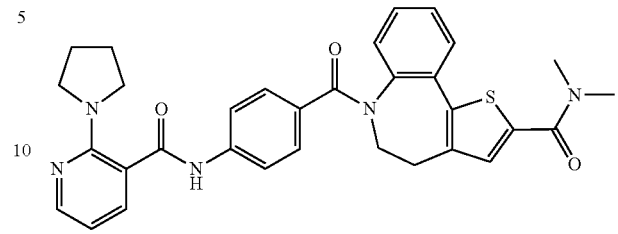

¹H NMR (300 MHz, CD₃OD): δ 8.18 (m, 1H), 8.01 (m, 1H), 7.82 (m, 1H), 7.53 (m, 2H), 7.45 (s, 1H), 7.29 (m, 1H), 7.12 (m, 3H), 7.00 (m, 1H), 6.87 (m, 1H), 5.02 (m, 1H), 3.58 (m, 5H), 3.33 (m, 6H), 3.18 (m, 2H), 2.07 (m, 4H).

LC/MS (m/e): 566.2 [M+H]⁺

Example 56

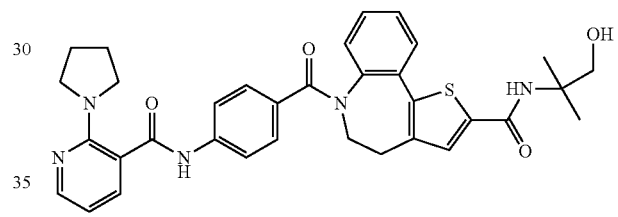

¹H NMR (300 MHz, CD₃OD): δ 8.17 (m, 1H), 8.02 (m, 1H), 7.82 (m, 1H), 7.64 (s, 1H), 7.52 (m, 2H), 7.29 (m, 1H), 7.08 (m, 3H), 7.00 (m, 1H), 6.87 (m, 1H), 5.02 (m, 1H), 3.70 (s, 2H), 3.58 (m, 5H), 3.08 (m, 2H), 2.08 (m, 4H), 1.42 (s, 6H).

LC/MS (m/e): 610.2 [M+H]⁺

Example 57

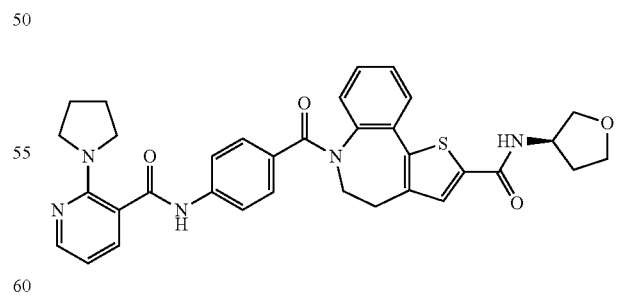

¹H NMR (300 MHz, CD₃OD): δ 8.17 (m, 1H), 8.00 (m, 1H), 7.83 (m, 1H), 7.68 (s, 1H), 7.50 (m, 2H), 7.29 (m, 1H), 7.09 (m, 3H), 7.00 (m, 1H), 6.85 (m, 1H), 5.00 (m, 1H), 4.57 (m, 1H), 3.96-3.76 (m, 3H), 3.58 (m, 5H), 3.17 (m, 2H), 2.30 (m, 1H), 2.07 (m, 4H).

LC/MS (m/e): 608.2 [M+H]⁺

Example 58

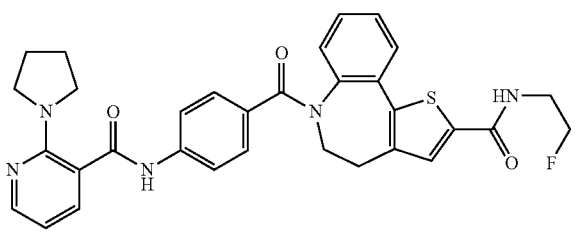 [SMILES: O=C(NCCF)c1cc2c(s1)-c1ccccc1N(C(=O)c1ccc(NC(=O)c3cccnc3N3CCCC3)cc1)CC2]

$^1$H NMR (300 MHz, CD$_3$OD): δ 8.17 (m, 1H), 8.02 (m, 1H), 7.83 (m, 1H), 7.64 (s, 1H), 7.52 (m, 2H), 7.30 (m, 1H), 7.09 (m, 3H), 7.00 (m, 1H), 6.88 (m, 1H), 5.02 (m, 1H), 4.65 (m, 1H), 4.51 (m, 1H), 3.72 (m, 1H), 3.63 (m, 1H), 3.58 (m, 5H), 3.12 (m, 1H), 2.07 (m, 4H).
LC/MS (m/e): 584.1 [M+H]$^+$

Example 59

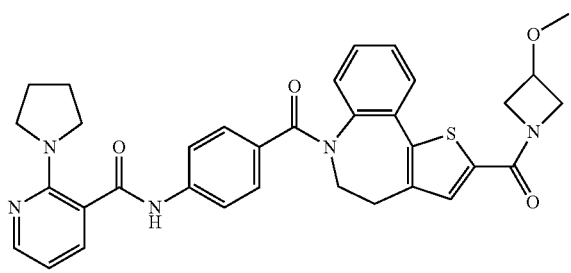 [SMILES: COC1CN(C(=O)c2cc3c(s2)-c2ccccc2N(C(=O)c2ccc(NC(=O)c4cccnc4N4CCCC4)cc2)CC3)C1]

$^1$H NMR (300 MHz, CD$_3$OD): δ 8.17 (m, 1H), 8.02 (m, 1H), 7.84 (m, 1H), 7.51 (m, 3H), 7.29 (m, 1H), 7.11 (m, 3H), 7.00 (m, 1H), 6.88 (m, 1H), 5.03 (m, 1H), 4.80 (m, 1H), 4.36 (m, 3H), 3.99 (m, 1H), 3.58 (m, 5H), 3.35 (m, 3H), 3.17 (m, 2H), 2.07 (m, 4H).
LC/MS (m/e): 608.2 [M+H]$^+$

Example 60

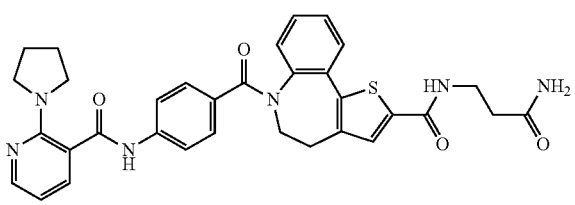 [SMILES: NC(=O)CCNC(=O)c1cc2c(s1)-c1ccccc1N(C(=O)c1ccc(NC(=O)c3cccnc3N3CCCC3)cc1)CC2]

$^1$H NMR (300 MHz, CD$_3$OD): δ 8.17 (m, 1H), 8.02 (m, 1H), 7.82 (m, 1H), 7.60 (s, 1H), 7.52 (m, 2H), 7.29 (m, 1H), 7.09 (m, 3H), 7.00 (m, 1H), 6.87 (m, 1H), 5.02 (m, 1H), 3.60 (m, 7H), 2.56 (m, 2H), 2.07 (m, 4H).
LC/MS (m/e): 609.2 [M+H]$^+$

Example 61

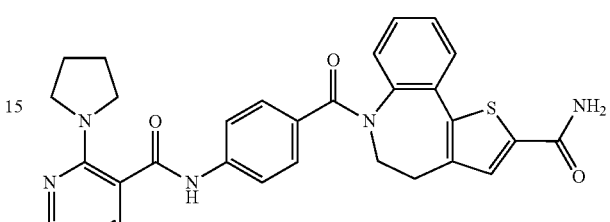

$^1$H NMR (300 MHz, CD$_3$OD): δ 8.17 (m, 1H), 8.02 (m, 1H), 7.83 (m, 1H), 7.64 (s, 1H), 7.52 (m, 2H), 7.29 (m, 1H), 7.12 (m, 3H), 7.00 (m, 1H), 6.88 (m, 1H), 5.01 (m, 1H), 3.60 (m, 6H), 3.17 (m, 1H), 2.08 (m, 4H).
LC/MS (m/e): 538.2 [M+H]$^+$

Example 62

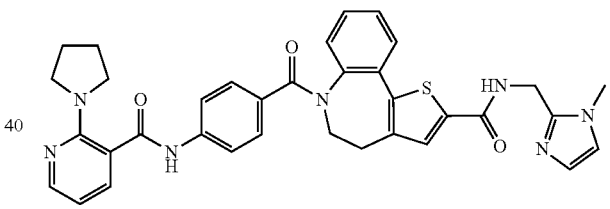

$^1$H NMR (300 MHz, CD$_3$OD): δ 8.16 (m, 1H), 8.03 (m, 1H), 7.83 (m, 1H), 7.70 (s, 1H), 7.53 (m, 3H), 7.30 (m, 1H), 7.11 (m, 3H), 6.99 (m, 1H), 6.89 (m, 1H), 5.02 (m, 1H), 4.85 (s, 2H), 3.70 (s, 3H), 3.58 (m, 6H), 3.18 (m, 2H), 2.08 (m, 4H).
LC/MS (m/e): 632.1 [M+H]$^+$

Example 63

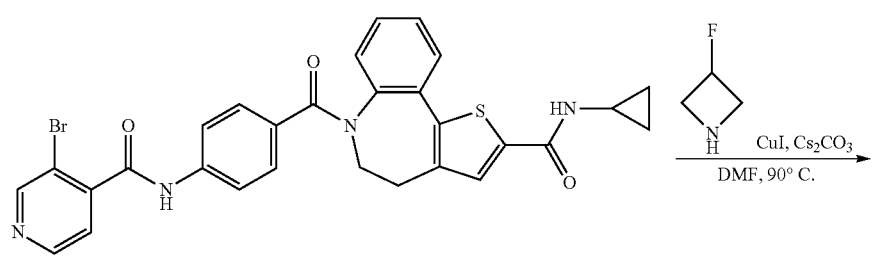

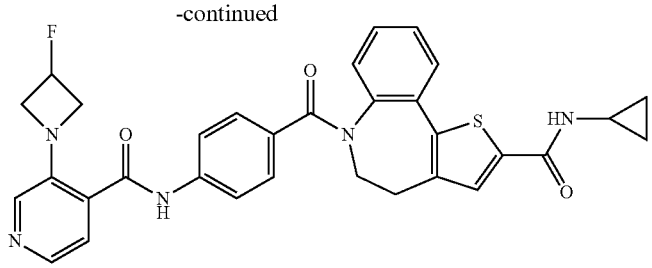

63

Intermediate R (15 mg) and 3-fluoroazetidine (6 mg) were dissolved in DMF (1 mL). To the above solution CuI (5 mg) and Cesium Carbonate (25 mg) were added. The reaction mixture was stirred at 90° C. overnight. Volatiles were removed under reduced pressure at 40° C. and the resulting residue was purified by preparative HPLC (0% to 95% water/Acetonitrile) to afford 63 (6 mg, 40%) as a yellow powder.

$^1$H-NMR (DMSO, 300 MHz): δ 8.92 (s, 1H), 8.40 (d, J=4.2 Hz, 1H), 7.75 (t, J=7.2 Hz, 1H), 7.62 (t, J=8.1 Hz, 1H), 7.42 (d, J=8.1 Hz, 1H), 7.22 (s, 2H), 7.13 (d, J=7.8 Hz, 1H), 7.10-7.03 (m, 2H), 6.80 (s, 1H), 6.69 (d, J=7.2 Hz, 1H), 5.26 (s, 1H), 4.82 (d, J=8.1 Hz, 1H), 4.38-4.21 (m, 4H), 3.29-3.18 (m, 3H), 2.93 (d, J=12.0 Hz, 1H), 2.88 (s, 1H), 0.85-0.80 (m, 2H), 0.65 (mc, 2H).

LCMS m/z [M+H]$^+$ C$_{32}$H$_{28}$FN$_5$O$_3$S requires: 581.66. Found 581.87.

HPLC Tr (min), purity %: 3.32, 98%

Intermediate T (20 mg) and 3,3-difluoroazetidine (30 mg) were dissolved in DMF (1 mL) and triethylamine (0.5 mL). The reaction mixture was stirred at 90° C. overnight. Volatiles were removed under reduced pressure at 40° C. and the resulting residue was purified by preparative HPLC (0% to 95% water/Acetonitrile) to afford 64 (6 mg, 30%) as a yellow powder.

$^1$H-NMR (DMSO, 300 MHz): δ 10.53 (s, 1H), 8.57 (d, J=4.2 Hz, 1H), 8.45 (d, J=4.2 Hz, 1H), 7.90 (d, J=7.2 Hz, 1H), 7.72 (d, J=7.2 Hz, 2H), 7.62 (s, 1H), 7.54 (d, J=4.8 Hz, 1H), 7.23 (t, J=7.8 Hz, 1H), 7.11 (d, J=4.2 Hz, 1H), 6.98-6.82 (m, 2H), 6.75 (d, J=7.2 Hz, 1H), 4.84 (d, J=7.8 Hz, 1H), 4.32-4.20 (m, 4H), 3.28-3.04 (m, 3H), 2.88-2.80 (m, 1H), 0.70 (m, 2H), 0.55 (m, 2H)

LCMS m/z [M+H]$^+$ C$_{32}$H$_{26}$F$_3$N$_5$O$_3$S requires: 617.64. Found 617.86.

HPLC Tr (min), purity %: 3.13, 98%

Example 64

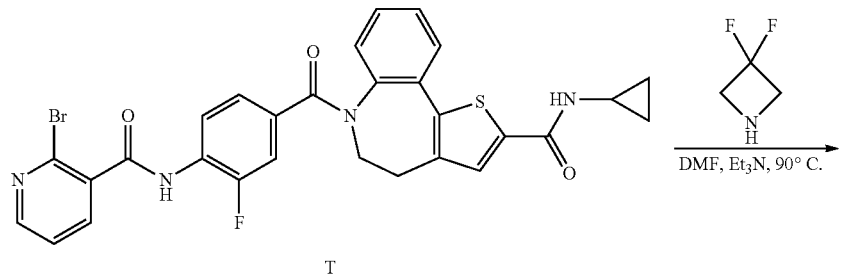

T

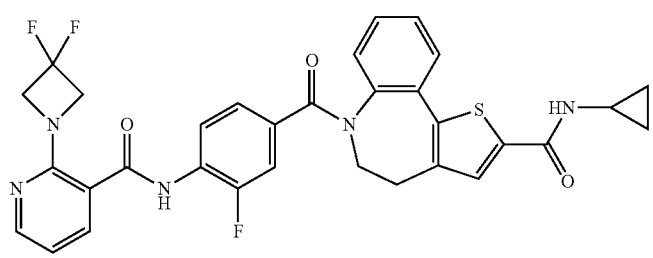

64

Example 65

Example 66

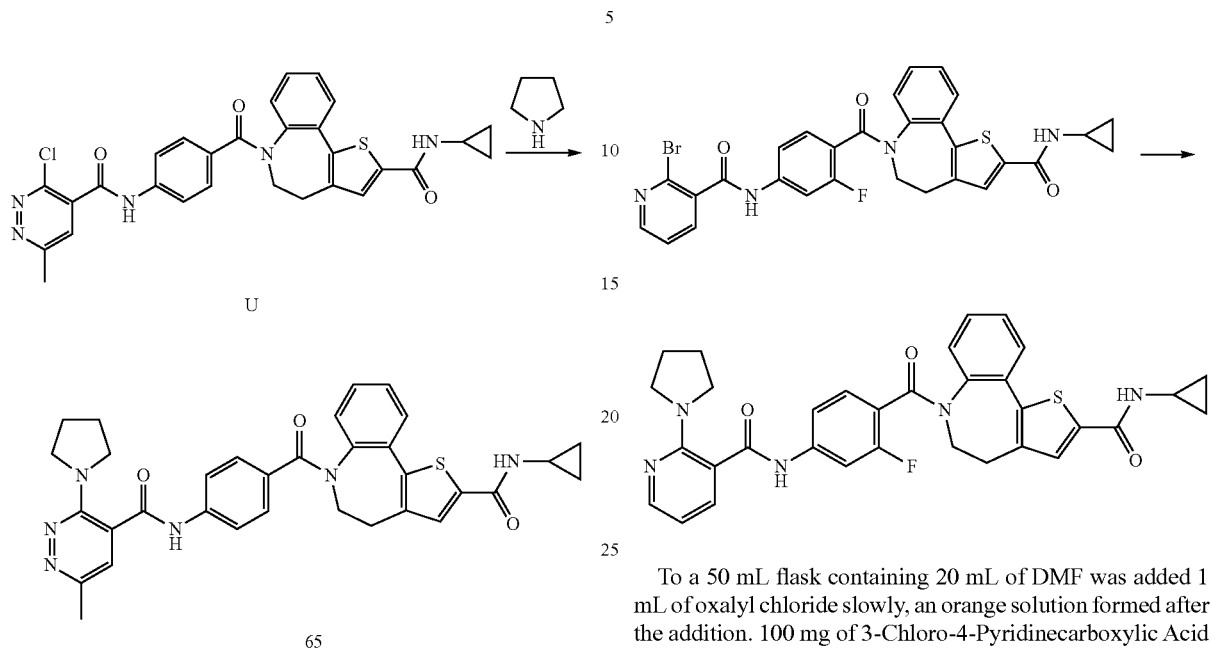

Intermediate U (15 mg) was dissolved in Pyrrolidine (1 mL). The reaction mixture was stirred at RT overnight. Volatiles were removed under reduced pressure at 40° C. and the resulting residue was purified by preparative HPLC (0% to 95% water/Acetonitrile) to afford 65 (7.7 mg, 48%) as a yellow powder.

$^1$H-NMR (DMSO, 300 MHz): δ 8.58 (d, J=9.1 Hz, 1H), 7.92 (s, 1H), 7.70 (s, 1H), 7.63 (d, J=8.1 Hz, 2H), 7.48 (d, J=7.2 Hz, 1H), 6.31-6.28 (m, 3H), 6.04 (d, J=8.4 Hz, 1H), 4.48 (mc, 1H), 4.32-4.20 (m, 5H), 3.91-3.37 (m, 4H), 3.37-2.81 (m, 2H), 2.35-2.30 (m, 1H), 1.82 (s, 3H), 0.70 (m, 2H), 0.55 (m, 2H)

LCMS m/z [M+H]$^+$ C$_{33}$H$_{32}$N$_6$O$_3$S requires: 592.71. Found 592.93.

HPLC Tr (min), purity %: 3.10, 98%

To a 50 mL flask containing 20 mL of DMF was added 1 mL of oxalyl chloride slowly, an orange solution formed after the addition. 100 mg of 3-Chloro-4-Pyridinecarboxylic Acid was dissolved in 2 mL of the above orange solution and stirred for 5 mins at room temperature. Then 100 mg of the intermediate P was dissolved in 1 mL pyridine and then this pyridine solution was added to the above orange carboxylic acid solution. The reaction was finished in 5 min at room temperature. The solvent was then evaporated under vacuum and 0.02 g of the residue was dissolved in pyrrolidine (4 ml) and stirred for 2 h. Volatiles were removed under vacuum and the resulting residue dissolved in CH$_3$CN and water and purified with prep HPLC to afford 66 as a off-white powder (12.2 mg, 43%).

$^1$H-NMR (DMSO, 300 MHz): d 10.67 (s, 1H), 8.51 (d, J=3.9 Hz, 1H), 8.13 (d, J=5.7 Hz, 1H), 7.77-7.30 (m, 3H), 7.63-6.92 (m, 3H), 6.90 (d, J=7.5, 1H), 6.73 (m, 1H), 4.81 (m, 1H), 3.34-2.79 (m, 7H), 1.84 (5, 4H), 0.71 (m, 2H), 0.55 (m, 2H).

LCMS m/z [M+H]$^+$ C$_{33}$H$_{30}$FN$_5$O$_3$S requires: 595.21. Found 596.09.

HPLC Tr (min), purity %: 2.09, 98%

Example 67

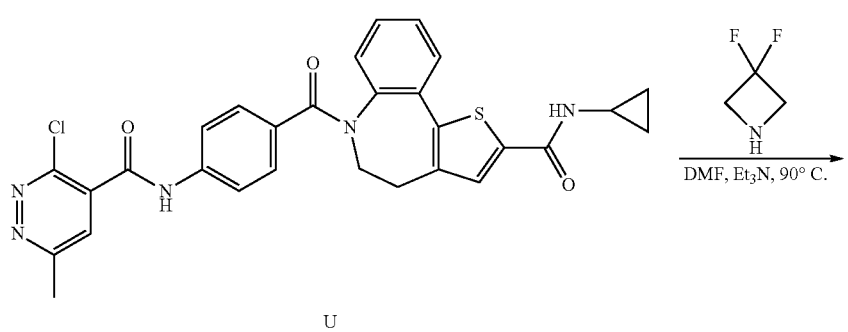

-continued

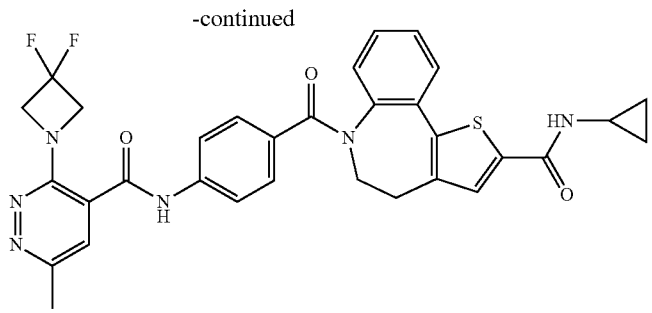

67

Intermediate U (15 mg) was dissolved in DMF (1 mL) and triethylamine (0.1 mL). The reaction mixture was stirred at 90° C. overnight. Volatiles were removed under reduced pressure at 40° C. and the resulting residue was purified by preparative HPLC (0% to 95% water/Acetonitrile) to afford 67 (1 mg, 5%) as a yellow powder.

$^1$H-NMR (DMSO, 300 MHz): δ 7.00 (d, J=9.1 Hz, 1H), 6.97 (s, 1H), 6.76 (s, 1H), 6.70 (d, J=8.7 Hz, 2H), 6.48 (t, J=7.8 Hz, 1H), 6.31-6.28 (m, 3H), 6.04 (d, J=8.4 Hz, 1H), 4.18 (mc, 1H), 4.32-4.20 (m, 4H), 3.28-3.05 (m, 3H), 2.35-2.30 (m, 1H), 1.82 (s, 3H), 0.70 (m, 2H), 0.56 (m, 2H)

LCMS m/z [M+H]$^+$ $C_{32}H_{28}F_2N_6O_3S$ requires: 614.66. Found 614.87.

HPLC Tr (min), purity %: 3.12, 98%

The invention claimed is:

1. The present invention provides a compound of Formula I:

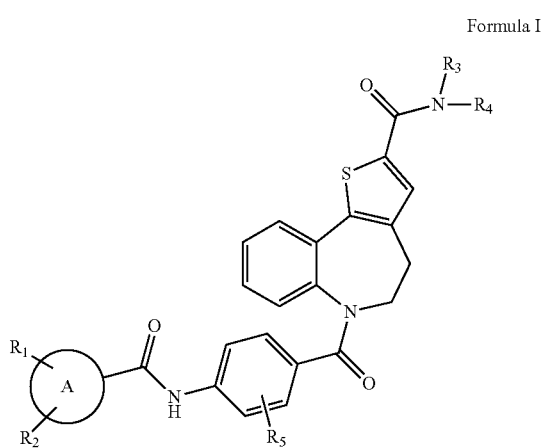

Formula I wherein A is aryl or heteroaryl;
$R_1$ is selected from alkyl, alkoxy, haloalkyl, aryl, heteroaryl, heterocyclyl, and cycloalkyl, said heterocyclyl is optionally substituted by one to three substituents independently selected from the group consisting of halo, hydroxyl, haloalkyl, alkoxy, alkyl, alkoxy-alkyl-, hydroxyl-alkyl-, CN, and alkyl-NH—: said aryl or heteroaryl is optionally substituted by one to three substituents independently selected from the group consisting of halo, cyano, nitro, hydroxyl, alkyl, alkoxy, and alkyl-NH—, with the proviso that when A is aryl, $R_1$ is not unsubstituted aryl;
$R_2$ is selected from hydrogen, alkyl, alkoxy, amino, alkyl-NH—, CN, alkyl-SO$_2$—, and halo;
$R_3$ is selected from hydrogen, alkyl, heterocyclyl, heteroaryl, heteroaryl-alkyl- and cycloalkyl, wherein said alkyl is optionally substituted by one substituent selected from the group consisting of NH$_2$—C(O)—, halo, hydroxyl, NH$_2$—SO$_2$—, alkoxy-alkyl-, heterocyclyl; aryl, heteroaryl, CN, and alkyl-NH—;
$R_4$ is selected from hydrogen, alkyl and haloalkyl;
$R_3$ and $R_4$ taken together with the nitrogen atom to which they are attached optionally form a 3- to 7-membered ring;
$R_5$ is selected from hydrogen, alkyl, alkoxy, haloalkyl, and halo; or
a pharmaceutically acceptable salt thereof.

2. The compound of claim 1 wherein A is $C_6$-$C_{10}$ aryl or monocyclic 6-membered heteroaryl.

3. The compound of claim 1 wherein A is monocyclic 5-membered heteroaryl or bicyclic 8- to 10-membered heteroaryl.

4. The compound of claim 1 wherein A is a monocyclic 5-membered heteroaryl; $R_1$ is alkyl, or aryl; $R_2$ is hydrogen, or alkyl; $R_3$ is cycloalkyl, or alkyl; $R_4$ is hydrogen; $R_5$ is hydrogen, or halo.

5. The compound of claim 4 wherein A is thienyl or pyrazolyl group.

6. The compound of claim 1 wherein A is a bicyclic 8- to 10-membered heteroaryl; $R_1$ is alkyl; $R_2$ is hydrogen, or alkyl; $R_3$ is cycloalkyl, or alkyl; $R_4$ is hydrogen; $R_5$ is hydrogen, or halo.

7. The compound of claim 6 wherein A is indolyl, indazolyl, or quinoxalinyl group.

8. A compound of Formula IA:

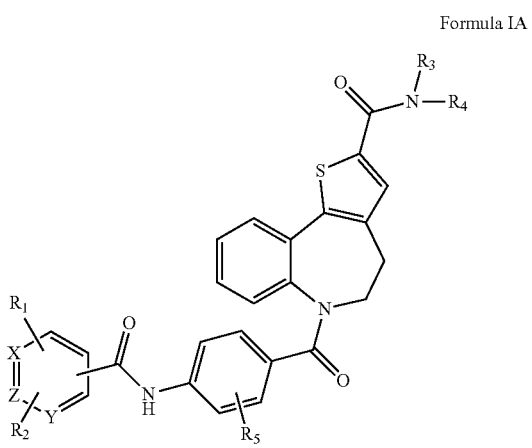

Formula IA wherein X, Y and Z are independently N or CH;
R₁ is selected from alkyl, alkoxy, haloalkyl, aryl, heteroaryl, and heterocyclyl, said heterocyclyl is optionally substituted by one to three substituents independently selected from the group consisting of halo, hydroxyl, haloalkyl, alkoxy, alkyl, alkoxy-alkyl-, and hydroxyl-alkyl-, said aryl is optionally substituted by one to two substituents independently selected from the group consisting of halo,
cyano, nitro and hydroxyl, with the proviso that when X and Y are simultaneously CH, R₁ is not unsubstituted aryl;
R₂ is selected from hydrogen, alkyl, alkoxy, and halo;
R₃ is hydrogen, alkyl, heterocyclyl, heteroaryl, heteroaryl-alkyl-, or cycloalkyl, said alkyl is optionally substituted by one substituent selected from the group consisting of NH₂—C(O)—, halo, hydroxyl, NH₂—SO₂ alkoxy-alkyl-, and heterocyclyl;
R₄ is hydrogen, or alkyl;
R₃ and R₄ taken together with the nitrogen atom to which they are attached optionally form a 3- to 7-membered ring;
R₅ is selected from hydrogen, alkyl, alkoxy, haloalkyl, and halo; or
a pharmaceutically acceptable salt thereof.

9. The compound of claim 8 wherein X and Z are CH, and Y is N.

10. The compound of claim 8 wherein X, Y and Z are CH.

11. The compound of claim 8 wherein X and Z are N, Y is CH.

12. The compound of claim 8 wherein X and Z are CH; Y is N; R₁ is haloalkyl, or heterocyclyl, said heterocyclyl is optionally substituted by one to two substituents independently selected from the group consisting of halo, hydroxyl, alkoxy-alkyl-, alkyl, haloalkyl, and hydroxyl-alkyl-: R₂ is hydrogen; R₃ is selected from hydrogen, alkyl, heteroaryl, heteroaryl-alkyl-, and cycloalkyl, said alkyl is optionally substituted by one substituent selected from the group consisting of NH₂—C(O)—, halo, hydroxyl, NH₂—SO₂—, alkoxy-alkyl-, and heterocyclyl; R₄ is hydrogen, or alkyl; R₃ and R₄ taken together with the nitrogen atom to which they are attached optionally form a 3- to 7-membered ring; R₅ is hydrogen, or halo; or a pharmaceutically acceptable salt thereof; or an optical isomer thereof, or a mixture of optical isomers.

13. The compound of claim 12 wherein R₁ is (C₁-C₄)haloalkyl, or 4- to 7-membered heterocyclyl, said heterocyclyl is optionally substituted by one to two substituents independently selected from the group consisting of halo, hydroxyl, (C₁-C₄)alkoxy-(C₁C₄)alkyl-,
(C₁C₄)alkyl, (C₁C₄)haloalkyl, and hydroxyl(C₁-C₄)alkyl; R₃ is selected from hydrogen, (C₁-C₄)alkyl, 5- to 9-membered heteroaryl, 5- to 9-membered heteroaryl-(C₁-C₄)alkyl-, and (C₃-C₇)cycloalkyl, said alkyl is optionally substituted by one substituent selected from the group consisting of NH₂—C(O)—, halo, hydroxyl, NH₂—SO₂—, (C₁-C₄)alkoxy-(C₁-C₄)alkyl-, and 4- to 7-membered heterocyclyl; R₄ is hydrogen, or (C₁-C₄)alkyl; or a pharmaceutically acceptable salt thereof; or an optical isomer thereof, or a mixture of optical isomers.

14. The compound of claim 8 wherein X, Y and Z are CH; R₁ is selected from alkyl, alkoxy, and heteroaryl; R₂ is hydrogen, or alkoxy; R₃ is cycloalkyl; and R₄ and R₅ are hydrogen; or a pharmaceutically acceptable salt thereof; or an optical isomer thereof, or a mixture of optical isomers.

15. The compound of claim 14 wherein R₁ is (C₁-C₄)alkyl, (C₁-C₄)alkoxy, or 5- to 9-membered heteroaryl; R₂ is hydrogen, or (C₁-C₄)alkoxy; R₃ is (C₃-C₇)cycloalkyl; and R₄ and R₅ are hydrogen.

16. The compound of claim 8 wherein X and Z are N, Y is CH; R₁ is alkyl, alkoxy, or heteocyclyl; R₂ is alkyl; R₃ is cycloalkyl; and R₄ and R₅ are hydrogen; or a pharmaceutically acceptable salt thereof.

17. A compound of Formula IB:

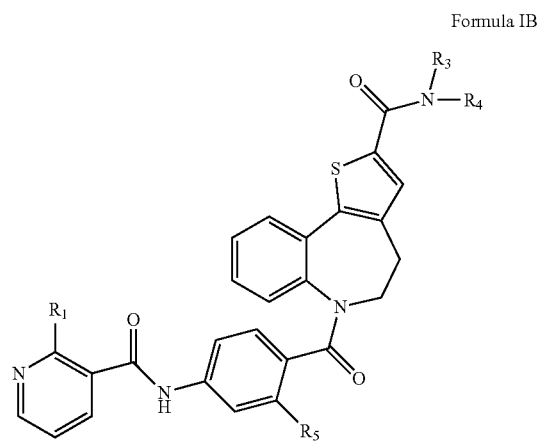

Formula IB wherein R₁ is haloalkyl, or heterocyclyl, said heterocyclyl is optionally substituted by one to two substituents independently selected from the group consisting of halo, hydroxyl, alkoxy-alkyl-, alkyl, haloalkyl, and hydroxyl-alkyl-; R₃ is selected from hydrogen, alkyl, heterocyclyl, heteroaryl, heteroaryl-alkyl-, and cycloalkyl, said alkyl is optionally substituted by one substituent selected from the group consisting of NH₂—C(O)—, halo, and hydroxyl; R₄ is hydrogen; and R₅ is hydrogen, or halo; or a pharmaceutically acceptable salt thereof; or an optical isomer thereof, or a mixture of optical isomers.

18. The compound of claim 17 wherein R₁ is heterocyclyl that is optionally substituted by one to two substituents independently selected from the group consisting of halo, hydroxyl, alkoxy-alkyl-, alkyl, haloalkyl, and hydroxyl-alkyl-.

19. The compound of claim 17 wherein R₁ is 4- to 7-membered heterocyclyl that is optionally substituted by one to two substituents independently selected from the group consisting of halo, hydroxyl, (C₁-C₄)alkoxy-(C₁-C₄)alkyl-, (C₁-C₄)alkyl, (C₁-C₄)haloalkyl, and hydroxyl-(C₁-C₄)alkyl-; R₃ is hydrogen, (C₃-C₇)cycloalkyl, 4- to 7-membered heterocyclyl, or (C₁-C₄)alkyl that is optionally substituted by one halo group or one 5- to 6-membered heteroaryl group; and R₄ and R₅ are hydrogen; or a pharmaceutically acceptable salt thereof; or an optical isomer thereof, or a mixture of optical isomers.

20. The compound of claim 19 wherein R₁ is pyrrolidinyl; R₃ is selected from hydrogen, cyclopropyl, and (C₁-C₄)alkyl, wherein the (C₁-C₄)alkyl is optionally substituted by one halo group or one 5- to 6-membered heteroaryl group; and R₄ and R₅ are hydrogen; or a pharmaceutically acceptable salt thereof; or an optical isomer thereof, or a mixture of optical isomers.

21. The compound of claim 19 wherein R₁ is azetidinyl or 2-oxa-6-azaspiro[3,3]heptan-6-yl; R₃ is cyclopropyl; and R₄ and $R_5$ are hydrogen; or a pharmaceutically acceptable salt thereof; or an optical isomer thereof, or a mixture of optical isomers.

22. A method of treating a subject infected with RSV, comprising administering to the subject a therapeutically effective amount of the compound according to claim 1.

23. A pharmaceutical composition comprising a therapeutically effective amount of a compound of according to claim 1 and one or more pharmaceutically acceptable carriers.

24. The pharmaceutical composition of claim 23, further comprising a second therapeutic agent selected from the group consisting of: an anti-inflammatory agent selected from salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbiprofen, oxaprozin, piroxicam, meloxicam, ampiroxicam, droxicam, tenoxicam, nabumetone, phenylbutazone, oxyphenbutazone, antipyrine, aminopyrine, apazone, nimesulide, zileuton, aurothioglucose, gold sodium thiomalate, auranofin, colchicine, allopurinol, probenecid, sulfinpyrazone, and benzbromarone;

an anti-viral agent selected from zidovudine, acyclovir, ganciclovir, vidarabine, idoxuridine, trifluridine, ribavirin, foscarnet, amantadine, rimantadine, saquinavir, indinavir, and ritonavir; and palivizumab.

\* \* \* \* \*